US012600703B2

(12) United States Patent
Kiernan et al.

(10) Patent No.: US 12,600,703 B2
(45) Date of Patent: Apr. 14, 2026

(54) METHODS OF SYNTHESIZING FARNESYL DIBENZODIAZEPINONES

(71) Applicant: AMO Pharma Ltd., Durham, NC (US)

(72) Inventors: Bernard Matthew Kiernan, Phoenixville, PA (US); Thomas R. Bailey, Phoenixville, PA (US); Binfeng Li, Suzhou (CN)

(73) Assignee: AMO PHARMA LTD., Leeds (GB)

( * ) Notice: Subject to any disclaimer, the term of this patent is extended or adjusted under 35 U.S.C. 154(b) by 575 days.

(21) Appl. No.: 17/926,407

(22) PCT Filed: May 28, 2021

(86) PCT No.: PCT/US2021/034786
§ 371 (c)(1),
(2) Date: Nov. 18, 2022

(87) PCT Pub. No.: WO2021/243171
PCT Pub. Date: Dec. 2, 2021

(65) Prior Publication Data
US 2023/0192629 A1 Jun. 22, 2023

Related U.S. Application Data

(60) Provisional application No. 63/031,911, filed on May 29, 2020.

(51) Int. Cl.
*C07D 243/38* (2006.01)

(52) U.S. Cl.
CPC .................................. *C07D 243/38* (2013.01)

(58) Field of Classification Search
CPC .................................................... C07D 243/38
See application file for complete search history.

(56) References Cited

U.S. PATENT DOCUMENTS

2008/0199940 A1 8/2008 McAlpine et al.
2018/0105502 A1 4/2018 Burke et al.

FOREIGN PATENT DOCUMENTS

WO 2016/207790 12/2016

OTHER PUBLICATIONS

International Search Report and Written Opinion of the International Searching Authority issued Sep. 10, 2021 in International (PCT) Application No. PCT/US21/34786.
Yu, Yongguo et al., "Design, Synthesis and Anticancer Activity Evaluation of Diazepinomicin Derivatives", Letters in Drug Design & Discovery, 2013, vol. 10, pp. 369-373.
Bonitz, Tobias et al., "Unusual N-Prenylation in Diazepinomicin Biosynthesis: The Farnesylation of a Benzodiazepine Substrate Is Catalyzed by a New Member of the ABBA Prenyltransferase Superfamily", PLOS One, Dec. 2013, vol. 8, Issue 12, e85707, 12 pages.
Yusuke Takahashi, et al., "First synthesis of BU-4664L", Tetrahedron Letters, 2015, vol. 56, pp. 5670-5672.

*Primary Examiner* — Paul V Ward
(74) *Attorney, Agent, or Firm* — Wenderoth, Lind & Ponack, L.L.P.

(57) ABSTRACT

The present invention is directed to synthetic means for producing farnesyl dibenzodiazepinone compounds, including AMO-01.

AMO-01

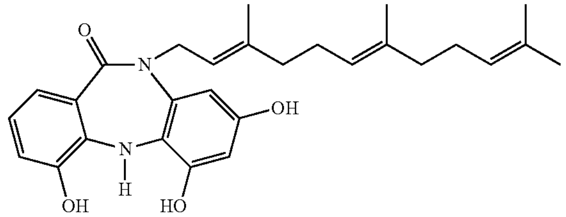

4 Claims, 2 Drawing Sheets

METHODS OF SYNTHESIZING FARNESYL DIBENZODIAZEPINONES

BACKGROUND OF INVENTION

The euactinomycetes are a subset of a large and complex group of Gram-positive bacteria known as actinomycetes. Over the past few decades these organisms, which are abundant in soil, have generated significant commercial and scientific interest as a result of the large number of therapeutically useful compounds, particularly antibiotics, produced as secondary metabolites. The intensive search for strains able to produce new antibiotics has led to the identification of hundreds of new species.

Many of the euactinomycetes, particularly *Streptomyces* and the closely related *Saccharopolyspora* genera, have been extensively studied. Both of these genera produce a notable diversity of biologically active metabolites. Because of the commercial significance of these compounds, much is known about the genetics and physiology of these organisms. Another representative genus of euactinomycetes, *Micromonospora*, has also generated commercial interest. For example, U.S. Pat. No. 5,541,181 (Ohkuma et al.) discloses a dibenzodiazepinone compound, specifically 5-farnesyl-4,7,9-trihydroxy-dibenzodiazepin-11-one (named "BU-4664L"), produced by a known euactinomycetes strain, *Micromonospora* sp. M990-6 (ATCC 55378). The Ohkuma et al. patent reports that BU-4664L and its chemically synthesized di- and tri-alkoxy and acyloxy derivatives possess anti-inflammatory and anti-tumor cell activities. In another example, U.S. Pat. No. 7,101,872 (Bachmann et al.) discloses a farnesyl dibenzodiazepinone compound, specifically 10-farnesyl-4,6,8-trihydroxy-dibenzodiazepin-11-one (named "ECO-04601", and "AMO-01" herein).

Research into pharmaceutical applications for these compounds would be aided by repeatable means for producing sufficient quantities of the compounds at acceptable levels of purity for both in vitro and animal testing. Available methods for preparing dibenzodiazepinone compounds are largely based on culturing microorganisms under conditions that induce production of the compounds, and then subjecting culture media and fermentation broth to multiple rounds of extraction, concentration and purification. These means are costly and time consuming.

Thus, there exists a considerable need to develop synthetic means for producing dibenzodiazepinone compounds. The present invention is direct to this and other important goals.

BRIEF SUMMARY OF INVENTION

The present invention is directed to novel means for the synthesis of farnesyl dibenzodiazepinone compounds, such as AMO-01 defined herein.

AMO-01

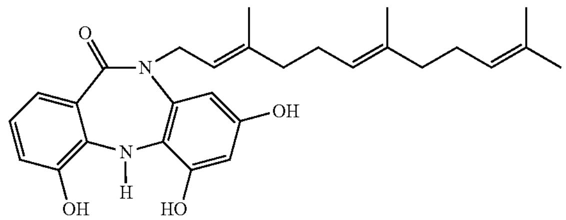

As discussed in detail below, the methods for synthesizing some of the farnesyl dibenzodiazepinone compounds of the present invention are based on the surprising discovery by the inventors that use of an Ullmann coupling reaction in the method, with careful control over the amount of copper in the reaction, achieves a surprising degree of regioselectivity in the resulting compounds. In contrast, the palladium-catalyzed Buchwald coupling yields opposite regiochemistry from the identical starting materials. This difference is utilized in the methods disclosed herein, allowing production of farnesyl dibenzodiazepinone compounds with selected stereochemistry.

In a first embodiment, the invention is directed to methods of synthesizing farnesyl dibenzodiazepinones of Formula I, as well as salt thereof:

Formula I

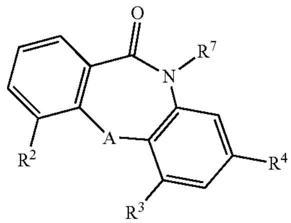

wherein,

A is —NH—;

$R^7$ is —$CH_3$, —$(CH_2)_xCH_3$, —$CH_2CH_2W^1CH_3$, —$CH_2CH_2W^1CH_2CH_2W^2CH_3$ or —$CH_2W^1CH_2CH_2W^2CH_2CH_2W^3CH_3$, where x is an integer of from 1 to 11, and where each of $W^1$, $W^2$ and $W^3$ is independently

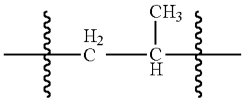 or 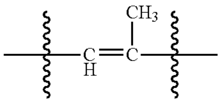 ;

$R^2$ is —H, —OH, —$OCH_3$ or —OP═O($OR^8$), where $R^8$ is —Na, —$CH_3$ or —$CH_2CH_3$; and $R^3$ and $R^4$ are the same and selected from —H, —OH, —$OCH_3$ or —OP═O($OR^8$), where $R^8$ is —Na, —$CH_3$ or —$CH_2CH_3$. In certain aspects, the method is via the Ullmann reaction.

The method of synthesizing farnesyl dibenzodiazepinones of Formula I comprises the following steps, wherein A, $R^2$, $R^3$, $R^4$, $R^7$, $R^8$, $W^1$, $W^2$, $W^3$ and x are as defined above for Formula I:

(a) preparing AP2312-A;

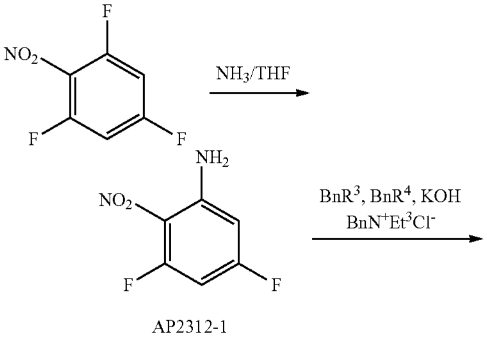

AP2312-1

-continued
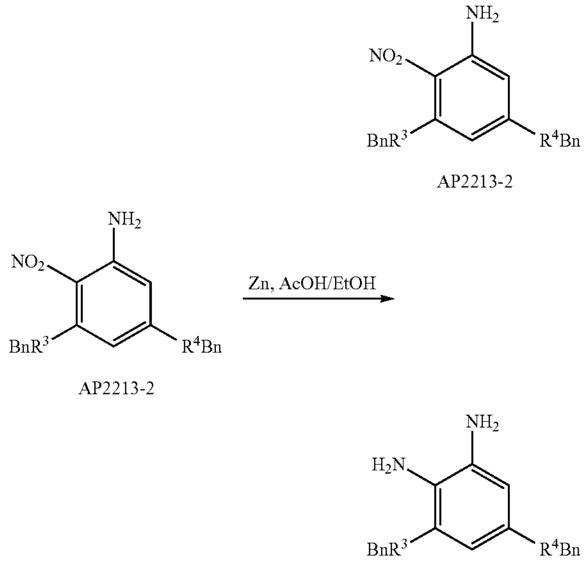
AP2213-2
AP2213-2
AP2312-A
(b) preparing AP2312-B;
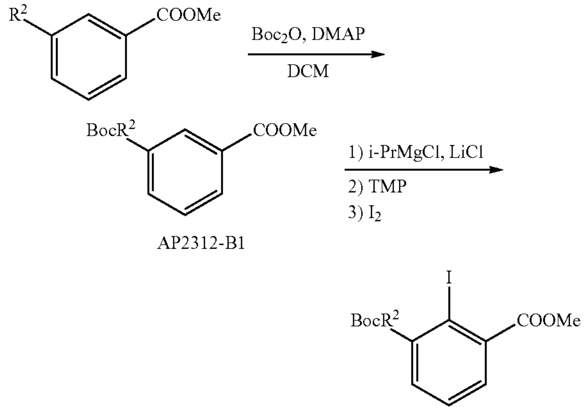
AP2312-B1
AP2312-B2
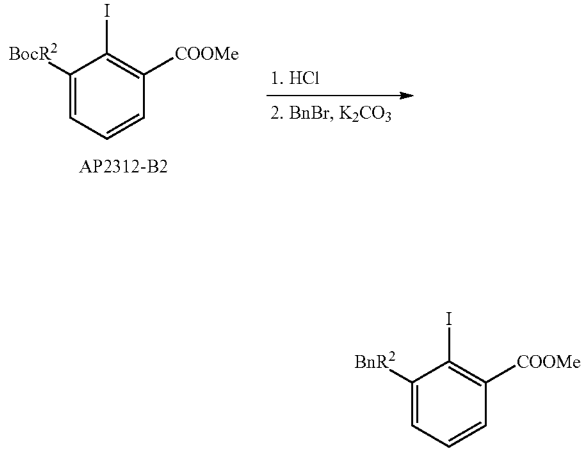
AP2312-B2
AP2312-B
(c) performing Ullmann coupling;
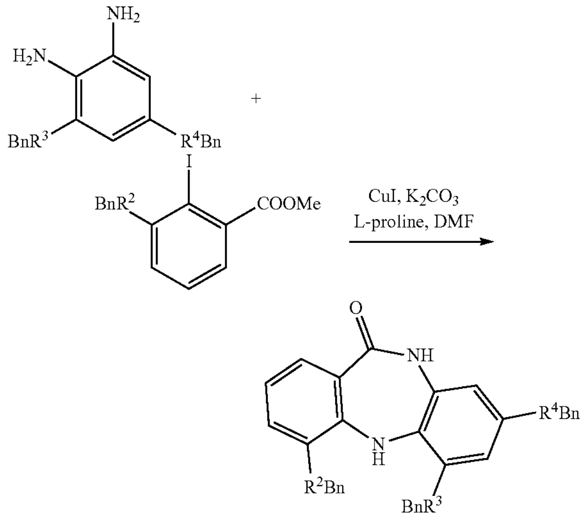
(d) performing de-benzylation;
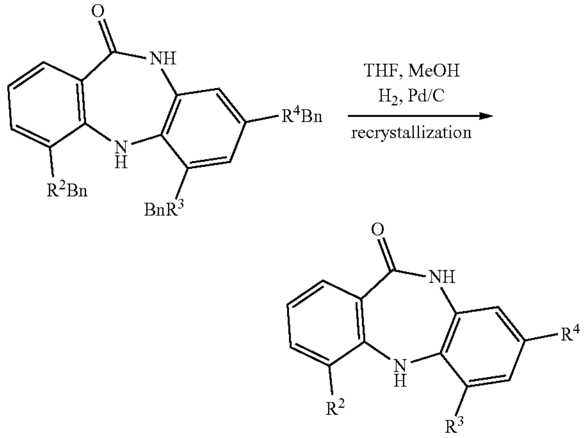
(e) performing silylation;
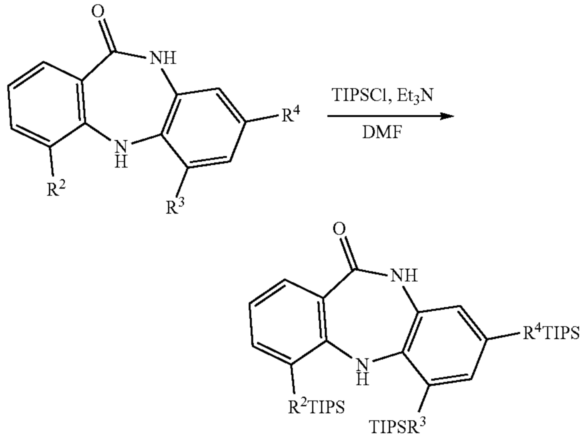

(f) preparing $R^7$;

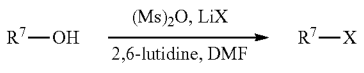

wherein X is Br, I, or Cl (g) performing farnesylation; and

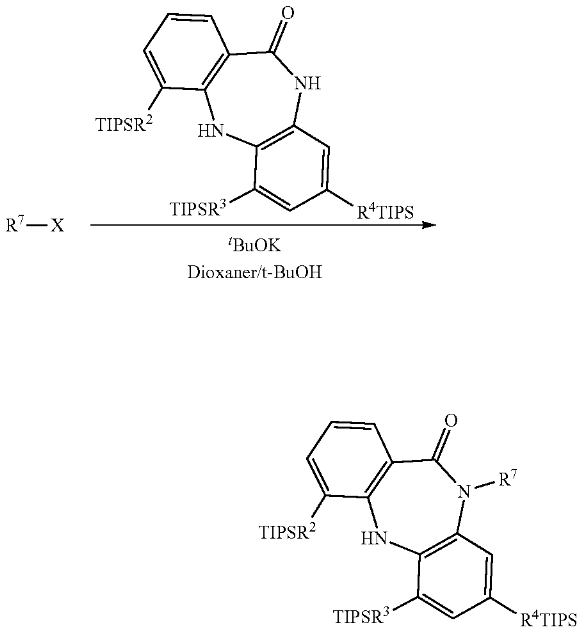

(h) performing de-silylation

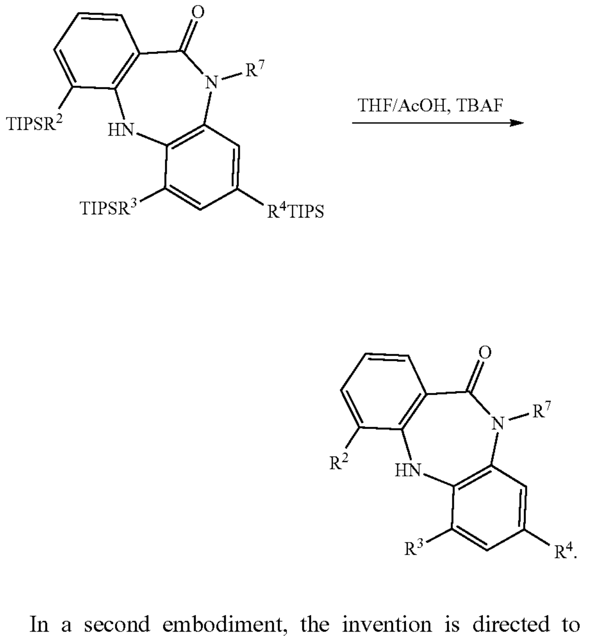

In a second embodiment, the invention is directed to methods of synthesizing farnesyl dibenzodiazepinones of Formula II, as well as salt thereof:

Formula II

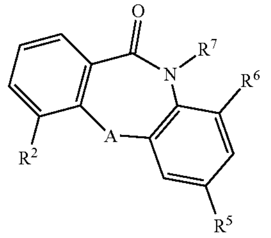

wherein,

A is —NH—;

$R^7$ is $-CH_3$, $-(CH_2)_xCH_3$, $-CH_2CH_2W^1CH_3$, $-CH_2CH_2W^1CH_2CH_2W^2CH_3$ or $-CH_2W^1CH_2CH_2W^2CH_2CH_2W^3CH_3$, where x is an integer of from 1 to 11, and where each of $W^1$, $W^2$ and $W^3$ is independently

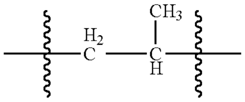
or
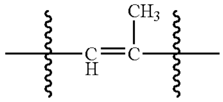
;

$R^2$ is —H, —OH, $-OCH_3$ or $-OP{=}O(OR^8)$, where $R^8$ is —Na, $-CH_3$ or $-CH_2CH_3$; and $R^5$ and $R^6$ are the same and selected from —H, —OH, $-OCH_3$ or $-OP{=}O(OR^8)$, where $R^8$ is —Na, $-CH_3$ or $-CH_2CH_3$. In certain aspects, the method is via Buchwald coupling.

The method of synthesizing farnesyl dibenzodiazepinones of Formula II comprises the following steps, wherein A, $R^2$, $R^5$, $R^6$, $R^7$, $R^8$, $W^1$, $W^2$, $W^3$ and x are as defined above for Formula II:

(a) preparing AP2312-A;

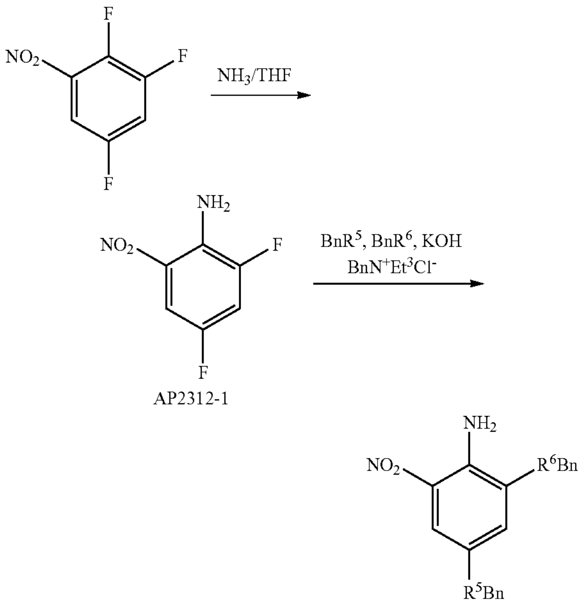

AP2312-1

AP2213-2

-continued
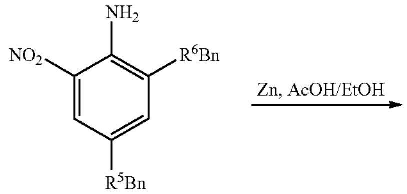
AP2213-2
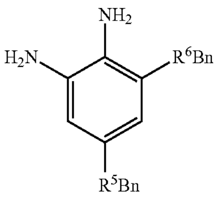
AP2312-A
(b) preparing AP2312-B;
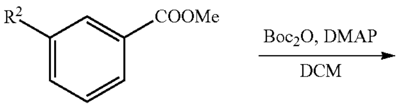
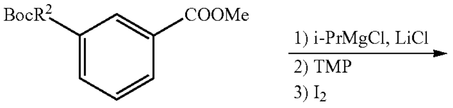
AP2312-B1
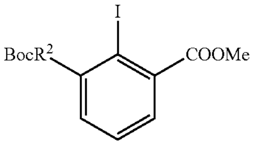
AP2312-B2
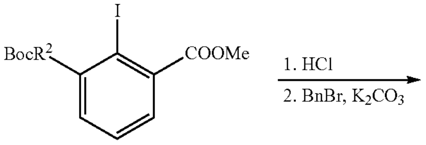
AP2312-B2
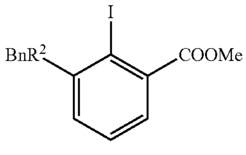
AP2312-B
(c) performing Buchwald coupling;
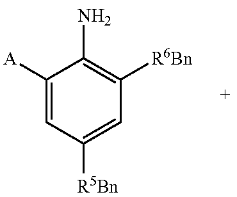
-continued
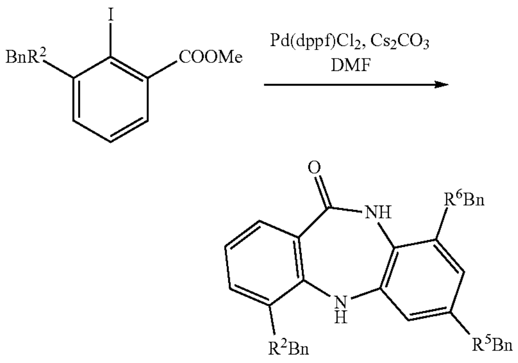
(d) performing de-benzylation;
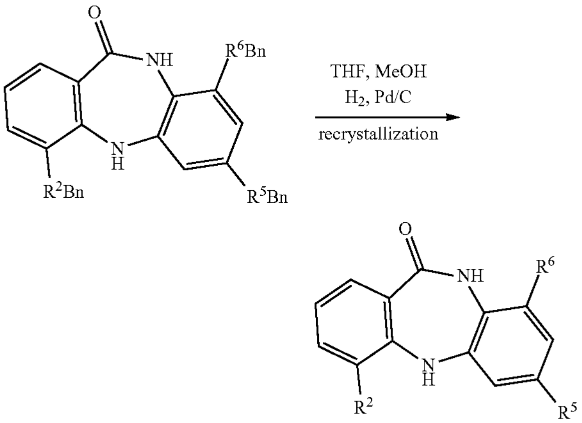
(e) performing silylation;
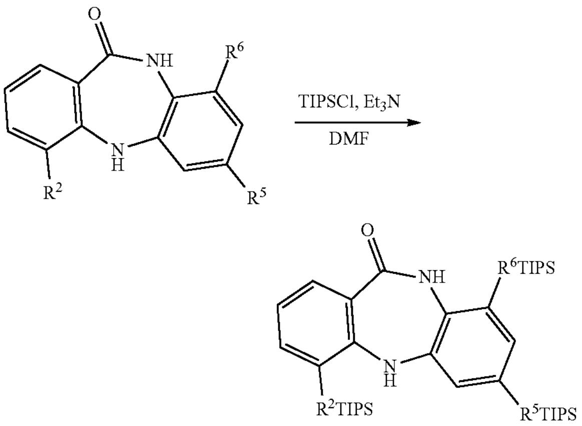
(f) preparing $R^7$;
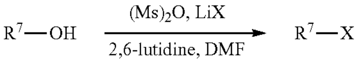
wherein X is Br, I, or Cl (g) performing farnesylation; and
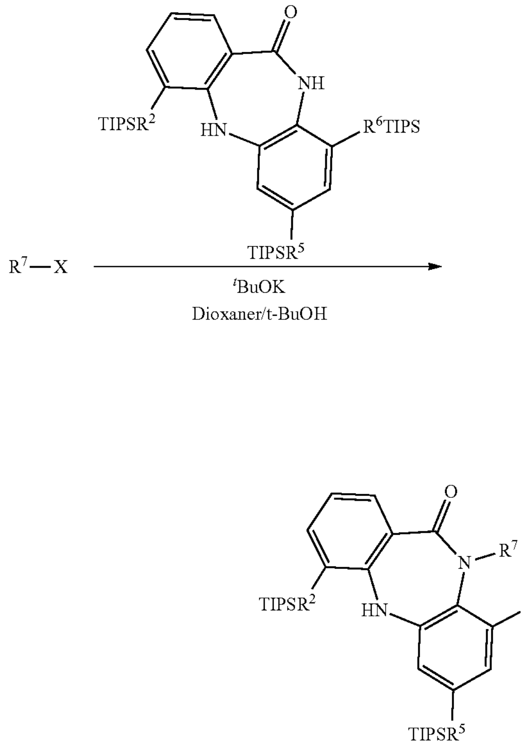
(h) performing de-silylation
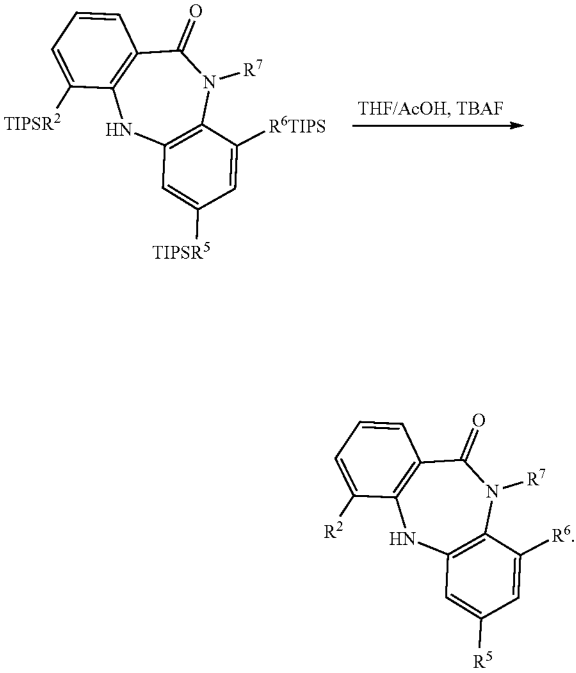
In a third embodiment, the invention is directed to methods of synthesizing the farnesyl dibenzodiazepinone AMO-01 (10-farnesyl-4,6,8-trihydroxy-dibenzodiazepin-11-one; also termed "AP2312")
AMO-01
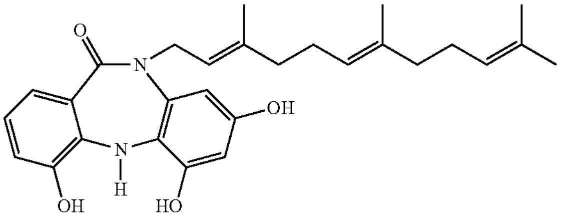
In one aspect, the method comprises the following steps:
(a) preparing AP2312-A;
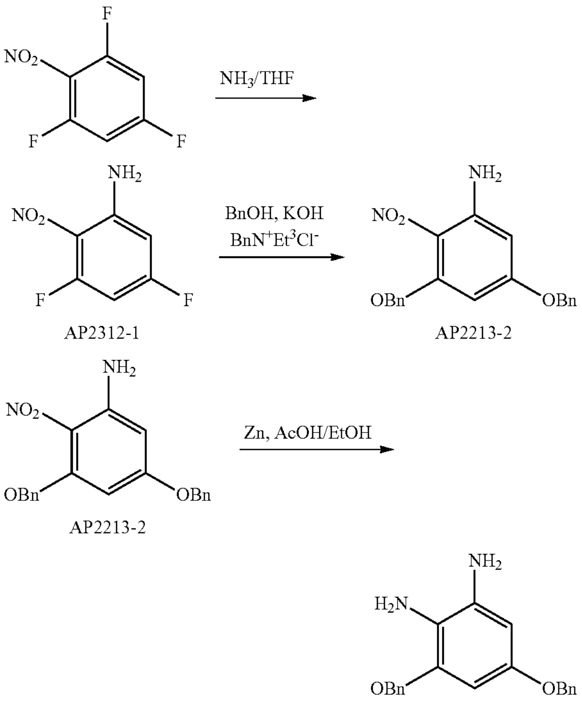
AP2312-1
AP2213-2
AP2213-2
AP2312-A
(b) preparing AP2312-B;
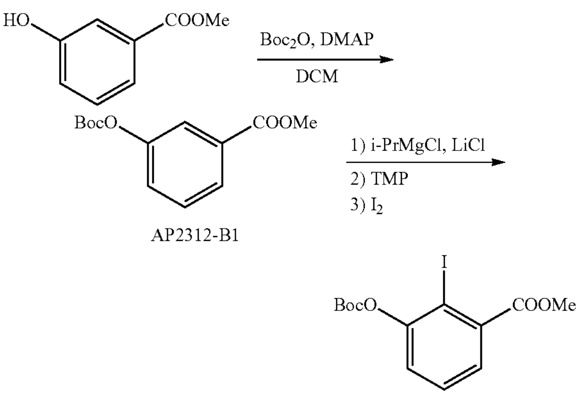
AP2312-B1
AP2313-B2

-continued
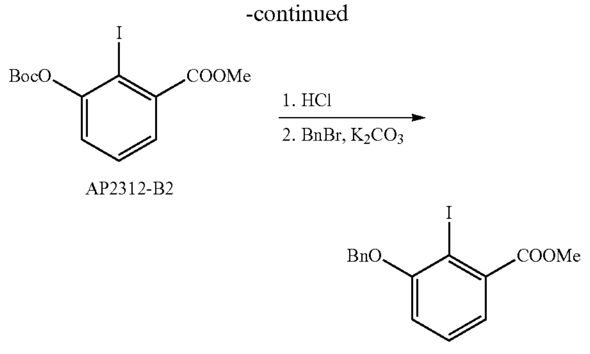
AP2312-B2
AP2312-B
(c) performing Ullmann coupling;
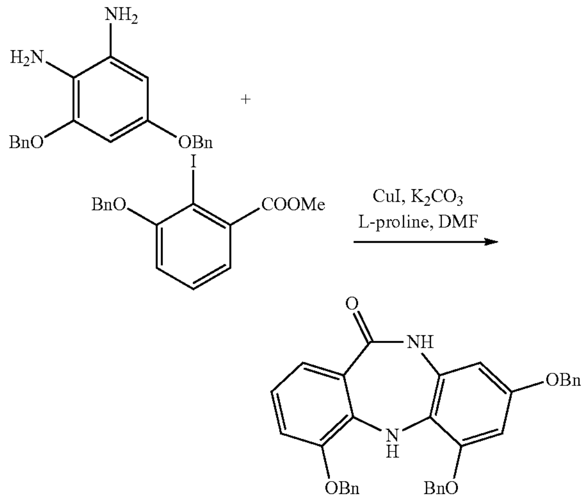
(d) performing de-benzylation;
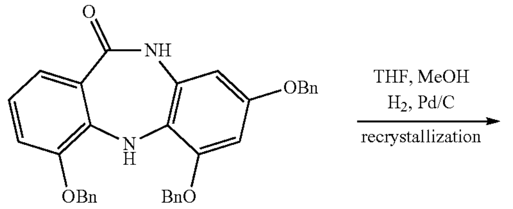
-continued
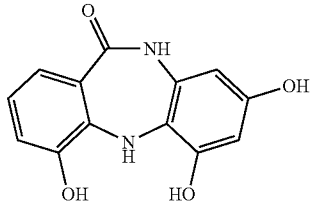
(e) performing silylation;
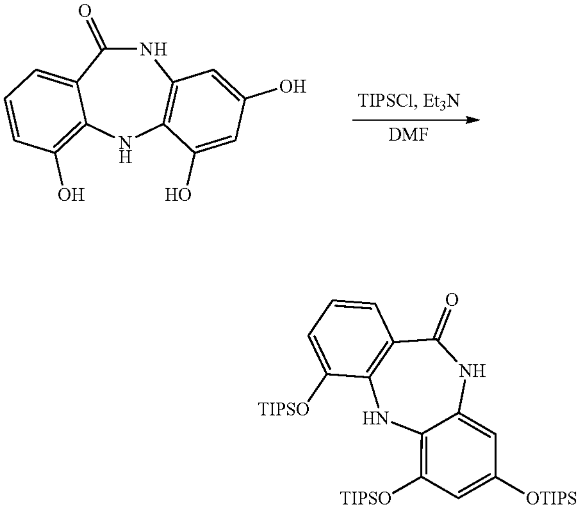
(f) preparing farnesyl bromide;
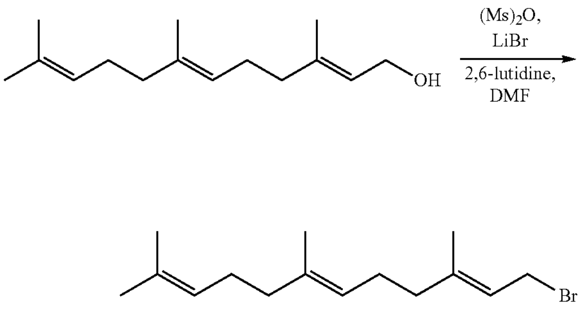
(g) performing farnesylation; and
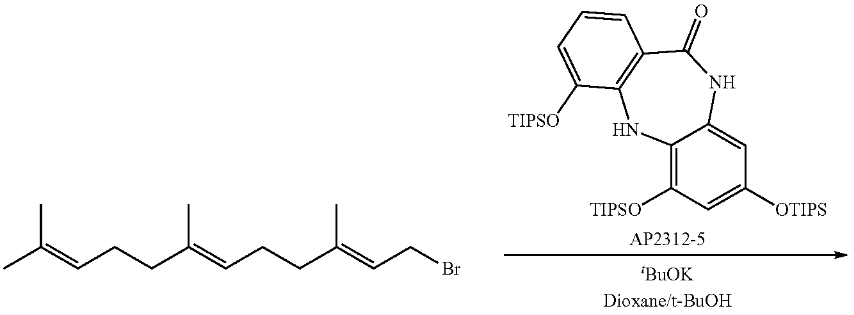

-continued
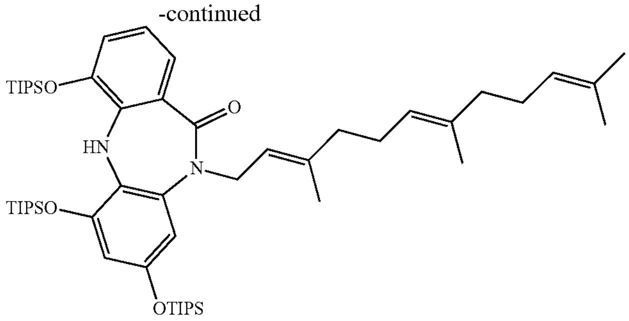
(h) performing de-silylation
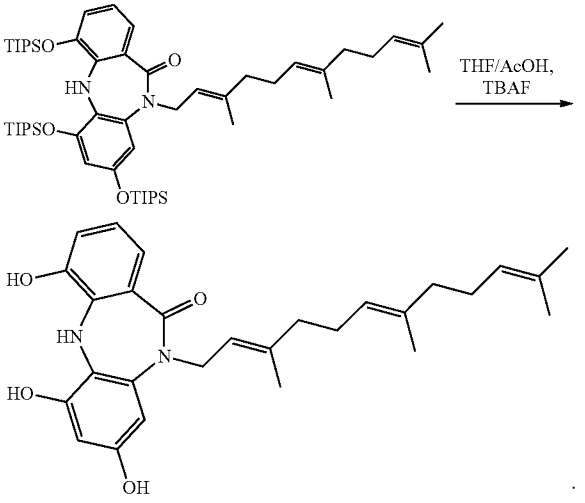
In a specific aspect, the method of synthesizing AMO-01 comprises the following steps:
(a) preparing AP2312-A;
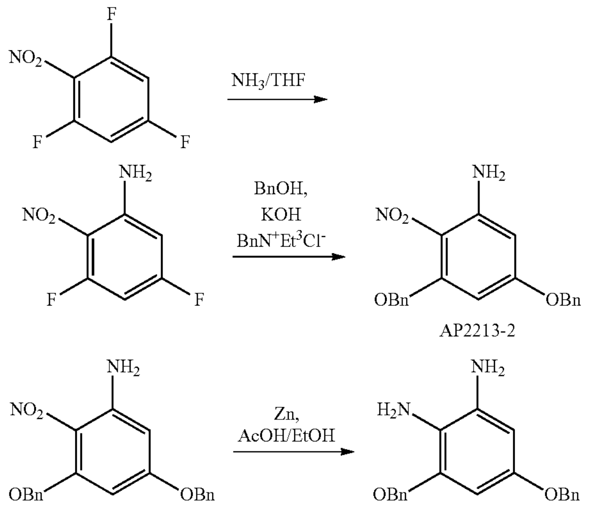
AP2213-2
AP2213-2
AP2312-A
(b) preparing AP2312-B;
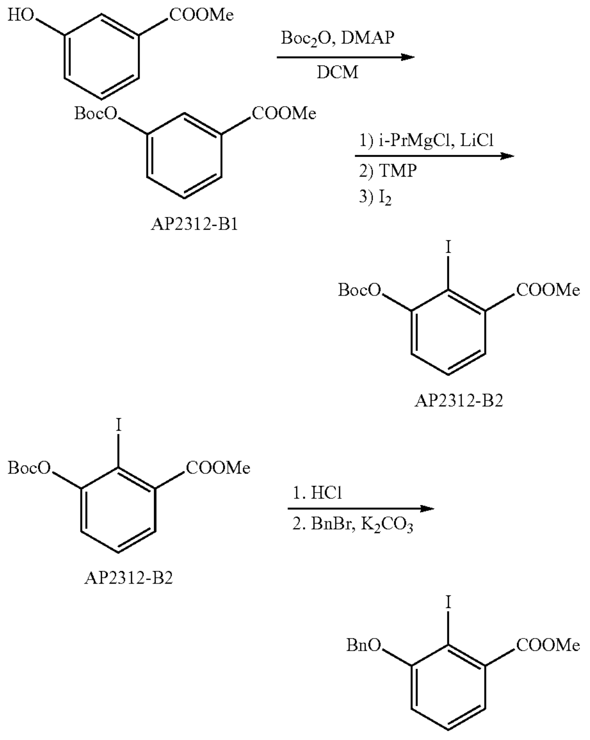
AP2312-B1
AP2312-B2
AP2312-B2
AP2312-B
(c) performing Ullmann coupling by reacting molecular equivalent amounts of AP2312-A and AP2312-B in the presence of CuI (0.0525 eq), $K_2CO_3$ (2.0 eq), L-proline (0.1 eq) and DMF to yield AP2312-3;
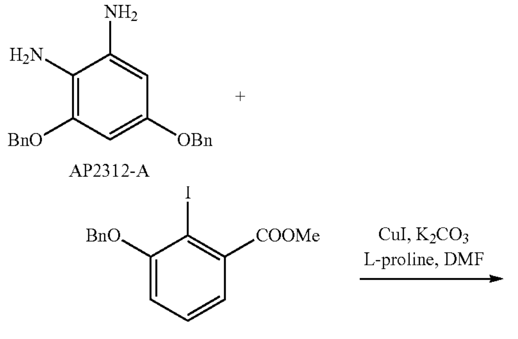
AP2312-A
AP2312-B -continued

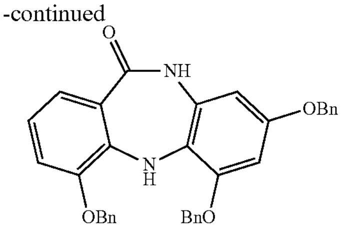

AP2312-3

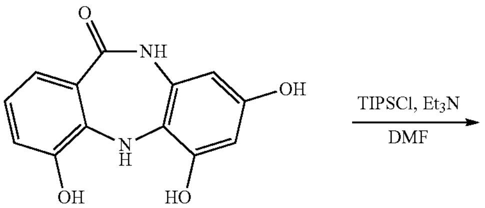

AP2312-4

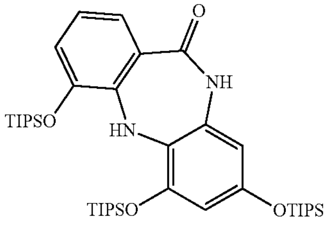

AP2312-5

(d) performing de-benzylation of AP2312-3 in the presence of THF, MeOH and Pd/C under $H_2$ to yield AP2312-4;

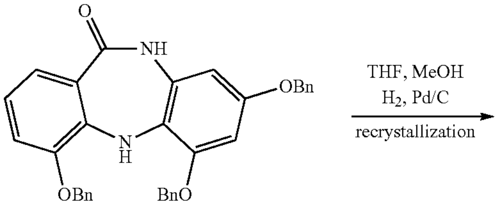

AP2312-3

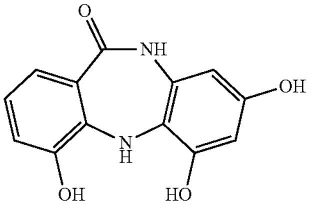

AP2312-4

(e) performing silylation of AP2312-4 in the presence of TIPSCl (4.0 eq), $Et_3N$ (5.0 eq) and DMF to yield AP2312-5;

(f) reacting AP23132-C in the presence of $Ms_2O$, LiBr (1.6 eq), 2,6-lutidine (1.6 eq) and DMF to yield AP2312-6;

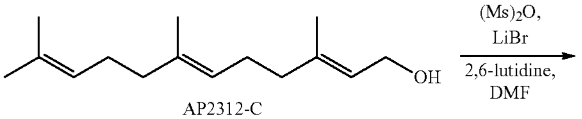

AP2312-C

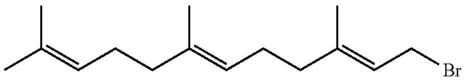

AP2312-6

(g) performing farnesylation of AP2312-5 with AP2312-6 in the presence of dioxane, $^t$BuOH and $^t$BuOK (1.15 eq) to yield AP2312-8; and

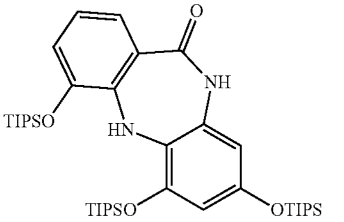

AP2312-5

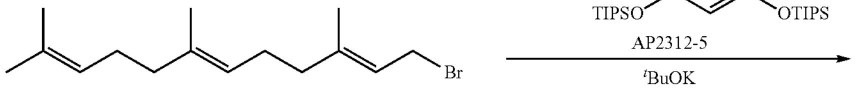

AP2312-6

$^t$BuOK

Dioxane/t-BuOH

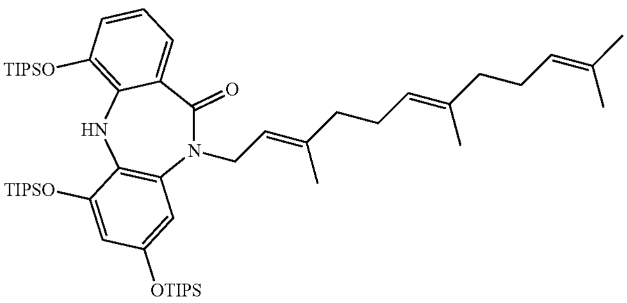

AP2312-8

(h) performing de-silylation of AP2312-8 in the presence of THF (1.0 eq), AcOH (8.0 eq) and TBAF (4.0 eq) to yield AMO-01

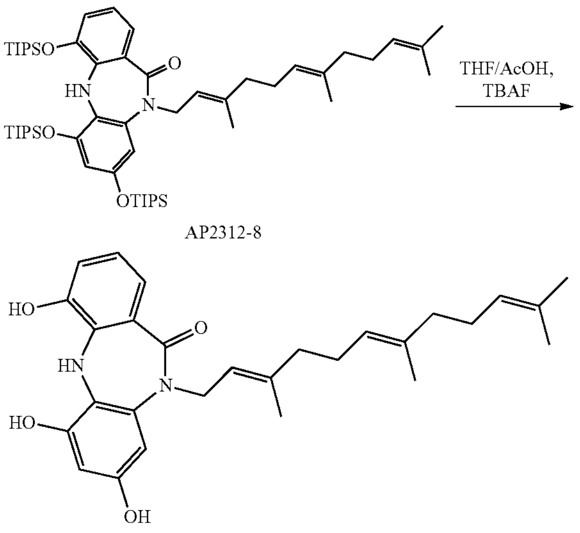

AP2312-8

AP2312 (AMO-01)

The foregoing has outlined rather broadly the features and technical advantages of the present invention in order that the detailed description of the invention that follows may be better understood. Additional features and advantages of the invention will be described herein, which form the subject matter of the claims of the invention. It should be appreciated by those skilled in the art that any conception and specific embodiment disclosed herein may be readily utilized as a basis for modifying or designing other means for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits of the invention.

DETAILED DESCRIPTION OF THE INVENTION

I. Definitions

Figure 1:
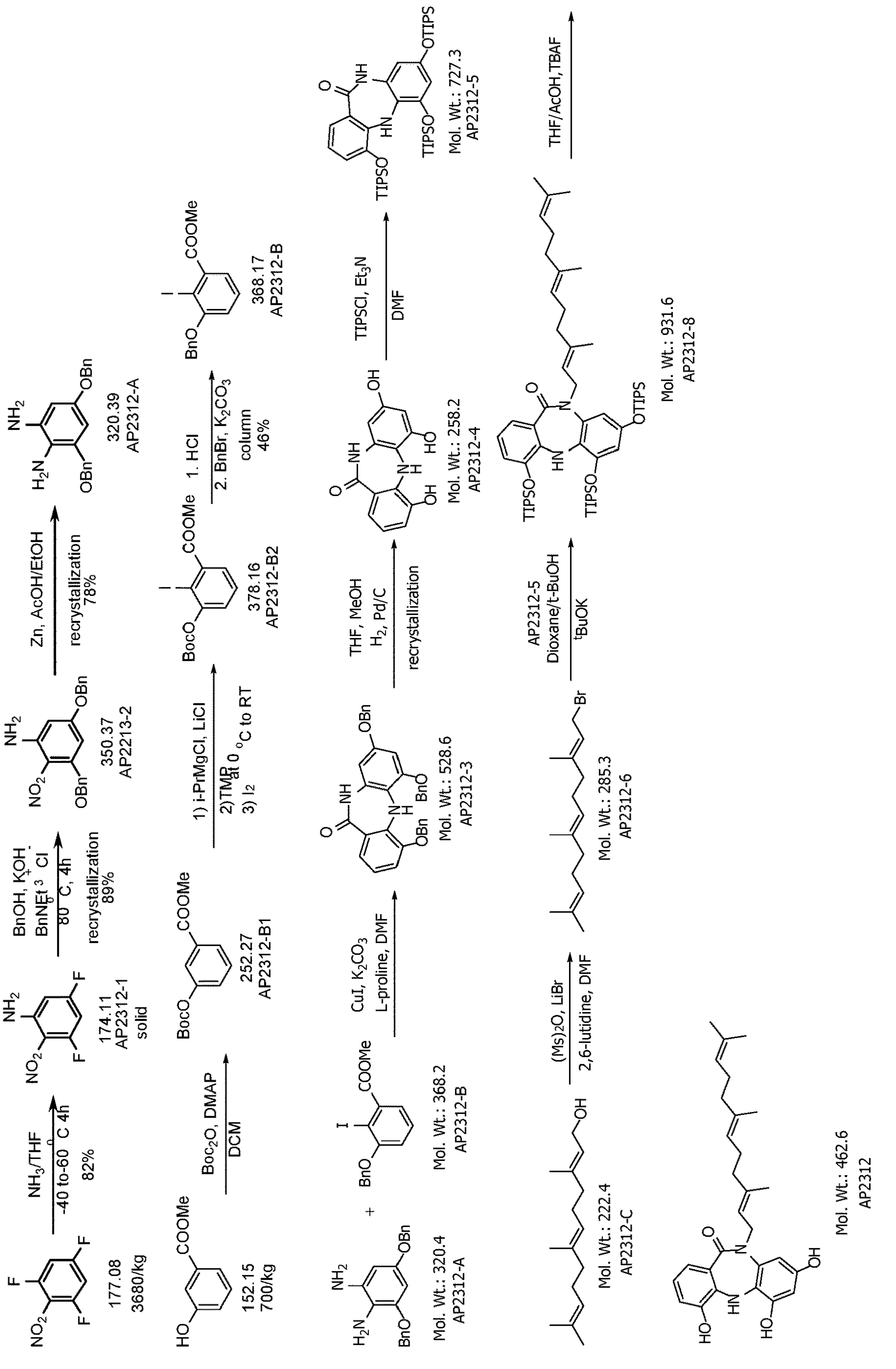
FIG. 1. General scheme for method of synthesizing the farnesyl dibenzodiazepinone AMO-01 (10-farnesyl-4,6,8-trihydroxy-dibenzodiazepin-11-one).

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. Farnesyl Dibenzodiazepinone Compounds

AMO-01 (10-farnesyl-4,6,8-trihydroxy-dibenzodiazepin-11-one; also termed "AP2312" herein) is a farnesyl dibenzodiazepinone and a member of a class of dibenzodiazepinone compounds containing a farnesyl moiety. The structure of AMO-01 is as follows:

AMO-01

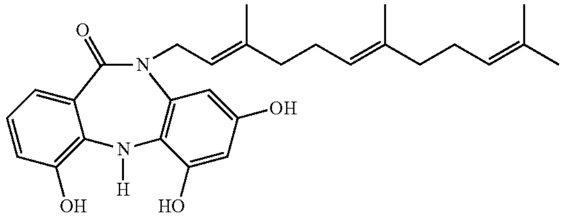

Farnesyl dibenzodiazepinone compounds may be produced by biologic means via culturing certain strains of *Micromonospora*, a genus of bacteria of the family Micromonosporaceae that are gram-positive, spore-forming, generally aerobic, and that form a branched mycelium, and then isolating the compound from the culture media. Members of the genus also commonly produce aminoglycoside antibiotics.

AMO-01 is produced by *Micromonospora* sp. strain 046-ECO11. Strain 046-ECO11 was deposited on Mar. 7, 2003, with the International Depositary Authority of Canada (IDAC), Bureau of Microbiology, Health Canada, 1015 Arlington Street, Winnipeg, Manitoba, Canada R3E 3R2, under Accession No. 070303-01. More details on strain 046-ECO11 and biologic means for producing AMO-01 may be found in international patent publication WO 2004/065591, published Aug. 5, 2004, the contents of which are incorporated herein by reference in their entirety.

Through the diligent efforts of the inventors, fully synthetic means for the production of farnesyl dibenzodiazepinone compounds, including AMO-01, have been realized. The present invention is directed to such means, along with related aspects of the invention disclosed herein.

Thus, and in one embodiment, the present invention is directed to methods of synthesizing the group of farnesyl dibenzodiazepinones of Formula I, as well as salts thereof:

Formula I

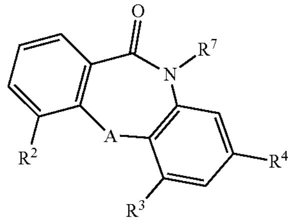

wherein,

A is —NH—;

$R^7$ is $—CH_3$, $—(CH_2)—CH_3$, $—CH_2CH_2W^1CH_3$, $—CH_2CH_2W^1CH_2CH_2W^2CH_3$ or $—CH_2W^1CH_2CH_2W^2CH_2CH_2W^3CH_3$, where x is an integer of from 1 to 11, and where each of $W^1$, $W^2$ and $W^3$ is independently

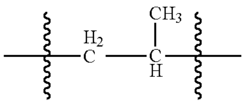

or

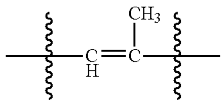

;

$R^2$ is —H, —OH, $—OCH_3$ or $—OP{=}O(OR^8)$, where $R^8$ is —Na, $—CH_3$ or $—CH_2CH_3$; and $R^3$ and $R^4$ are the same and selected from —H, —OH, $—OCH_3$ or $—OP{=}O(OR^8)$, where $R^8$ is —Na, $—CH_3$ or $—CH_2CH_3$. In certain aspects, the method is via the Ullmann reaction.

The method of synthesizing farnesyl dibenzodiazepinones of Formula I comprises the following steps, wherein A, $R^2$, $R^3$, $R^4$, $R^7$, $R^8$, $W^1$, $W^2$, $W^3$ and x are as defined above for Formula I:

(a) preparing AP2312-A;

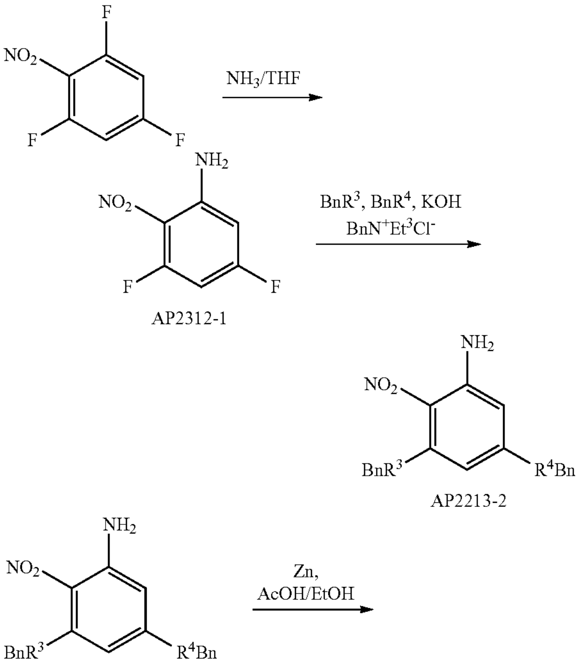

AP2312-1

AP2213-2

AP2213-2

-continued

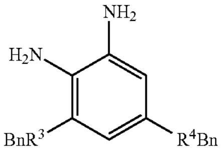

AP2312-A (b) preparing AP2312-B;

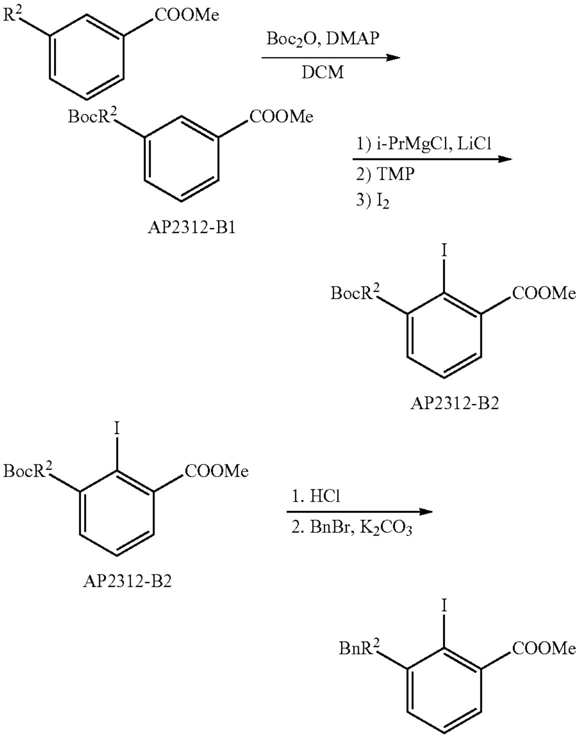

AP2312-B1

AP2312-B2

AP2312-B2

AP2312-B (c) performing Ullmann coupling;

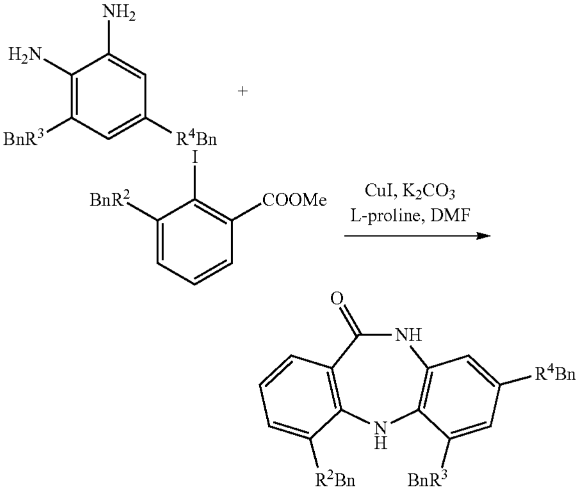

(d) performing de-benzylation;

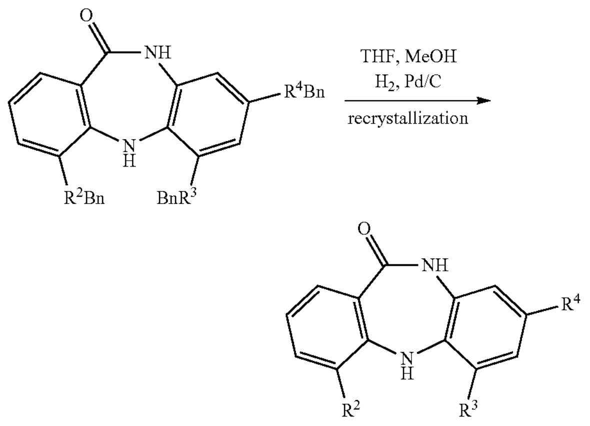

(e) performing silylation;

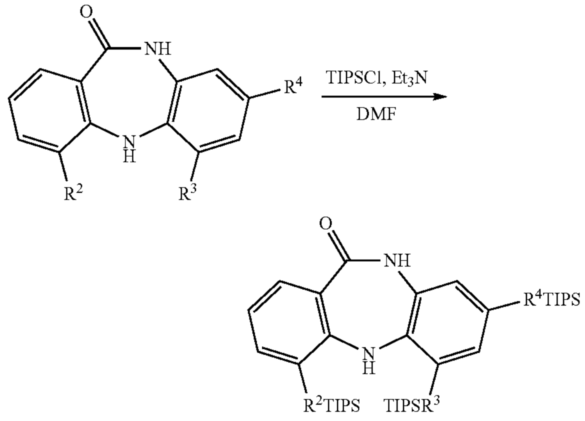

(f) preparing $R^7$;

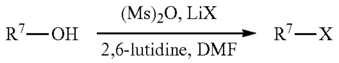

wherein X is Br, I, or Cl (g) performing farnesylation; and

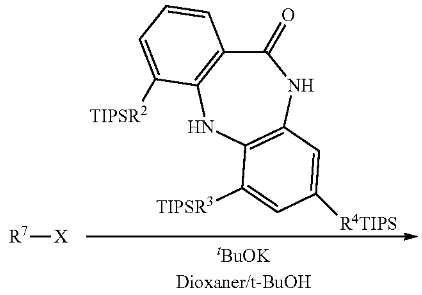

-continued

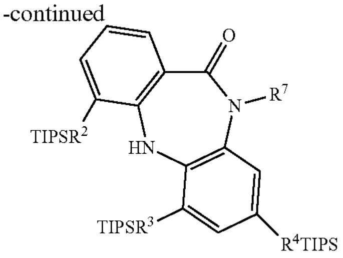

(h) performing de-silylation

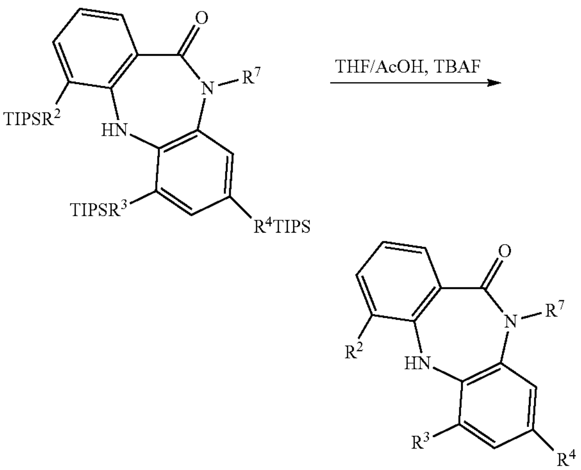

The present invention is also directed to methods of synthesizing the group of farnesyl dibenzodiazepinones of Formula II, as well as salts thereof:

Formula II

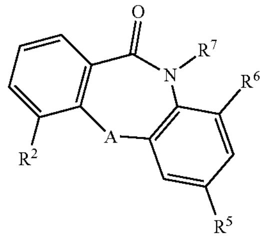

wherein,

A is —NH—;

$R^7$ is —$CH_3$, —$(CH_2)_xCH_3$, —$CH_2CH_2W^1CH_3$, —$CH_2CH_2W^1CH_2CH_2W^2CH_3$ or —$CH_2W^1CH_2CH_2W^2CH_2CH_2W^3CH_3$, where x is an integer of from 1 to 11, and where each of $W^1$, $W^2$ and $W^3$ is independently

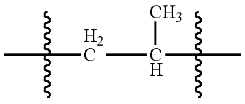 or 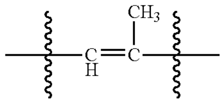 ;

$R^2$ is —H, —OH, —$OCH_3$ or —OP═O($OR^8$), where $R^8$ is —Na, —$CH_3$ or —$CH_2CH_3$; and $R^5$ and $R^6$ are the same and selected from —H, —OH, —$OCH_3$ or —OP═O($OR^8$), where $R^8$ is —Na, —$CH_3$ or —$CH_2CH_3$. In certain aspects, the method is via Buchwald coupling.

The method of synthesizing farnesyl dibenzodiazepinones of Formula II comprises the following steps, wherein A, $R^2$, $R^5$, $R^6$, $R^7$, $R^8$, $W^1$, $W^2$, $W^3$ and x are as defined above for Formula II:

(a) preparing AP2312-A;

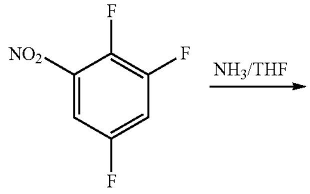

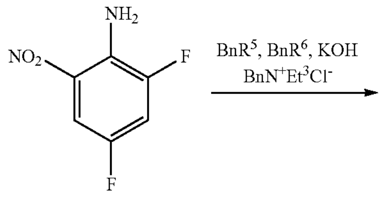

AP2312-1

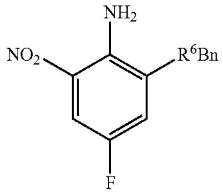

AP2213-3

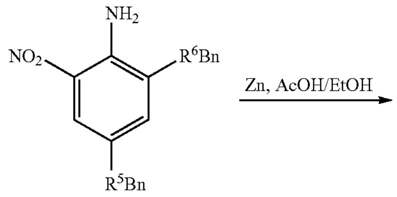

AP2213-3

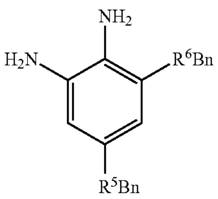

AP2312-A (b) preparing AP2312-B;

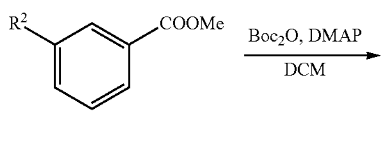

-continued

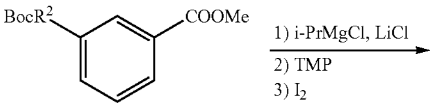

AP2312-B1

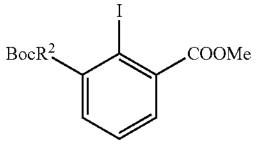

AP2312-B2

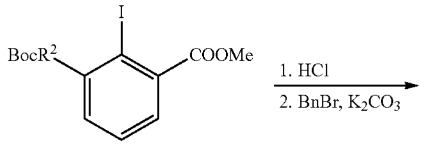

AP2312-B2

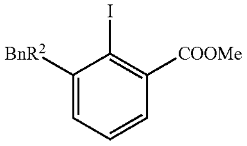

AP2312-B (c) performing Buchwald coupling;

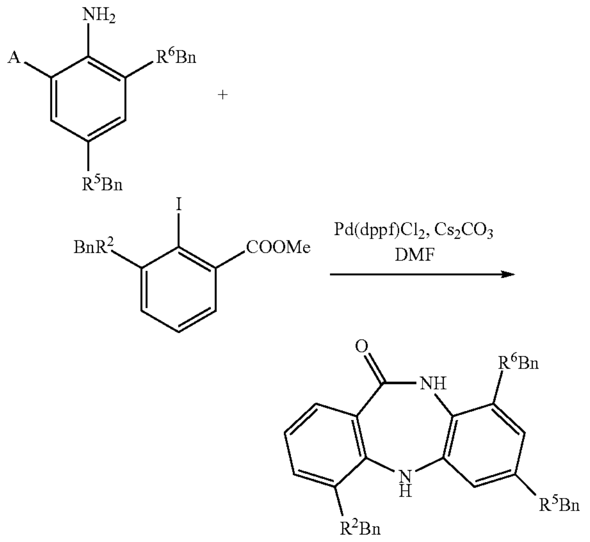

(d) performing de-benzylation;

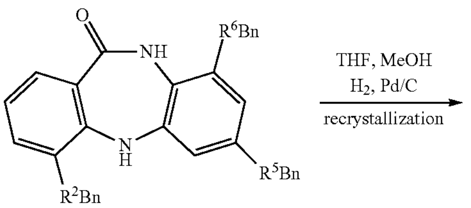

-continued
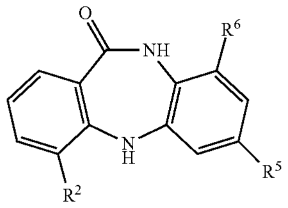
(e) performing silylation;
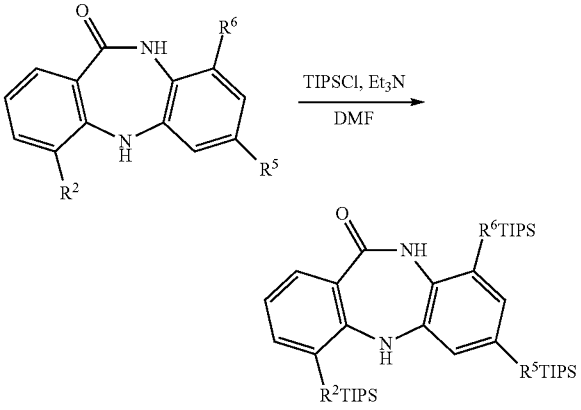
(f) preparing $R^7$;
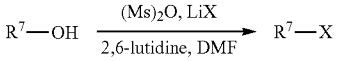
wherein X is Br, I, or Cl
(g) performing farnesylation; and
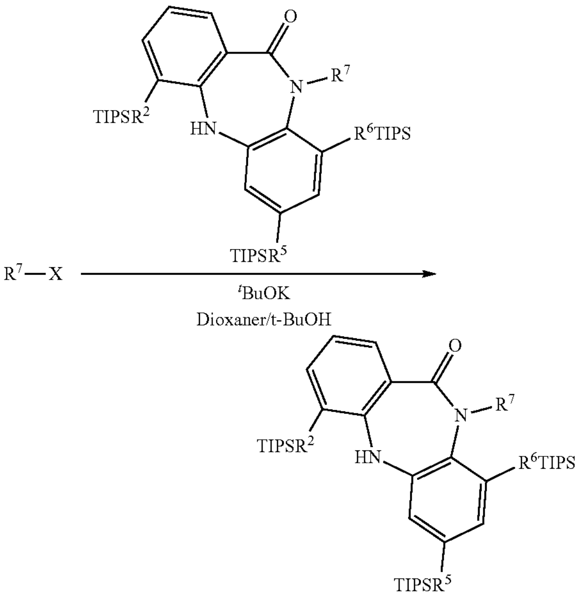
(h) performing de-silylation
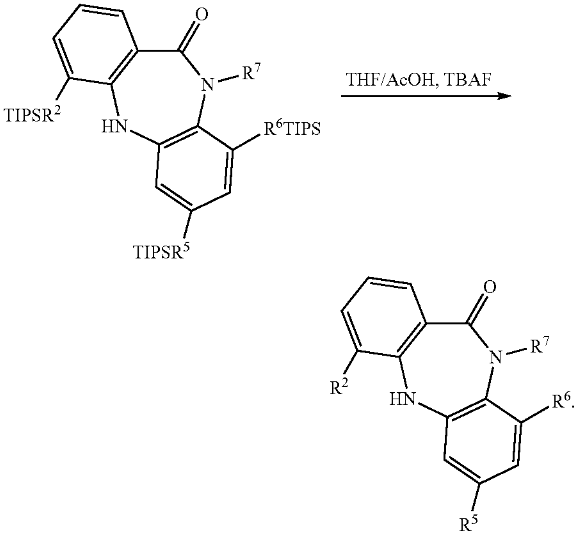
The present invention is also directed to methods of synthesizing the farnesyl dibenzodiazepinone AMO-01
AMO-01
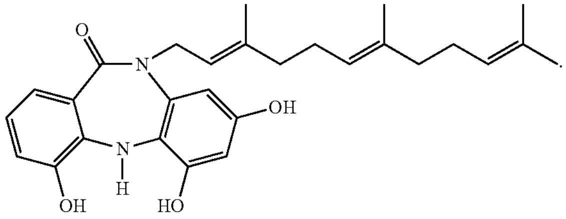
In certain aspects, the method comprises the following steps:
(a) preparing AP2312-A;
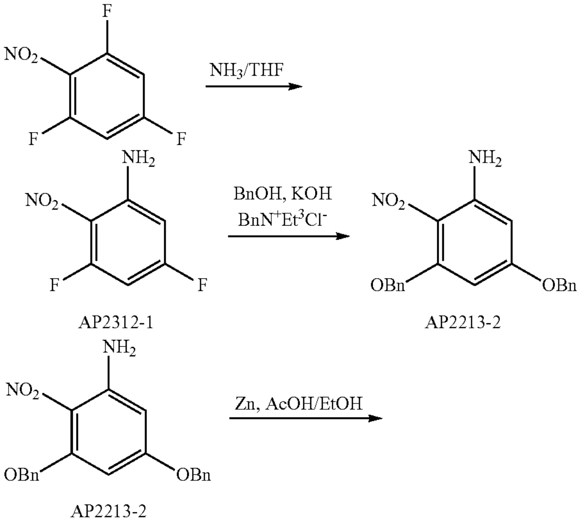

-continued
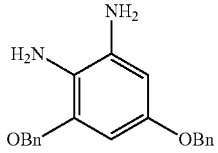
AP2312-A
(b) preparing AP2312-B;
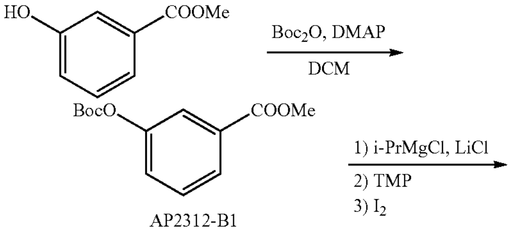
AP2312-B1
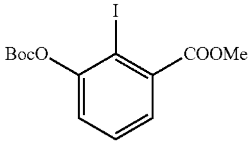
AP2312-B2
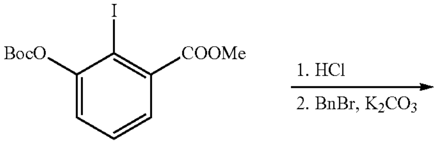
AP2312-B2
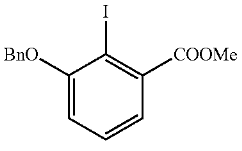
AP2312-B
(c) performing Ullmann coupling;
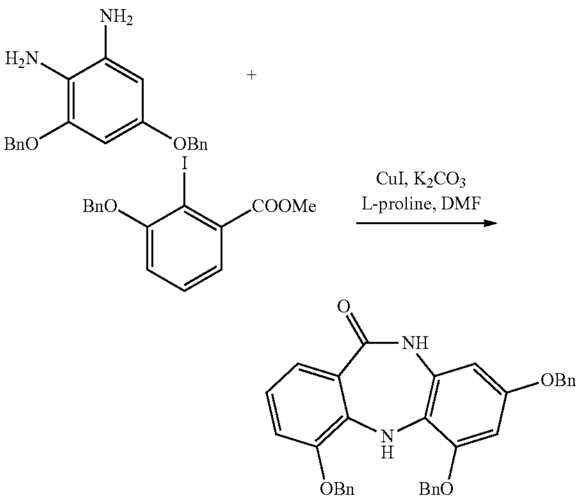
(d) performing de-benzylation;
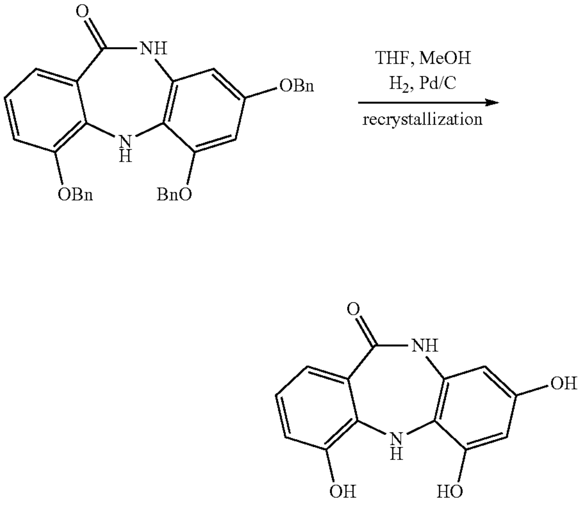
(e) performing silylation;
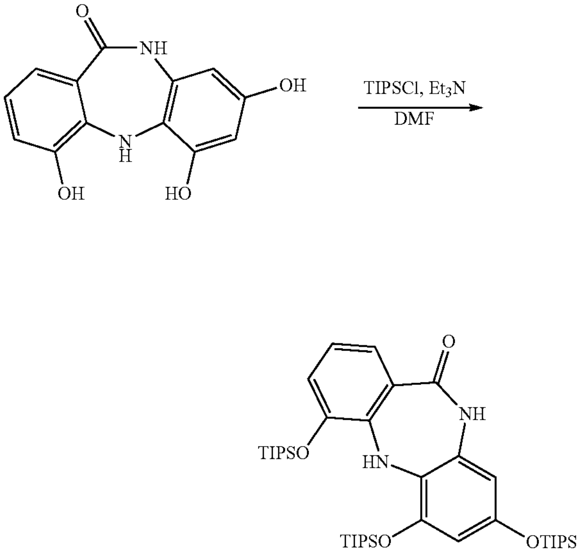
(f) preparing farnesyl bromide;
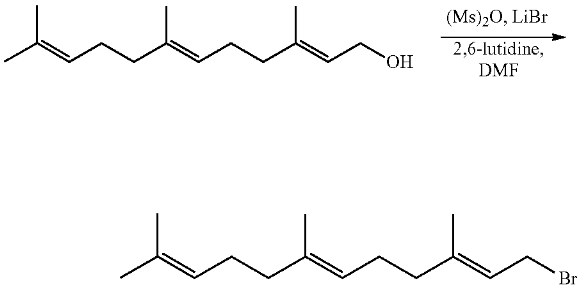

(g) performing farnesylation; and
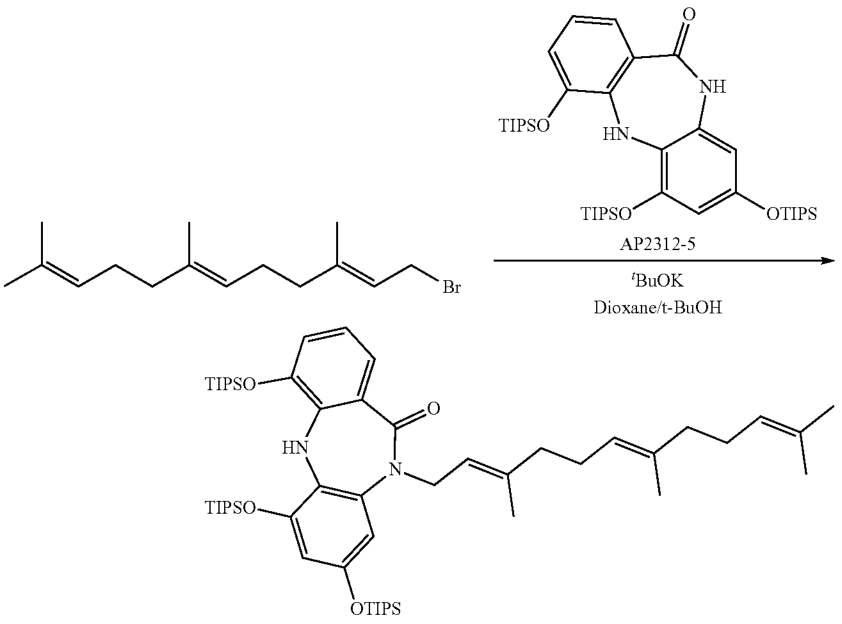
(h) performing de-silylation
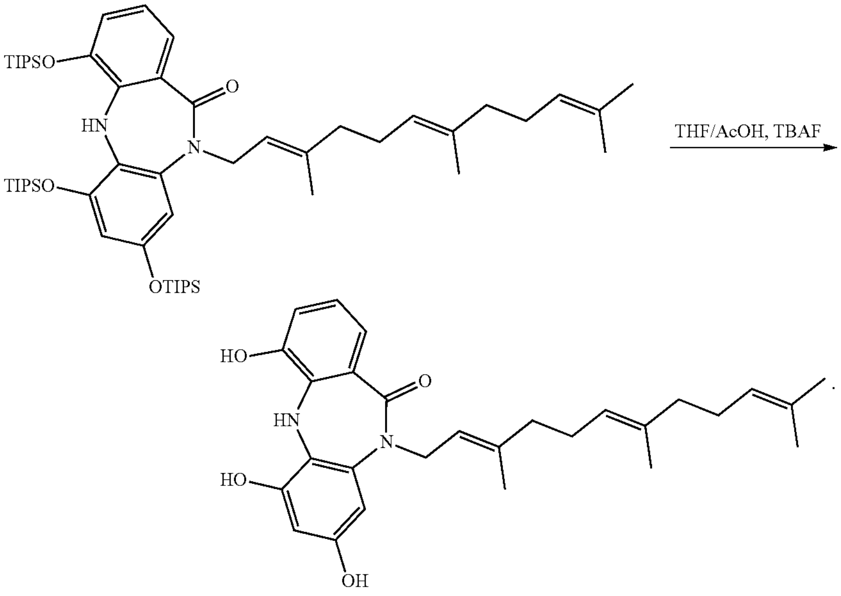
In a specific aspect, the method of synthesizing AMO-01 comprises the following steps:
(a) preparing AP2312-A;
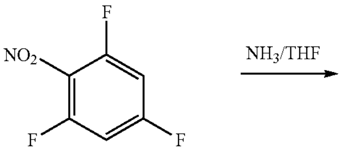
-continued
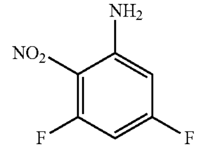
AP2312-1
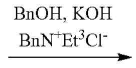

-continued

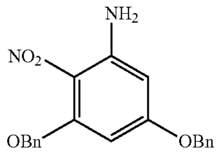

AP2213-2

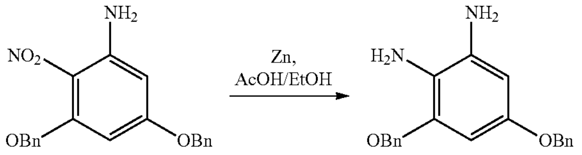

AP2213-2 AP2312-A (b) preparing AP2312-B;

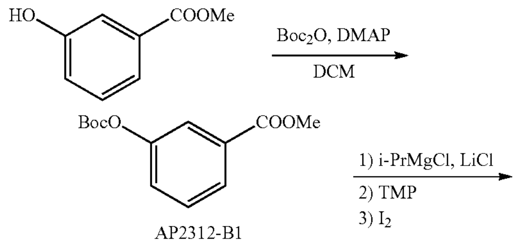

AP2312-B1

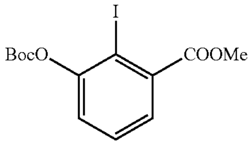

AP2312-B2

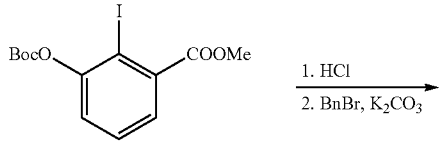

AP2312-B2

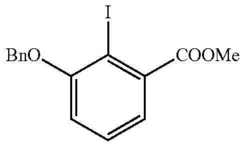

AP2312-B (c) performing Ullmann coupling by reacting molecular equivalent amounts of AP2312-A and AP2312-B in the presence of CuI (0.0525 eq), $K_2CO_3$ (2.0 eq), L-proline (0.1 eq) and DMF to yield AP2312-3;

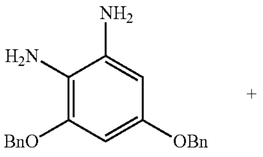

AP2312-A

-continued

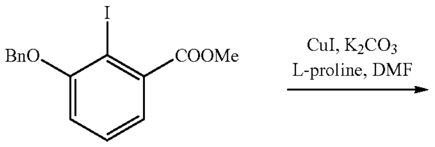

AP2312-B

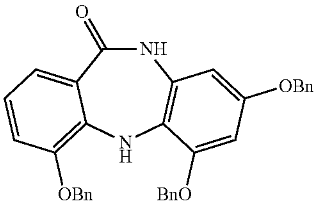

AP2312-3

(d) performing de-benzylation of AP2312-3 in the presence of THF, MeOH and Pd/C under $H_2$ to yield AP2312-4;

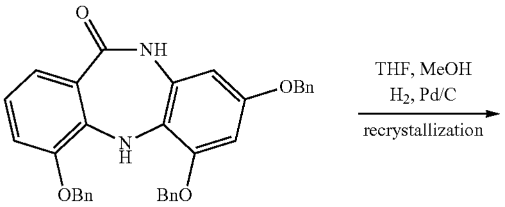

AP2312-3

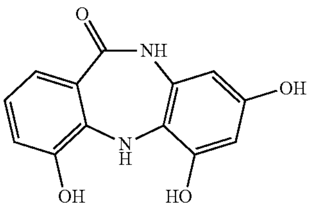

AP2312-4

(e) performing silylation of AP2312-4 in the presence of TIPSCl (4.0 eq) $Et_3N$ (5.0 eq) and DMF to yield AP2312-5;

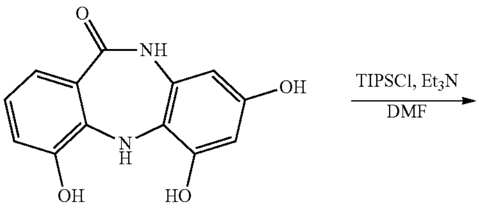

AP2312-4

-continued
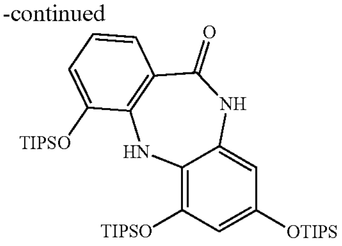
AP2312-5
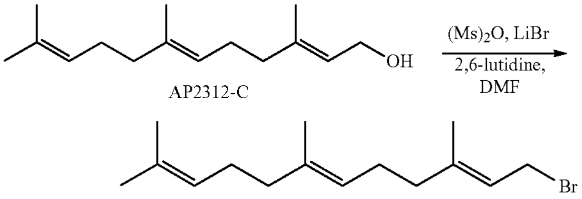
AP2312-C
AP2312-6
(f) reacting AP23132-C in the presence of $Ms_2O$, LiBr (1.6 eq), 2,6-lutidine (1.6 eq) and DMF to yield AP2312-6;
(g) performing farnesylation of AP2312-5 with AP2312-6 in the presence of dioxane, $^t$BuOH and $^t$BuOK (1.15 eq) to yield AP2312-8; and
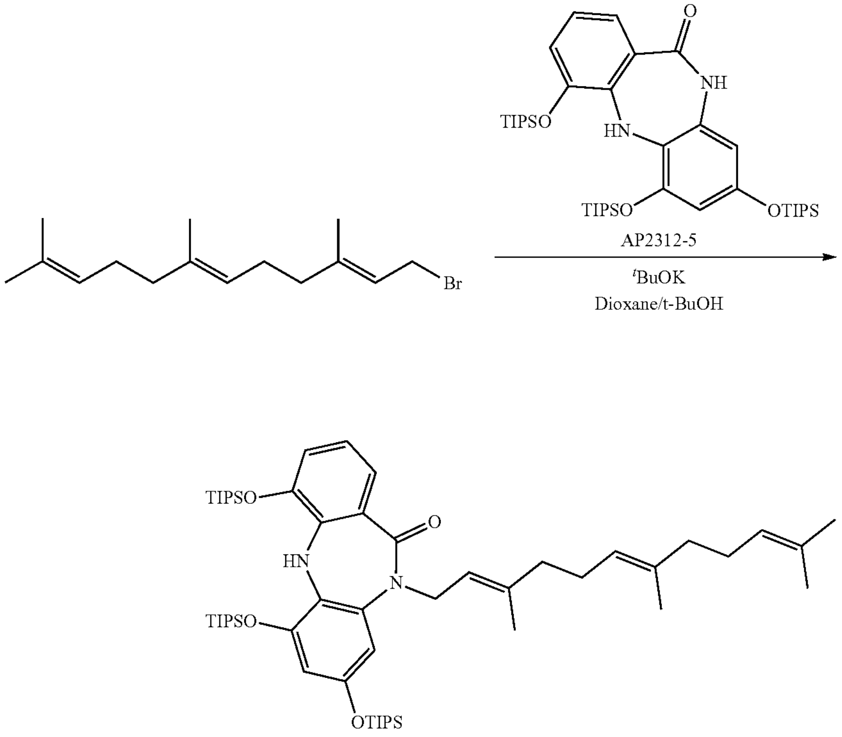
AP2312-5
(h) performing de-silylation of AP2312-8 in the presence of THF (1.0 eq), AcOH (8.0 eq) and TBAF (4.0 eq) to yield AMO-01
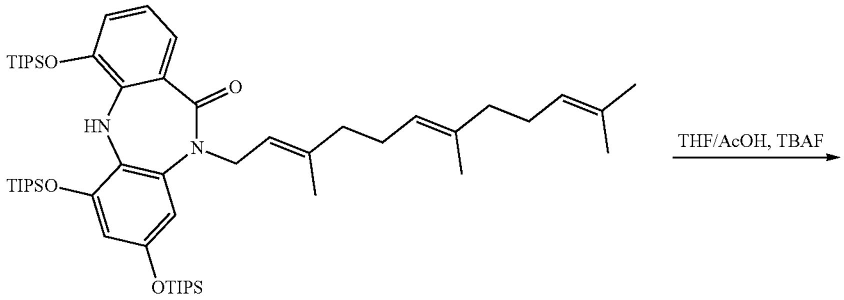
AP2312-8

-continued
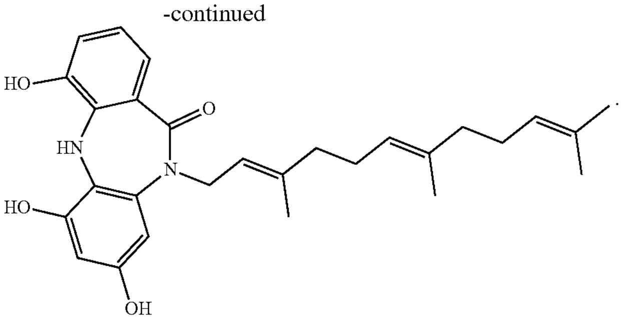
AMO-01
The following are exemplary compounds and specific examples of the farnesyl dibenzodiazepinone compounds that may be produced via the methods of the invention as defined herein:
Formula VII
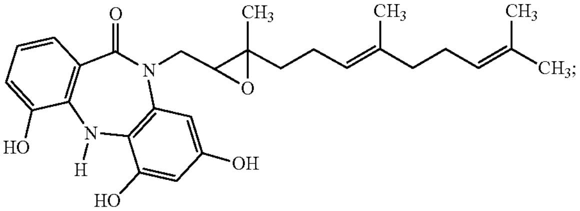
Formula VIII
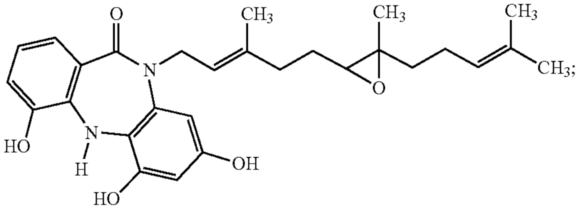
Formula VIX
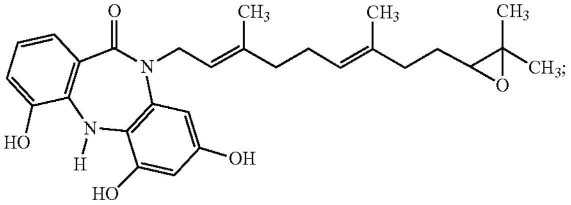
Formula X
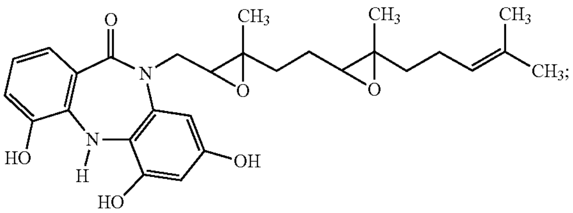
-continued
Formula XI
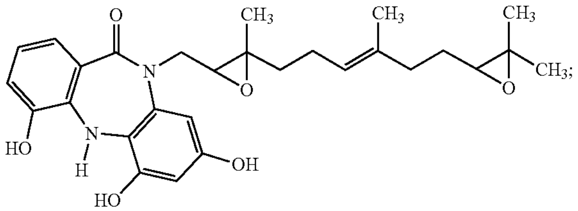
Formula XII
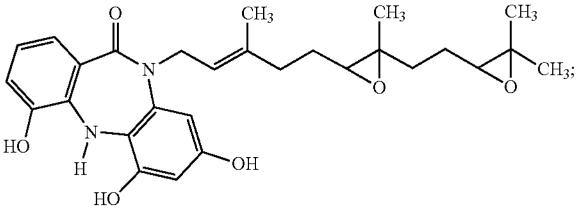
Formula XIII
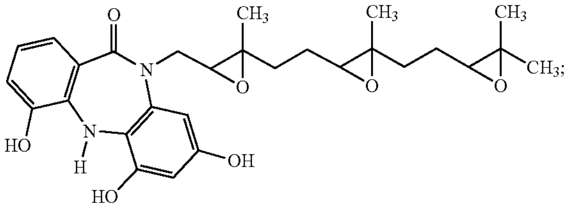
Formula XIV
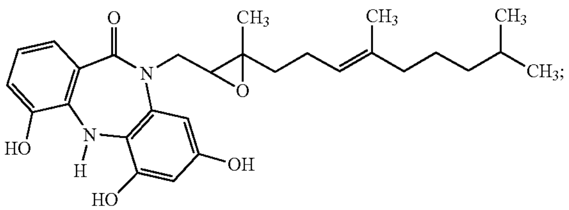
Formula XV
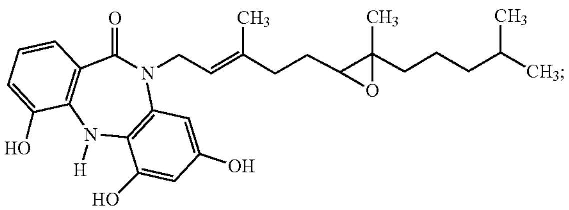

-continued
Formula XVI
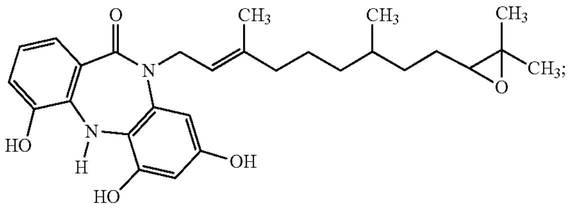
Formula XVII
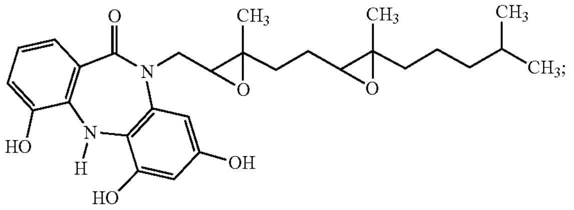
Formula XVIII
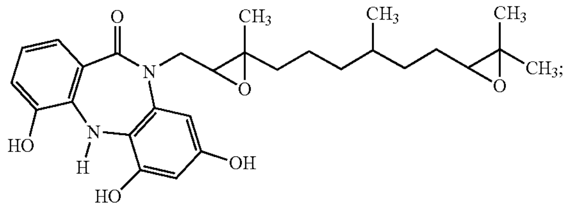
Formula XIX
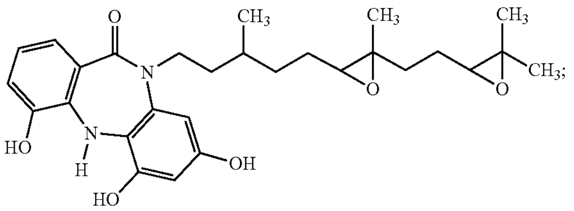
Formula XX
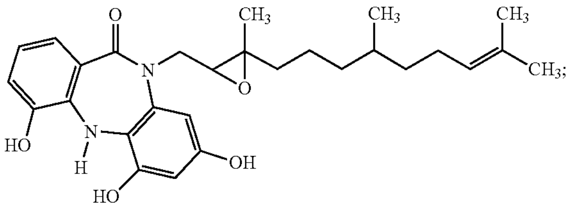
Formula XXI
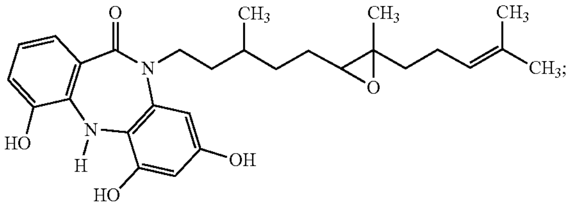
Formula XXII
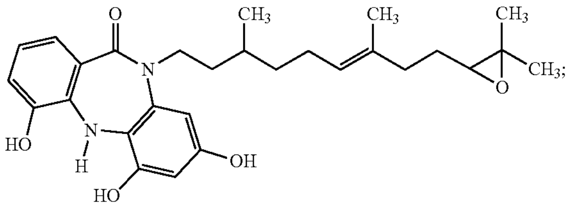
-continued
Formula XXIII
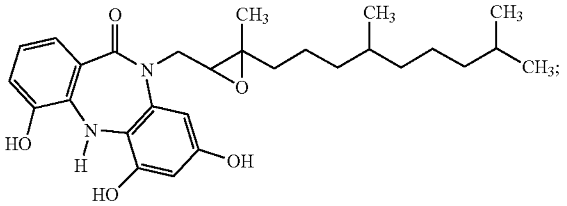
Formula XXIV
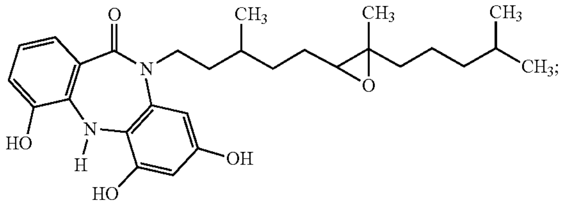
Formula XXV
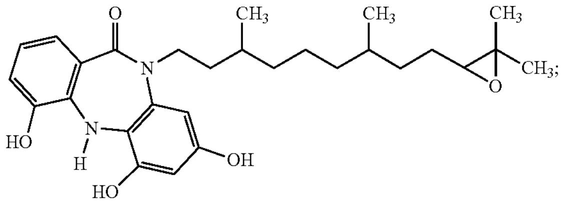
Formula XXVI
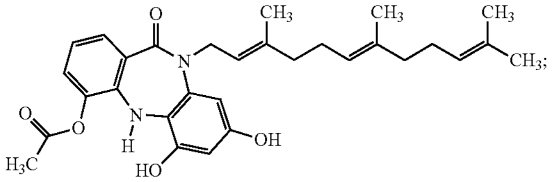
Formula XXVII
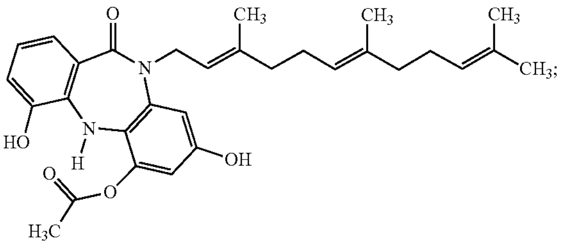
Formula XXVIII
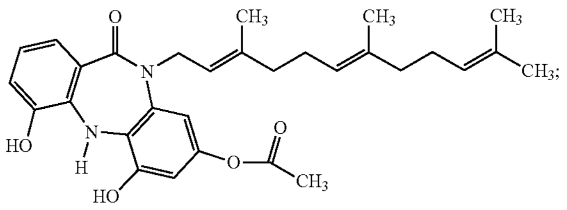

-continued
Formula XXIX
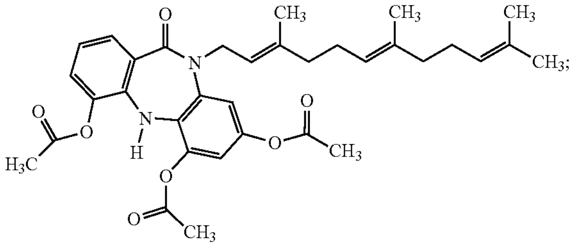
Formula XXX
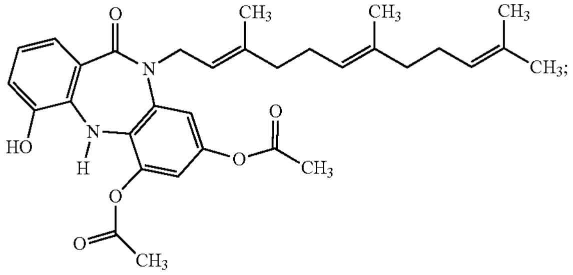
Formula XXXI
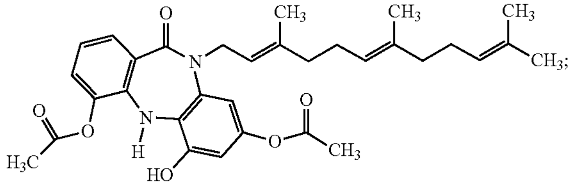
Formula XXXII
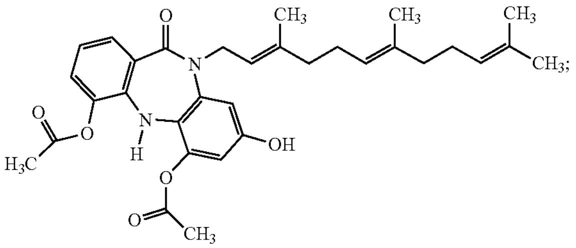
Formula XXXIII
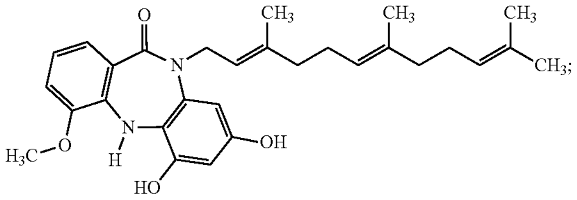
Formula XXXIV
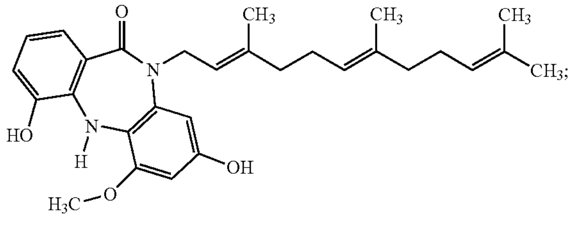
-continued
Formula XXXV
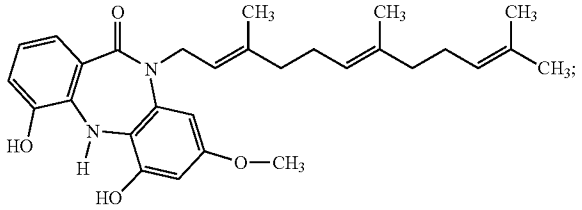
Formula XXXVI
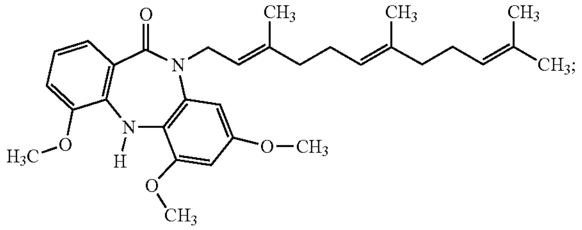
Formula XXXVII
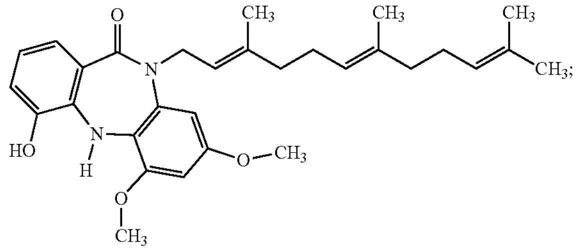
Formula XXXVIII
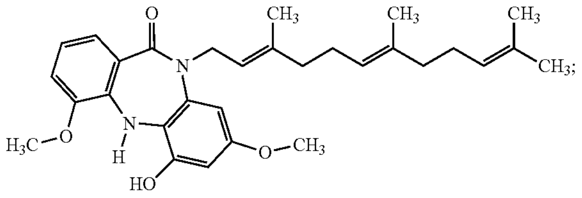
Formula XXXIX
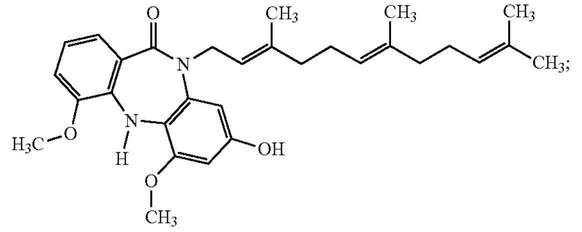
Formula XL
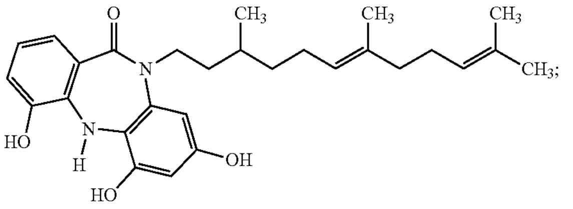

-continued
Formula XLI
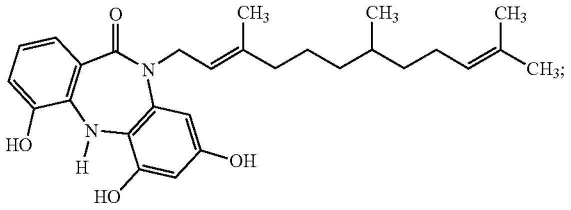
Formula XLII
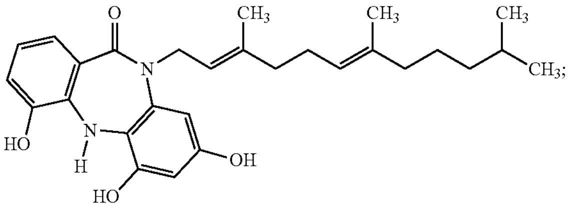
Formula XLIII
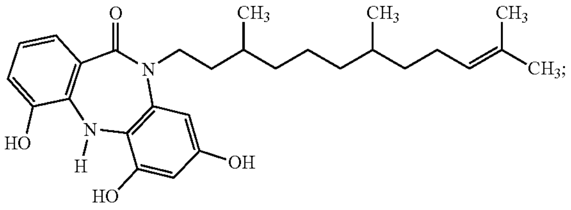
Formula XLIV
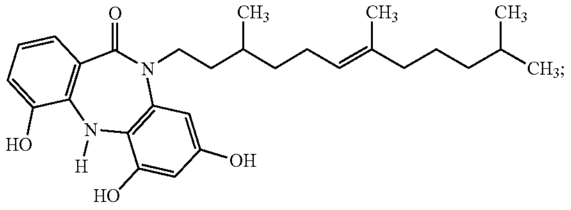
Formula XLV
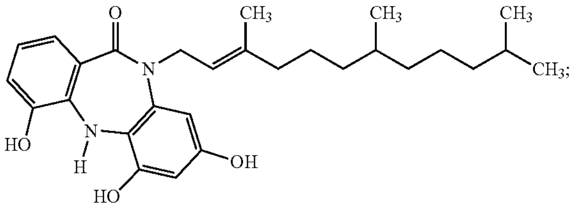
Formula XLVI
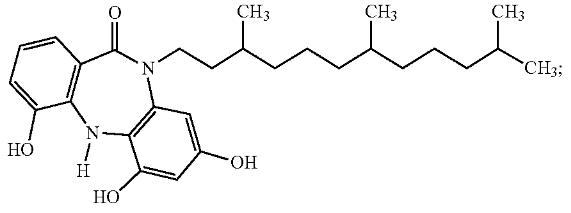
-continued
Formula XLVII
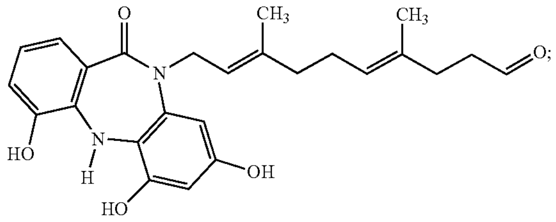
Formula XLVIII
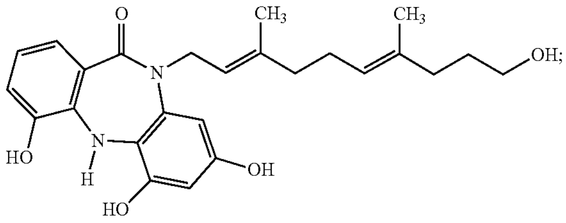
Formula XLIX
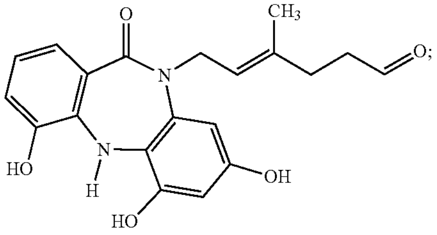
Formula L
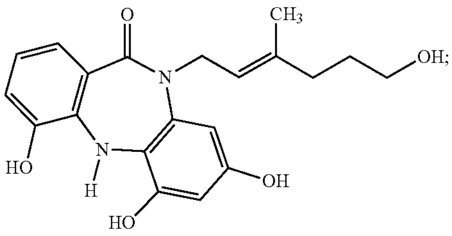
Formula LI
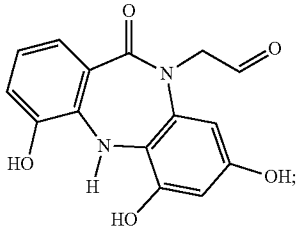
Formula LII
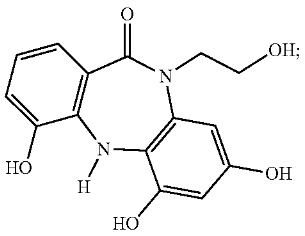

-continued

Formula LIII

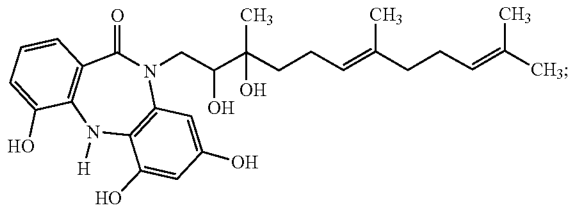

Formula LIV

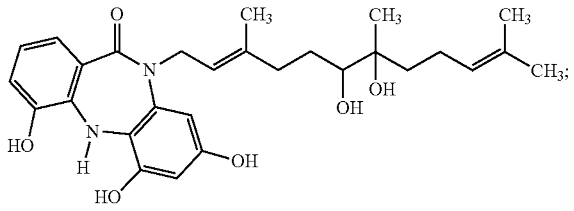

Formula LV

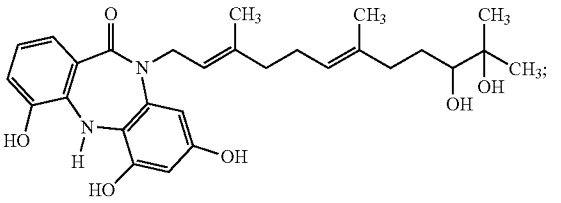

Formula LVI

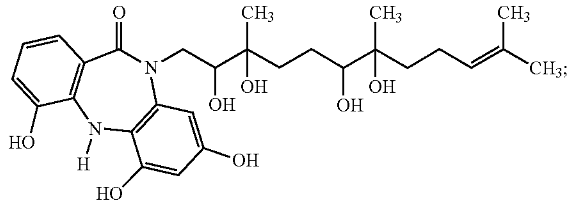

Formula LVII

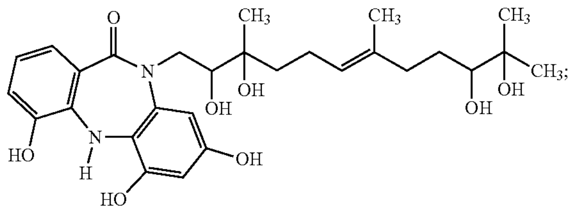

Formula LVIII

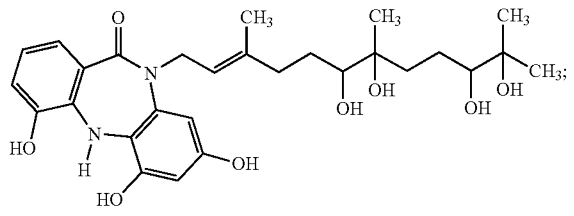

and

-continued

Formula LIX

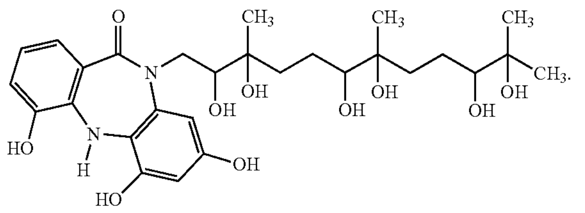

With reference to variable "x" as an integer in the formula of the invention, it should be understood that x is an integer of 1, 2, 3, 4, 5, 6, 7, 8, 9, 10 or 11. The integer x may range from 1 to 11, from 1 to 10, from 1 to 9, from 1 to 8, from 1 to 7, from 1 to 6, from 1 to 5, from 1 to 4, from 1 to 3, and from 1 to 2. To avoid any doubt, the ranges include both of the endpoints as integers in the range.

As used herein, the term "alkyl" refers to linear or branched hydrocarbon groups. Examples of alkyl groups include, without limitation, methyl, ethyl, n-propyl, isopropyl, n-butyl, pentyl, hexyl, heptyl, cyclopentyl, cyclohexyl, cyclohexymethyl, and the like. Alkyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, oxo, guanidino and formyl. The number of carbons in the hydrocarbon groups may range from 1-6 carbon atoms, and includes 1-2 carbon atoms, 1-3 carbon atoms, 1-4 carbon atoms and 1-5 carbon atoms.

As used herein, the term "alkene" refers to unsaturated hydrocarbon groups that contains a carbon-carbon double bond. The number of carbons in the hydrocarbon groups may range from 2-6 carbon atoms, and includes 2 carbon atoms, 2-3 carbon atoms, 2-4 carbon atoms and 2-5 carbon atoms.

As used herein, the terms "aryl" and "aryl ring" refer to aromatic groups in a single or fused ring system, having 5, 6, 7, 8, 9, 10, 11, 12, 13, 14 or 15 ring members. Examples of aryl include, without limitation, phenyl, naphthyl, biphenyl, terphenyl. Aryl may optionally be substituted with one or more substituent group selected from acyl, amino, acylamino, acyloxy, azido, alkythio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

As used herein, the terms "heteroaryl" and "heteroaryl ring" refer to aromatic groups in a single or fused ring system, having 5, 6, 7, 8, 9, 10, 11, 12, 13, 14 or 15 ring members and containing at least one hetero atom selected from O, N, S, SO and $SO_2$. Examples of heteroaryl groups include, without limitation, pyridinyl, thiazolyl, thiadiazoyl, isoquinolinyl, pyrazolyl, oxazolyl, oxadiazoyl, triazolyl, and pyrrolyl groups. Heteroaryl groups may optionally be substituted with one or more substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, and formyl.

The term "alkenyl" refers to linear, branched or cyclic hydrocarbon groups containing at least one carbon-carbon double bond. Examples of alkenyl groups include, without limitation, vinyl, 1-propen-2-yl, 1-buten-4-yl, 2-buten-4-yl, 1-penten-5-yl and the like. Alkenyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration.

The terms "cycloalkyl" and "cycloalkyl ring" refer to a saturated or partially unsaturated carbocyclic ring in a single or fused carbocyclic ring system having 3, 4, 5, 6, 7, 8, 9, 10, 11, 12, 13, 14 or 15 ring members. Examples of cycloalkyl groups include, without limitation, cyclopropyl, cyclobutyl, cyclohexyl, and cycloheptyl. Cycloalkyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The terms "heterocyclyl" and "heterocyclic" refer to a saturated or partially unsaturated ring containing 1, 2, 3, or 4 hetero atoms or hetero groups selected from O, N, NH, NRx, $PO_2$, S, SO or SO in a single or fused heterocyclic ring system having 3, 4, 5, 6, 7, 8, 9, 10, 11, 12, 13, 14 or 15 ring members. Examples of a heterocyclyl or heterocyclic ring include, without limitation, morpholinyl, piperidinyl, and pyrrolidinyl. Heterocyclyl, heterocyclic or heterocyclyl ring may optionally be substituted with substituents selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term "amino acid" refers to any natural amino acid, such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

The term "halo" refers to a halogen atom, e.g., bromine, chlorine, fluorine and iodine.

The terms "aralkyl" and "heteroaralkyl" refer to an aryl group or a heteroaryl group, respectively bonded directly through an alkyl group, such as benzyl. Aralkyl and heteroaralkyl may be optionally substituted as the aryl and heteroaryl groups.

Similarly, the terms "aralkenyl" and "heteroaralkenyl" refer to an aryl group or a heteroaryl group, respectively bonded directly through an alkene group, such as benzyl. Aralkenyl and heteroaralkenyl may be optionally substituted as the aryl and heteroaryl groups.

The compounds of the present invention can possess one or more asymmetric carbon atoms and can exist as optical isomers forming mixtures of racemic or non-racemic compounds. The compounds of the present invention are useful as single isomers or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes.

III. Methods of Synthesis

As summarized above, the invention is drawn to methods of synthesizing farnesyl dibenzodiazepinones compounds of Formula I and Formula II, as defined herein. The reaction schemes for compounds encompassed by these Formula are provided herein. Initial experiments used in the production of farnesyl dibenzodiazepinones compounds of the invention resulted in the surprising finding that by using Buchwald coupling, compounds of Formula II were realized, while use of Ullmann coupling resulted in the compounds of Formula I. Thus, while the initial steps in the synthesis of compounds of Formula I and Formula II are similar, the choice of Ullmann coupling versus Buchwald coupling drives the rejection to produce compounds of Formula I and Formula II, respectively.

AMO-01

In a specific embodiment, the invention is drawn to a method of synthesizing the farnesyl dibenzodiazepinone AMO-01 (10-farnesyl-4,6,8-trihydroxy-dibenzodiazepin-11-one). While the details regarding the method are provided in following paragraphs, the general scheme can be seen in FIG. 1. AMO-01 is referred to as AP2312 in the example.

In Step 1 of the method for synthesizing AMO-01, AP2312-A is prepared as follows:

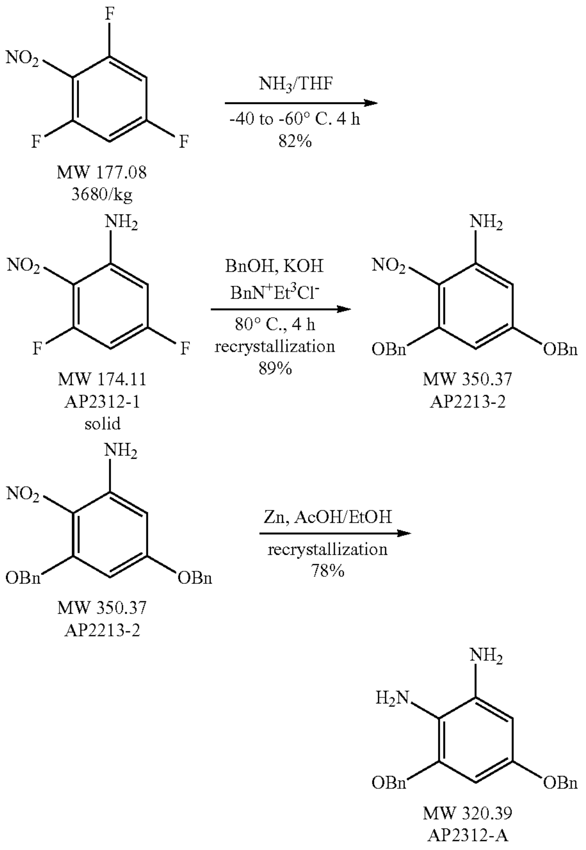

The preparation of AP2312-A was achieved via two alternative, highly related schemes. The first scheme included Steps 1.A, 1.B and 1.C.

Step 1.A—To a solution of 1,3,5-trifluoro-2-nitrobenzene (490.0 g, 2.77 moL) in THF (2.45 L) was bubbled ammonia gas (~240 g, 14.1 moL) at −60~−40° C. over 2 h. After stirring at 0° C. for 4 h, the reaction mixture was filtered and the filter cake was washed with EtOAc (490 mL×4). The filtrate was concentrated to ~500 mL and added petroleum ether (980 mL). The mixture was reslurrying at RT for overnight, filtered and the filter cake was washed with petroleum ether (490 mL). The filter cake was dried at 40°

C. under vacuum for 5 h to afford 366 g of AP2312-1 as orange solid, 76% yield, 98.0% pure by HPLC.

Step 1.B—A mixture of KOH (151 g, 2.7 moL) and $BnEt_3N^+Cl^-$ (98 g, 0.43 moL) in BnOH (1045 g, 9.7 moL) was stirred at RT for 0.5 h. The reaction mixture was added AP2312-1 (188 g) in portions over 0.5 h and stirred at 80° C. for 3 h. After cooling to RT, the reaction mixture was poured into water (1.5 L), extracted with DCM (2.8 L). The organic layer was washed with water (1.5 L×2), dried over $Na_2SO_4$ (94 g), filtered and concentrated. The residue was reslurried in petroleum ether (3.8 L) at RT for 1 h, filtered and the filter cake was washed sequentially with petroleum ether (0.94 L×2) and MeOH (0.94 L×3). The filter cake was dried at 50° C. under vacuum for 6 h to afford 348 g of AP2312-2 as orange solid, 94% yield, 99.7% pure by HPLC.

Step 1.C—AP2312-2 (175.0 g, 0.5 moL) was suspended in EtOH (700 mL), $H_2O$ (350 mL) and AcOH (315 mL). To the reaction mixture was added zinc powder (110.5 g, 1.7 moL) in portions at RT. The reaction was highly exothermic and temperature rose to 80° C. in 1 h. The reaction mixture was stirred at 80° C. for 2 h. After cooling, the reaction mixture to room temperature, the inorganic salts were filtered off and the filter cake was washed with DCM (700 mL). The filtrate was concentrated to remove organic solvents and extracted with DCM (1.4 L). The organic layer was washed sequentially with water (700 mL), 3 M NaOH (350 mL×2) then water (700 mL). The organic layer was concentrated and was purified by reslurrying in EtOH (350 mL) at 0~15° C. for 1 h. The mixture was filtered and the filter cake was washed with chilled ethanol (175 mL). The filter cake was dried at 45° C. under vacuum for 7 h to afford 92.5 g of AP2312-A as yellow solid, 58% yield, 99.5% pure by HPLC.

The second scheme for preparing AP2312-A included Steps 1.1, 1.2 and 1.3:

Step 1.1

(1) Charged THF (5 L) to a 10-L four necked flask fitted with a mechanical stirrer
(2) Charged 1,3,5-trifluoro-2-nitrobenzene (1.0 kg) at RT
(3) Cooled the mixture to −60~−40° C. under a dry ice/EtOH bath with $N_2$ protection
(4) Introduced a flow of ammonia gas at −60~−40° C. for 1.5 hrs
Note: The volume of the reaction mixture increased, which showed that the $NH_3$ was absorbed. The $NH_3$ gas evolved was absorbed by 20% aqueous $H_2SO_4$
(5) After 2 h at −60~−40° C., LCMS showed that 22.2% of starting material remained
(6) Warmed the temperature to −15~−10°. Covered 2 h and stirred at −15~−10° C. overnight (16 h); LCMS showed that 0.5% starting material remained
(7) Warmed the mixture to 10° C.
Note: The $NH_3$ gas evolved was absorbed by 20% aqueous $H_2SO_4$
(8) Filtered the salt ($NH_4F$) under vacuum
(9) Washed the cake with EtOAc (500 mL×4)
Note: wet cake: 560 g; TLC showed no product was remained
(10) Another batch prepared using the same starting materials was prepared and combined
(11) Concentrated the combined filtrate under vacuum at RT for 0.5 h to remove the $NH_3$ gas
(12) Concentrated the filtrate under vacuum at 40-45° C. to a volume of 2 L
Note: copious yellow to red solid precipitated out
(13) Charged with n-heptane (1.6 L)
(14) Concentrated the mixture under vacuum at 40-45° C. to a volume of 2 L
(15) Charged n-heptane (1.0 L)
(16) Stirred the mixture at RT for 1 h with vigorous agitation
(17) Collected the solid by filtration
(18) Washed the cake with n-heptane (500 mL)
(19) Dried the cake under vacuum at 35-40° C. to afford 1350 g red solid, 96.7% pure by HPLC
(20) Concentrated the filtrate to a volume of 3 L
(21) Stirred it at RT for 0.5 h
(22) Collected the solid by filtration
(23) Washed the cake with n-heptane (100 mL)
(24) Dried the cake under vacuum at 35-40° C. to give another 390 g red solid, 93.1% pure by HPLC
(25) Total yield: 1700 g, 82%

Step 1.2

(26) Charged BnOH (9732.6 g) to a 50-L reactor
(27) Charged KOH (1402.7 g) with stirring (150 RPM)
(28) Charged $BnEt_3NCl$ (956.63 g)
(29) Cooled the mixture to 15° C. with $N_2$ protection
(30) Charged AP2312-1 (1740.0 g) portionwise
(31) Warmed the mixture to 75-80° C. for 4 h
HPLC indicated that <1.0% (0.11%) starting material remained
(32) Cooled the mixture to RT
(33) Charged DCM (17 L in one portion)
(34) Charged water (14 L in one portion)
(35) Stirred the mixture for 30 min
(36) Isolated the organic layer
(37) Washed the organic layer with water (9 L)
(38) Dried the solution over $Na_2SO_4$ (2 kg)
(39) Filtered off the salt
(40) Concentrated the filtrate at 35-40° C. to ~13 L
Note: Orange solid precipitated out and almost no distillate was observed
(41) Charged PE (37 L)
(42) Stirred the slurry at RT for 1.5 h
(43) Collected the solid by filtration
(44) Washed the cake with MeOH (4 L×2)
(45) Washed the cake with PE (4 L×2)
(46) Dried the cake under vacuum at 45° C. to afford yellow solid, 3090.1 g, 99.8% pure by HPLC, 88% yield Step 1.3

(47) Charged EtOH (11.7 L) to a 50-L reactor with a flow of $N_2$ protection
(48) Charged AP2312-2 (3.0 kg)
(49) Charged HOAc (5.4 L)
(50) Charged $H_2O$ (6.3 L)
(51) Warmed the solution mixture to 40° C. and then stopped the heating
(52) Charged Zn powers (1903.3 g) in several portions over 2 hr
Note: 20 min later, the inside temperature rose to 80° C. (exothermic, without cooling) and the mixture became a brown solution after finishing the addition
(53) Agitated the mixture at ambient temperature for 2 h
Note: the temperature dropped to 50° C. after 2 h and HPLC analysis indicated complete consumption of AP2312-2
(54) Charged EtOH (9 L) to the mixture
(55) Stirred the mixture at RT for 1 h
(56) Filtered off the solid
(57) Washed the cake with DCM (15 L)
(58) Transferred the filtrate to a 100-L reactor
(59) Charged DCM (21 L)

(60) Charged water (15 L)
(61) Agitated the mixture for 15 min
(62) Separated the water layer (below layer, TLC showed no residual product)
(63) Washed the organic layer with water (15 L×2)
Note: to remove the residual HOAc and Zn salt
(64) Charged water (15 L) to the organic layer
(65) Charged 3M NaOH aqueous
Note: adjust the pH in organic layer to 9-10
(66) Separated the organic layer
(67) Washed with brine (15 L)
(68) Dried the organic layer over $Na_2SO_4$ (1 kg)
(69) Filtered the salt
(70) Concentrated the filtrate at 45-50° C. under vacuum to a volume of ~15 L
Note: ~0.4 vol of total volume; solid product precipitated from solution.
(71) Charged EtOH (15 L)
(72) Concentrated the mixture at 40° C. to ~15 L
(73) Charged another part of EtOH (5 L)
(74) Agitated the slurry at RT for 2 h
(75) Cooled the mixture to 5-10° C. and agitate at 5-10° C. for 1 h
(76) Collected the solid by filtration
(77) Washed the cake with cold EtOH (2 L×2, 10° C.)
HPLC of wet cake: 99.2%
(78) Dried the cake under vacuum at 35° C. for 48 h to a constant weight to afford off-white solid, 2070.2 g, 99.7% pure by HPLC, 75% yield In Step 2 of the method for synthesizing AMO-01, AP2312-B is prepared as follows:

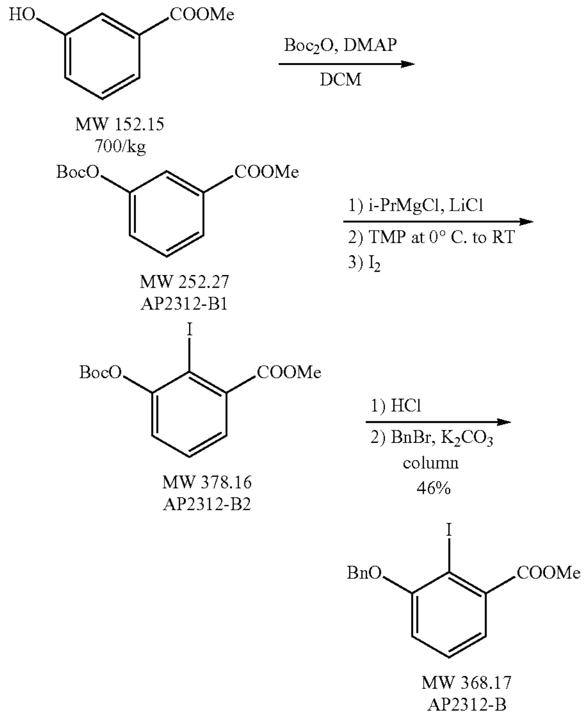

MW 152.15
700/kg
MW 252.27
AP2312-B1
MW 378.16
AP2312-B2
MW 368.17
AP2312-B

The preparation of AP2312-B was achieved via two alternative, highly related schemes. The first scheme included Steps 2.A, 2.B, 2.C and 2.D.

Step 2.A—To a solution of methyl 3-hydroxybenzoate (486 g, 3.2 moL) and DMAP (35.4 g, 0.29 moL) in DCM (2.4 L) was added $Boc_2O$ (763 g, 3.5 moL) dropwise over 2 h. The reaction mixture was stirred at RT for overnight, washed with 8% w/w aqueous citric acid solution (486 mL×3) and water (486 mL), dried over $Na_2SO_4$ (97 g), filtered and concentrated to give 727 g of AP2312-B1 as yellow oil, 90% yield, 100% pure by HPLC.

Step 2.B—A mixture of TMP (367 g, 2.6 moL) and i-PrMgCl·LiCl (2.0 L, 1.3 M in THF) was stirred at RT for 15 h. To a solution of AP2312-B1 (327 g, 1.3 moL) in THF (2.3 L) was added the pre-synthesized TMPMgCl·LiCl dropwise at 0-10° C. over 1 h. After stirring at 0~10° C. for 3 h, the reaction mixture was added a solution of 12 (658 g, 2.6 moL) in THF (1.3 L) dropwise at 0~10° C. over 1 h. The reaction mixture was stirred at RT for 1 h and quenched with 20% w/w $NH_4Cl$ (1 L) at 0~10° C. The mixture was extracted with EtOAc (2.3 L), washed with 10% w/w aqueous $Na_2S_2O_3$ (1.5 L×3) and water (1.5 L), concentrated to dryness to give the crude AP2312-B2, which was used in the next step directly.

Step 2.C—A mixture of the crude AP2312-B2 and concentrated aqueous HCl (3.2 L, 38.4 moL) in MeOH (3.3 L) was stirred at RT for 48 h. The reaction mixture was poured into water (3.3) and the pH of the mixture was adjusted to 7~8 with solid $NaHCO_3$. The mixture was concentrated to remove MeOH and extracted with EA (1.5 L×2). The combined organic layers were concentrated to dryness to give the crude AP2312-B3, which was used in the next step directly.

Step 2.D—A mixture of crude AP2312-B3, BnBr (393 g, 2.3 moL) and $K_2CO_3$ (290 g, 2.1 moL) in acetone (3.3 L) was stirred at 65° C. for 5 h. After cooling to RT, the inorganic salts were filtered off, and the filter cake was washed with EA (660 mL). The filtrate was concentrated and purified by flash chromatography (PE:EtOAc=10:1) to give 242.3 g of AP2312-B, 50% yield for the last three steps, 100% purity by LCMS.

The second scheme for preparing AP2312-B included Steps 2.1, 2.2, 2.3 and 2.4:

Step 2.1
(1) Charged DCM (14.1 L) to a 50-L reactor
(2) Charged methyl 3-hydroxybenzoate (2350.0 g)
(3) Charged DMAP (169.8 g)
(4) Charged $(Boc)_2O$ drop wise at RT (20-25° C.)
Note: $CO_2$ evolved out
(5) Stirred the mixture at RT for 4 h
HPLC indicated that no SM remained (end of the reaction: SM/product: ≤1.0%, a/a)
(6) Washed the organic solution with 8% citric acid aqueous twice (12 L, 4 L)
(7) Washed the organic solution with saturated NaCl solution (5 L)
(8) Dried the organic layer over anhydrous $Na_2SO_4$ (1 kg)
(9) Filtered off the salt
(10) Concentrated the filtrate under vacuum at 40° C. to a volume of 5 L remained
(11) Charged anhydrous THF (10 L) to the residue
(12) Concentrated the solution under vacuum at 40° C. to a volume of ~10 L (10.10 kg)
Analysis of 10.10 kg: Assay 35.07% (3542.1 g contained); HPLC 99.5%; moisture (KF) 0.1%; yield: 91%

Step 2.2
(13) Set a dry, clean reactor
(14) Flushed the system with $N_2$ 3 times
(15) Transferred iPrMgCl·LiCl (12 L, 1.3 M in THF) to the reactor under $N_2$ at RT (10-15° C.)

(16) Charged TMP (2.204 kg, freshly distilled from $CaH_2$) under $N_2$ protection drop wise in 2 hrs at RT Note: Gas (propane) evolved out slowly during the addition

(17) Warmed the gray solution to 30-35° C. in 1 h with stirring

Note: The amount of gas increased when the temperature reached to 30° C., but under control

(18) Stirred the mixture at 30-35° C. for 22 h

Note: Gas evolution ceased. IPC by GC showed that the reaction was complete.

IPC method: quenched an aliquot (0.1 mL base) with 0.02 mL PhCHO at 10° C.; charged 0.5 mL MTBE and 0.5 mL sat. $NH_4Cl$ aq.; separated the organic layer for GC analysis; the absence of the 2-methyl-1-phenylpropan-1-ol indicated full consumption of the Grignard reagent

(19) Charged AP2312-B1 (7.24 kg THF solution, assay 27.1%, 1.967 kg, KF: 0.11%) to a 50 L reactor under $N_2$

(20) Cooled the AP2312-B1 to −5~5° C. under $N_2$

(21) Transferred the TMPMgCl·LiCl solution in step 6 dropwise to the cooled AP2312-B1 solution carefully at 0-5° C. in 1.5 hrs

(22) Stirred the mixture at 0-5° C. for 3 h

IPC: A sample was quenched by $I_2$/THF and HPLC showed that the exchange was complete (SM/Product: 5.0/84.1=6%<10%)

(23) Charged $I_2$/THF (3.96 kg in 8 L THF) solution dropwise to the cooled solution at 0-10° C. in 90 min

(24) Stirred the solution at 0-10° C. for another 40 min

(25) Warmed the solution to 20-25° C.

(26) Stirred the mixture at 20-25° C. for 2 h

HPLC analysis showed that the SM was 2.6%

(27) Cooled the mixture to −10° C.

(28) Charged 20% $NH_4C1$ solution (5 L) to the reaction mixture dropwise, maintaining the temperature at 0-15° C.

(29) Charged water (18 L) at RT

(30) Charged EtOAc (8 L)

(31) Agitated the mixture at RT for 10 min

(32) Separated the organic layer (up)

(33) Extracted the water layer with EtOAc (5 L)

(34) Washed the combined organic layers with 10% $Na_2S_2O_3$ aqueous (10 L×2) Separated the organic layer to give 24.5 kg solution, HPLC: 83.0%

Step 2.3

(35) Charged AP2312-B2 (48.3 kg, combined solution from batch AP2312-B2-1 and AP2312-B2-2, solution after work up) to a 100-L reactor

(36) Charged HCl solution (16 L concentrated HCl mixed with 24 L tap water) to give a solution at RT Note: No obvious temperature rising was observed

(37) Stirred the mixture at RT (25-30° C.) for overnight (16 h)

Note: HPLC analysis indicated that no SM was remained

(38) Transferred the solution to a 200-L reactor

(39) Charged EtOAc (50 L)

(40) Charged 10% NaCl aqueous (50 L)

(41) Separated the layers

(42) Extracted the water layer with EtOAc (30 L)

(43) Washed the combined organic layer with 10% NaCl aqueous (10 L×2)

Note: pH 5-6 after washing

(44) Washed it with sat. $NaHCO_3$ solution (10 L×2)

Note: pH 7 after washing

(45) Washed it with sat. NaCl (10 L)

Concentrated the solution to dryness to afford thick brown oil, 3.80 kg, 82.1% pure by HPLC, 84% total yield from AP2312-B1

Step 2.4

(46) Charged the crude AP2312-B3 (3700 g) to a 50-L reactor

(47) Charged acetone (37 L)

(48) Charged $K_2CO_3$ (2758.5 g)

(49) Charged BnBr (2504.2 g)

(50) Warmed the mixture to 55° C.

(51) Stirred the mixture at 55° C. for 3 h

HPLC (210 nm) analysis indicated that the starting material was <0.5% (0.2% remained)

(52) Cooled the mixture to RT

(53) Filtered the salt

(54) Washed the cake with acetone (3.7 L×2)

(55) Concentrated the filtration at 35-40° C. to afford brown oil 4.5 kg

HPLC of the crude residue: 82.2%

(56) Purified the crude (4.5 kg was diluted with DCM 1 L) with silica gel chromatography Note: Silica gel: 22.5 kg (5.0 eq, w/w), 300-400 mesh; eluting-EtAOc/PE from 50:1 to 20:1

(57) Combined the product fractions (monitored by TLC)

(58) Concentrated the product fractions under vacuum at 35-40° C. to a volume of 2 L Note: Lots of solids separated out

(59) Charged PE (5 L)

(60) Concentrated the slurry at 35-40° C. to a volume of 3 L under vacuum

(61) Collected the solid by filtration

Dried the cake under vacuum at 30° C. to afford light-yellow solid, 2.4 kg, 99.7% pure by HPLC, 49% yield Note: The filtrate was concentrated to afford another 30 g yellow solid with 84% HPLC purity In Step 3 of the method for synthesizing AMO-01, AP2312-3 is prepared via Ullmann Coupling as follows:

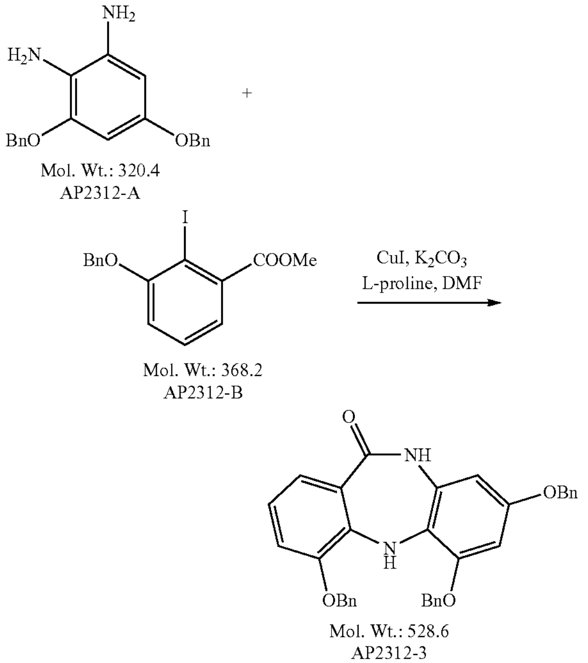

The preparation of AP2312-3 was achieved via alternative, highly related schemes that utilized different amounts of reagents (see Table 1), resulting in different amounts of the desired AP2312 product and different amounts of impurities. The general procedure was as follows. A mixture of AP2312-B (5.0 g, 13.6 mmoL), AP2312-A (4.4 g, 13.6 mmoL), CuI, L-Proline and $K_2CO_3$ (3.8 g, 27.2 mmoL) in DMF (50 mL) and $H_2O$ (5 mL) was degassed by vacuum/nitrogen purge three times. The reaction mixture was stirred at 70° C. for 6 h and a sample was pulled for IPC. After cooling to room temperature, the reaction mixture was added a portion of CuI and degassed by vacuum/nitrogen purge three times. The reaction mixture was stirred at 90° C. for 15 h and a sample was pulled for IPC.

TABLE 1

| No. | CuI Eq. | L-Proline Eq. | Solvents | Temp. | Time | Result -B (4.6') | -IM01 (5.0') | -3 (18.3') | -3J (18.7') | -3I (19.5') |
|---|---|---|---|---|---|---|---|---|---|---|
| 1 | 1% | 2% | DMF 10 v $H_2O$ 1 v | 70° C. | 6 h | 27.2% | 13.2% | 13.6% | 43.1% | 0.4% |
| | +0.5% | — | — | 90° C. | +15 h | 8.1% | 20.9% | 62.0% | 4.6% | 0.9% |
| 2 | 3% | 6% | DMF 10 v $H_2O$ 1 v | 70° C. | 6 h | 5.4% | 24.1% | 32.0% | 35.6% | 0.7% |
| | +1.5% | — | — | 90° C. | +15 h | 0 | 18.4% | 78.2% | 0 | 1.1% |
| 3 | 5% | 10% | DMF 10 v $H_2O$ 1 v | 70° C. | 6 h | 0.5% | 26.6% | 46.9% | 23.4% | 0.6% |
| | +2.5% | — | — | 90° C. | +15 h | 0 | 18.1% | 78.1% | 0 | 1.6% |
| 4 | 5% | 10% | DMF 10 v | 70° C. | 6 h | 27.7% | 7.5% | 0 | 59.2% | 0 |
| | +2.5% | — | — | 90° C. | 15 h | 0 | 21.6% | 66.8% | 8.1% | 0.4% |
| | | | | | 23 h | 0 | 20.2% | 72.0% | 2.7% | 2.5% |
| | | | | | 34 h | 0 | 19.8% | 74.1% | 0 | 2.5% |
| 5 | 7% | 14% | DMF 10 v $H_2O$ 1 v | 70° C. | 6 h | 0.6% | 22.8% | 44.8% | 27.9% | 1.5% |
| | +3.5% | — | — | 90° C. | +15 h | 0 | 16.4% | 79.0% | 0 | 2.3% |
| 6 | 10% | 20% | DMF 10 v $H_2O$ 1 v | 70° C. | 6 h | 0 | 23.9% | 52.2% | 20.0% | 1.9% |
| | +5% | — | — | 90° C. | +15 h | 0 | 18.1% | 76.8% | 0 | 3.0% |
| 7 | 15% | 20% | DMF 10 v | 70° C. | 6 h | 0 | 32.0% | 56.8% | 6.2% | 2.2% |
| | | | $H_2O$ 1 v | 90° C. | 21 h | 0 | 25.7% | 68.0% | 0 | 3.2% |

It was found that with high CuI loading (No. 6 & 7), the reaction was fast and with high de-iodination byproduct of AP2312-B (AP2312-3-IM01). No. 1-6 were performed with a portion of CuI at 70° C. for 6 h to complete the Ullmann coupling reaction and reduce de-iodination byproduct, and then another portion of CuI was added to accelerate the cyclization at 90° C. for 15 h. No. 7 were performed with 15% loading of CuI at 70° C. for 6 h and then 90° C. for 15 h.

It was found that water (compare No. 3 & 4) accelerated the reaction. Without water (No. 4), the Ullmann coupling reaction and cyclization were slow. 27.7% of AP2312-B left was after 6 h at 70° C. and 8.1% of AP2312-3J left after 15 h at 90° C. AP2312-B and AP2312-3J were converted to AP2312-3 completely after 34 h at 90° C. With 1 v water in the system (No. 3), the Ullmann coupling reaction finished in 6 h and cyclization finished in 15 h.

It was found that with low CuI loading (1%+0.5% eq, No. 1), the Ullmann Coupling reaction and Cyclization was slow. 8.1% of AP2312-B left after 6 h at 70° C. and 4.6% of AP2312-3J left after 15 h at 90° C.

No. 5 (7%+3.5% eq CuI) had 79.0% of AP2312-3 in the system and was slightly higher than No. 2 (3%+1.5% eq CuI, 78.2% of AP2312-3) and No. 3 (5%+2.5% eq CuI, 78.1% of AP2312-3). However, with high CuI loading, the ratio of AP2312-31 was raised.

In a specific example, AP2312-3 was prepared via the following steps.

(1) Charged DMF (14.0 L)
(2) Charged water (1.4 L)
(3) Charged AP2312-A (1,230 g, 3.84 mol) to a 20-L 4-necked flask
(4) Charged AP2312-B (1,413 g, 3.84 mol, 1.0 eq)
(5) Charged CuI (36.60 g, 0.192 mol, 0.05 eq)
(6) Charged $K_2CO_3$ (1,060 g, 7.68 mol, 2.0 eq)
(7) Charged L-Proline (44.2 g, 0.384 mol, 0.1 eq)
(8) Heated reaction mixture to 70° C. under $N_2$ for 6 h; HPLC showed that the AP2312-B in 11.7 min was 3.0%
(9) Charged CuI (18.30 g, 0.096 mol, 0.025 eq)
(10) Heated reaction mixture to 90° C. overnight; HPLC showed that no intermediate (Ullmann coupling product at 11.1 min) was detected. 11.4 min: de-iodination by-product: methyl 3-(benzyloxy)benzoate, 16.0%; 9.99 min: hydrolysis by-product 3-(benzyloxy)benzoic acid: 2.4%; 13.4 min: product, 81.6%
(11) Cooled mixture to room temperature
(12) Batches AP2312-3-30, AP2312-3-31 and AP2312-3-33 were combined for work-up
(13) Charged activated carbon (847 g)
(14) Stirred the slurry for 1 h
(15) Filtered off the solid
(16) Washed the cake with DMF (1.4 L×2)
(17) Charged the solution to a 50-L reactor
(18) Charged NaOH aqueous solution (345.6 g in 2.1 L)
(19) Warmed the mixture to 70° C. for 1 h; HPLC showed that all the de-iodine ester in 11.4 min was hydrolyzed to generate the acid (in 10.0 min); 10.0 min: 3-(benzyloxy)benzoic acid, 12.7%; 13.8 min, product, 87.3%
(20) Charged $NH_4C1$ (1,540 g, 28.8 mol, 7.5 eq)
(21) Charged ethylenediamine (877 g, 14.59 mol, 3.8 eq)
(22) Charged the deep purple solution dropwise to a 100-L reactor with 75.6 L of $H_2O$
(23) Stirred slurry for 2 h
(24) Collected the solid by filtration; HPLC showed that almost no AP2312-3 was in the filtrate and the hydrolyzed by-product in 10.0 min was purged into the filtrate (3-(benzyloxy) benzoic acid); HPLC of filtrate (water aqueous):

(25) Dissolved the solid in DCM (21 L)
(26) Dried the solution over anhydrous $Na_2SO_4$ (8 kg)
(27) Filtered off the salt
(28) Concentrated the filtrate to ~7.5 L
(29) Charged hexanes (30.0 L)
(30) Stirred the slurry at RT for 1 h
(31) Collected the solid by filtration to give the crude product (2.8 kg); HPLC: 94.6%, 13.7 min; most impurities were purged into the filtrate
(32) Dissolved the crude solid in toluene (20 L)
(33) Charged active C (420 g)
(34) Warmed the mixture to 110° C.
(35) Stirred the mixture at 110° C. for 2 h
(36) Cooled the mixture to 70-80° C.
(37) Filtered off the active C
(38) Washed the cake with DCM (2.1 L×3)
(39) Concentrated the combined filtrate to ~20 L
(40) Cooled the mixture to RT for 2 h
(41) Cooled the mixture to 5-10° C. for 1 h
(42) Collected the solid by filtration
(43) Washed the cake with EtOH (2.1 L)
(44) Washed the cake with hexanes (2.1 L×2) to give the crude product (1.7 kg); Solid: 96.7%, 13.7 min
(45) Dissolved the crude product in DCM (4.28 L)
(46) Charged hexanes (17.0 L)
(47) Stirred the slurry at RT for 1 h
(48) Collected the solid by filtration to give the crude product
(49) Washed the cake with hexanes (2.1 L)
(50) Dried the cake under vacuum at 40° C. to afford a red solid, 1.58 kg, 50% yield, 99.8% pure by HPLC

TABLE 2

| Batch Record | | | | | |
|---|---|---|---|---|---|
| Batch No. | Amount of AP2312-A | Amount of AP2312-3 | Yield | HPLC Purity | Notes |
| AP2312-3-30 | 44.9 g | — | — | — | Cul: 0.05 eq; solvents: DMF/H2O = 10/1 Combined with batch AP2312-3-34 |
| AP2312-3-31 | 44.9 g | — | — | — | Cul: 0.05 eq; solvents: DMF/H2O = 10/1 Combined with batch AP2312-3-34 |
| AP2312-3-32 | 121.8 g | 103 g | 51% | 99.3% | |
| AP2312-3-33 | 609 g | — | — | — | Combined with batch AP2312-3-34 |
| AP2312-3-34 | 1.23 g | 1.58 kg | 50% | 99.8% | Batches AP2312-3-30, AP2312-3-31, AP2312-3-33 and AP2312-3-34 were combined for workup |

In Step 4 of the method for synthesizing AMO-01, AP2312-4 is prepared via de-benzylation as follows:

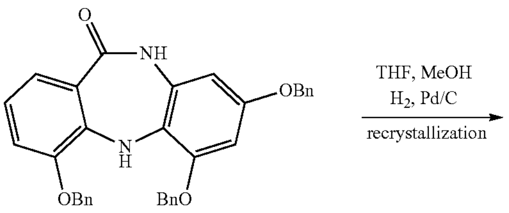

Mol. Wt.: 528.6
AP2313-3

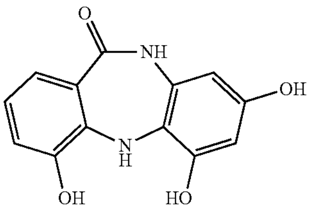

Mol. Wt.: 258.2
AP2312-4

The preparation of AP2312-4 was achieved via the following steps.

(1) Charged AP2312-3 (870 g, 1,645.9 mmol) to a 10-L four necked flask
(2) Charged 10% Pd—C (130.5 g, 0.15 w/w)
(3) Charged THF (2.6 L)
(4) Charged MeOH (2.6 L)
(5) Agitated the slurry under $H_2$ at RT for 36 h
(6) Filtered off Pd—C
(7) Washed the cake with MeOH (172 mL×3)
(8) Concentrated the combined filtrate to black oil (660 g)
(9) Charged Acetone (2.0 L)
(10) Charged hexanes (2.0 L)
(11) Agitated the slurry at RT for 1 h
(12) Collected the solid by filtration
(13) Washed the cake with hexanes (660 mL×2)
(14) Dried the product under vacuum at 35° C. to give pale greenish solid 469 g, 100% pure by HPLC, overweight (110%), which was used in the next step directly

TABLE 3

| Batch Record | | | | | |
|---|---|---|---|---|---|
| Batch No. | Amount of AP2312-3 | Amount of AP2312-4 | Yield | HPLC Purity | Notes |
| AP2312-4-10 | 20 g | — | — | — | HPLC: 13.4 min, 14.6 min was blank |
| AP2312-4-12 | 20 g | 8.7 g | 89% | 100% | Solvents: THF/MeOH No AcOH |
| AP2312-4-13 | 250 g | 107 g | 88% | 100% | Solvents: THF/MeOH |
| AP2312-4-14 | 870 g | 469 g | 110% | 100% | Solvents: THF/MeOH |

In Step 5 of the method for synthesizing AMO-01, AP2312-5 is prepared via silylation as follows:

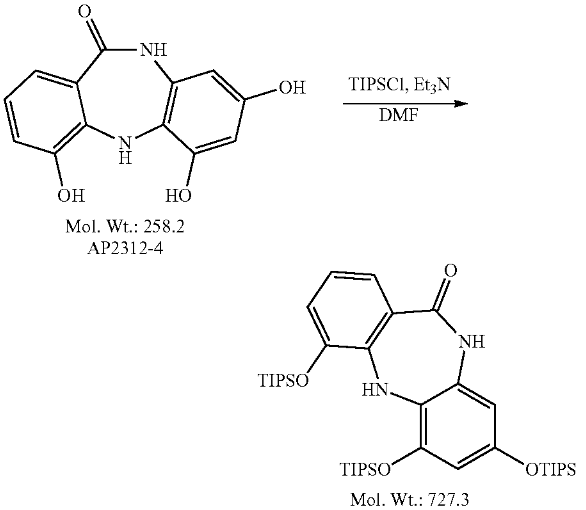

Mol. Wt.: 258.2
AP2312-4

Mol. Wt.: 727.3
AP2312-5

The preparation of AP2312-5 was achieved via the following steps.

(1) Charged DMF (4.0 L) to a 10-L four necked flask
(2) Charged AP2312-4 (450 g, 1,742.8 mmol)
(3) Charged TEA (881.9 g, 8,717 mmol, 5.0 eq)
(4) Cooled the solvent to 0-5° C.
(5) Charged TIPSCl (1,344 g, 6,971.2 mmol, 4.0 eq) dropwise at 0-5° C. over 1 h
(6) Stirred the mixture at RT for 0.5 h
(7) Poured the mixture into $H_2O$ (12.15 L)
(8) Stirred the mixture for 1 h
(9) Collected the solid by filtration
(10) Washed the cake with EtOH (2.9 L×2)
(11) Dried the product under vacuum at 37° C. for 6 h to give a yellow solid, 927 g, 100% pure by HPLC, 80.5% yield over the last 2 steps

TABLE 4

| Batch Record | | | | |
|---|---|---|---|---|
| Batch No. | Amount of AP2312-4 | Amount of AP2312-5 | Yield | HPLC Purity |
| AP2312-5-1 | 50 g | 106 g | 75% | 100% |
| AP2312-5-2 | 450 g | 927 g | 80.5% over the last two steps | 100% |

In Step 6 of the method for synthesizing AMO-01, AP2312-6 is as follows:

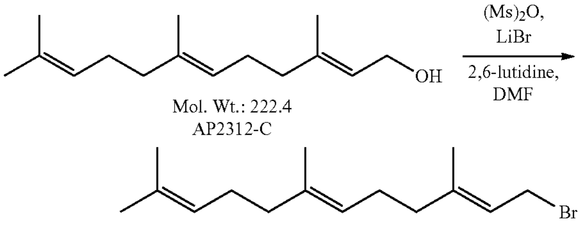

Mol. Wt.: 222.4
AP2312-C

Mol. Wt.: 285.3
AP2312-6

The preparation of AP2312-6 was achieved via the following steps.

(1) Charged DMF (3.7 L) to a 10-L four necked flask
(2) Charged AP2312-C (409 g, 1,839 mmol)
(3) Charge 2,6-lutidine (315.4 g, 2,942.4 mmol, 1.6 eq)
(4) Charge LiBr (255.7 g, 2,942.4 mmol, 1.6 eq)
(5) Cooled the solvent to 0-5° C.
(6) Charged $Ms_2O$ in batches, maintaining the internal temperature at 0-5° C.
(7) Stirred the mixture at 0-5° C. for 3 h
(8) Poured the mixture into ice water (7.4 L)
(9) Added n-Heptane (4.9 L)
(10) Stirred the mixture for 0.5 h
(11) Isolated the organic layer
(12) Passed the organic solution through a pad of silica gel (81.8 g)
(13) Washed the silica gel cake with n-Heptane (818 ml)

(14) Concentrated the filtrate to give yellow oil, 544 g, 90% pure by GC, overweight (103%), which was used in the next step directly

TABLE 5

| Batch Record | | | | |
|---|---|---|---|---|
| Batch No. | Amount of AP2312-C | Amount of AP2312-6 | Yield | HPLC Purity |
| AP2312-6-5 | 50 g | 58 g | 90% | 90% |
| AP2312-6-6 | 409 g | 544 g | 103% | 90% |

In Step 7 of the method for synthesizing AMO-01, AP2312-8 is prepared via farnesylation as follows:

(10) Charged MTBE (12.96 L)

(11) Cooled the solvent to 0-5° C.

(12) Charged $H_2O$ (19.4 L, with 16.1 g of $NH_4C1$) slowly to the solution

(13) Stirred the mixture for 15 min

(14) Isolated the organic layer

(15) Washed with $H_2O$ (16.2 L×3, with 1,620 g of NaCl)

(16) Concentrated the organic layer to black oil

(17) Dissolved the residue in THF (20 L)

(18) Concentrated the solution to black oil

(19) Dissolved the residue in THF (14.6 L)

(20) The solution was used in the next step directly

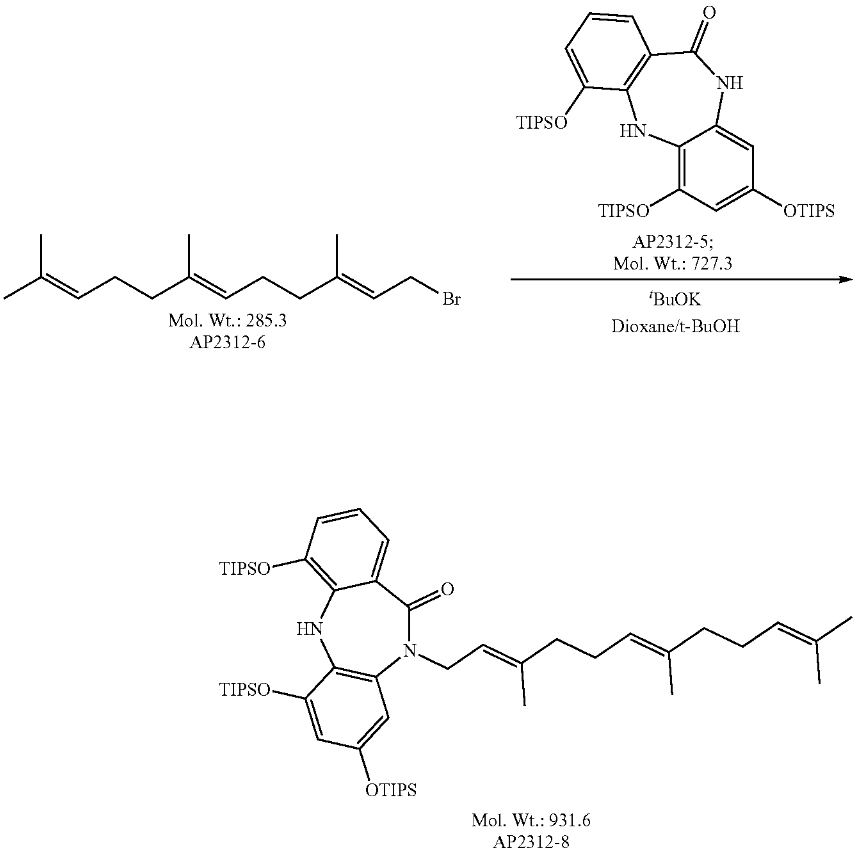

The preparation of AP2312-8 was achieved via the following steps.

(1) Charged dioxane (8.8 L) to a 20-L four necked flask (2) Charged tBuOH (3.8 L)

(3) Charged AP2312-5 (730 g, 1,004 mmol)

(4) Cooled the solvent to 10-15° C.

(5) Charged 1 M $^t$BuOK in $^t$BuOH (1.15 L, 1,150 mmol, 1.15 eq)

(6) Stirred the mixture at 10-15° C. for 2 h (7) Charged AP2312-6 in Dioxane (386.7 g, 730 mL, 1,355 mmol, 1.35 eq)

(8) Stirred the mixture at RT for overnight (9) Batches AP2312-8-8 and AP2312-8-9 were combined for workup

TABLE 6

| Batch Record | | | | | |
|---|---|---|---|---|---|
| Batch No. | Amount of AP2312-5 | Amount of AP2312-8 | Yield | HPLC Purity | Notes |
| AP2312-8-6 | 30 g | — | — | — | |
| AP2312-8-7 | 5 g | — | 100% | — | |
| AP2312-8-8 | 50 g | — | 100% | — | |
| AP2312-8-9 | 730 g | — | 100% | — | Batches AP2312-8-8 and AP2312-8-9 were combined for workup |

In Step 8 of the method for synthesizing AMO-01, AMO-01 (AP2312) is prepared via de-silylation as follows:

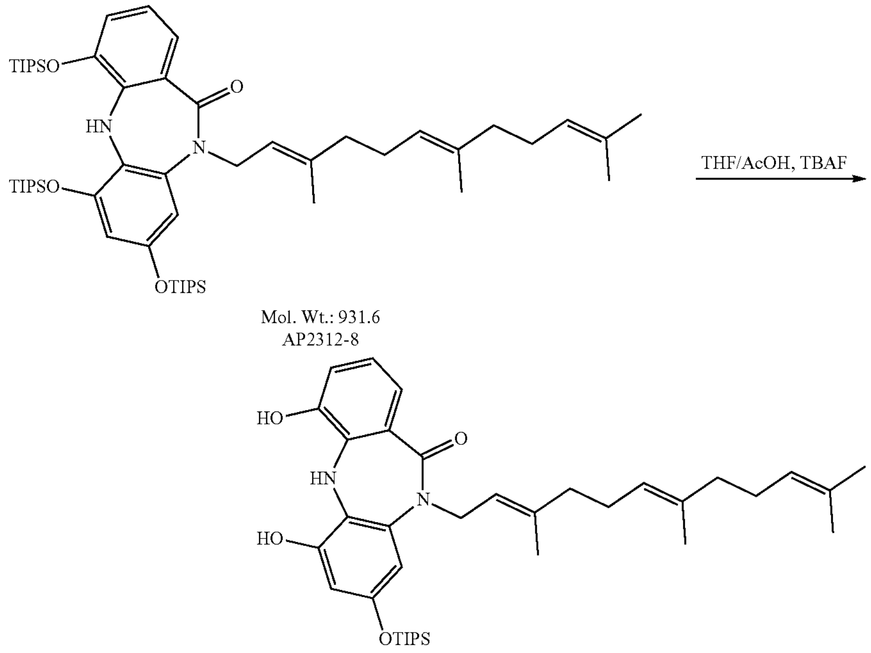

Mol. Wt.: 931.6
AP2312-8

Mol. Wt.: 462.6
AP2312

The preparation of AP2312 was achieved via the following steps.

(1) Charged AP2312-8 in THF (1,037 g, 1,113 mmol, 1.0 eq, 14.6 L) to a 20-L four necked flask
(2) Cooled the solvent to −5 to 5° C.
(3) Charged AcOH (535.1 g, 8,904 mmol, 8.0 eq)
(4) Charged $TBAF \cdot 3H_2O$ (1,404.6 g, 4,452 mmol, 4.0 eq)
(5) Stirred the mixture at RT for overnight
(6) Concentrated the solution to black oil
(7) Dissolved the black oil in EA (10.37 L)
(8) Washed the solution with $H_2O$ (10.37 L×3)
(9) Isolated the organic layer
(10) Concentrated the organic layer to ~2 L
(11) Charged n-Heptane (20,740 ml) over 1 h to the solution
(12) Stirred the mixture for overnight
(13) Collected the solid by filtration
(14) Dissolved the solid in MeOH (4,148 ml) and $H_2O$ (519 ml)
(15) Washed the solution with n-Heptane (4,148 ml×2)
(16) Isolated the MeOH—$H_2O$ layer
(17) Charged activated carbon (104 g)
(18) Stirred the mixture for 1 h
(19) Filtrated off the activated carbon
(20) Washed activated carbon cake with MeOH (1,037 ml)
(21) Charge $H_2O$ (6,222 ml) over 1 h to the combined filtrate
(22) Stirred the mixture for 2 h
(23) Collected the solid by filtration
(24) Dissolved the solid in AcOH (2,074 ml)
(25) Charged $H_2O$ (2,593 ml) over 1 h to the solution
(26) Stirred the mixture for overnight
(27) Collected the solid by filtration
(28) Washed the cake with AcOH/$H_2O$ (519 ml/519 ml)
(29) Washed the cake with $H_2O$ (1,037 ml×2)
(30) Dried the cake under vacuum at 37° C. to afford a light-grey solid, 330 g, 64% yield over the last two steps, 98.3% pure by HPLC

TABLE 7

| Batch Record | | | | |
|---|---|---|---|---|
| Batch No. | Amount of AP2312-8 | Amount of AP2312 | Yield | HPLC Purity |
| AP2312-0-11 | 6.4 g | — | — | — |
| AP2312-0-12 | 1037 g | 330 g | 64% over the last two steps | 98.3% |

Figure 2:
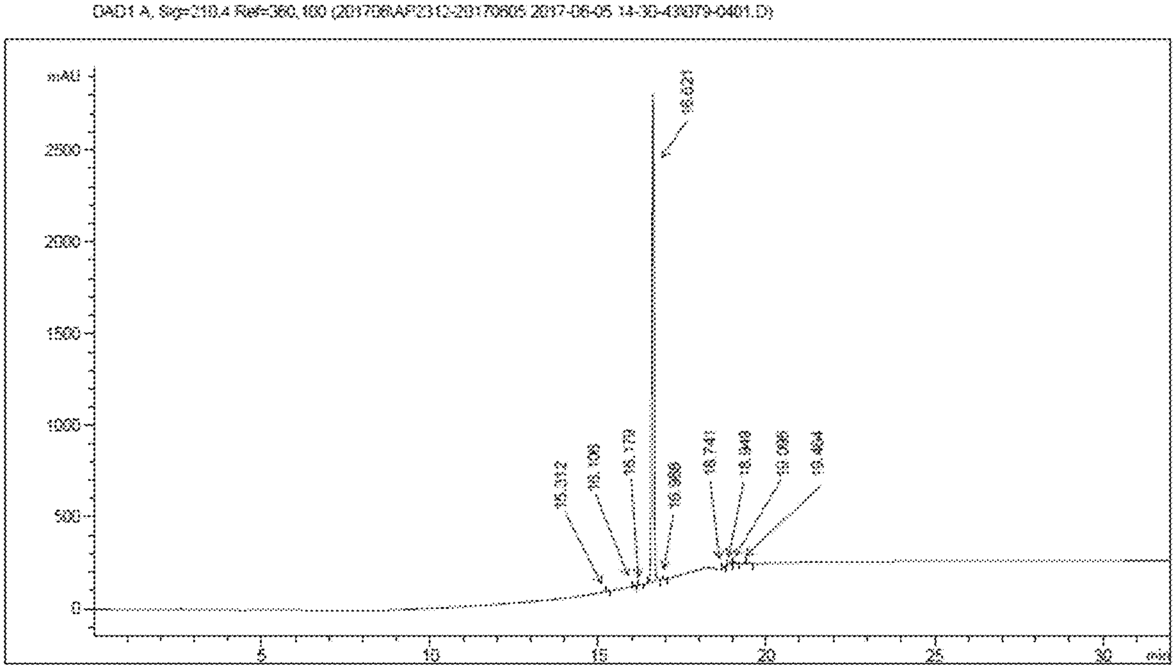
FIG. 2. HPLC results showing 98.3% purity of AMO-01.

In summary, a total of 330 g AP2312 was isolated with 98.3% HPLC purity (FIG. 2). LCMS [M+H] 463; $^1$HNMR (400 MHz; $d_6$ DMSO) δ 9.99 (br. s, 1H), 9.10 (br. s, 1H), 9.00 (br. s, 1H), 7.16 (m, 1H), 6.78 (m, 1H), 6.68 (m, 2H), 6.14 (m, 2H), 5.20 (m, 1H), 5.01 (m, 2H), 4.35 (m, 2H), 1.94 (m, 8H), 1.61 (s, 3H), 1.57 (s, 3H), 1.51 (s, 3H), 1.48 (s, 3H). There were several impurities in the isolated product (RRT 0.93=0.23%, RRT 0.98=0.19%, RRT 1.09=0.40%, RRT 1.11=0.36%, RRT 1.12=0.17%, RRT 1.14=0.12%). This reaction scheme, based on Ullmann coupling, was optimized and confirmed at >1 kg scale.

Compounds of Formula I

It should be apparent that the specific steps provided above for the production of AMO-01 may also be used in the production of the compounds of Formula I and Formula II, with a few alterations.

With respect to the compounds of Formula I, the specific steps for the production of AMO-01 provided above need only be altered when one or more variables A, $R^2$, $R^3$, $R^4$, $R^7$, $R^8$, $W^1$, $W^2$, $W^3$ and x of the compounds (see Formula I) are different from the corresponding variables in AMO-01.

AP2312M-1

The following examples are illustrative. In a first example, Step 4 is altered to produce AP2312M-1, where $R^7$ is $—CH_3$.

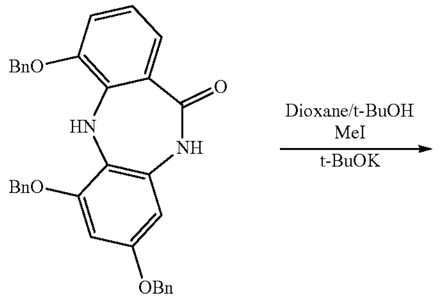

AP2312-3

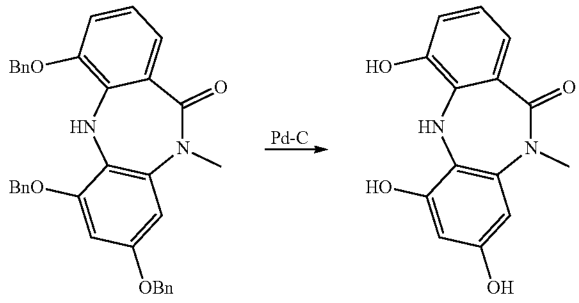

AP2312M-11A

AP2312M-1

To a solution of AP2312-3 (15.9, 30 mmoL) in 1, 4-dioxane (192 mL) and $^t$BuOH (90 mL), $^t$BuOK (5.0 g, 45 mmoL) was added. The reaction mixture was stirred at 30° C. for 2 h. MeI (10.7 g, 75 mmoL) was then added, and the flask was sealed. The reaction mixture was stirred at 30° C. for 24 h. Solvents were removed by concentration under vacuum, the residue was dissolved in water (160 mL), and then extracted with DCM (160 mL×2). The combined organic layers were washed with water (160 mL), concentrated, and purified by reslurrying in petroleum ether (160 mL) and EtOAc (16 mL) to give yellow solid, AP2312-11A, 15 g, 99.4% pure by HPLC, 92% yield.

The mixture of AP2312M-11A (15.0 g, 27.6 mmoL) and 10% Pd/C (50% wet, 2.4 g) in THF (45 mL) and MeOH (45 mL) was stirred at 40° C. under hydrogen pressure of 0.1 MPa for 24 h. The reaction mixture was cooled to room temperature, and the catalyst was filtered off. The filtrate was concentrated and purified by flash chromatography (DCM: MeOH=20:1) to give yellow solid, AP2312M-1, 6.5 g, 99.1% pure by HPLC, 87% yield. LCMS [M+H] 273; $^1$HNMR ($d_6$-DMSO, 500 MHz) δ 10.08 (s, 1H), 9.99 (s, 1H), 9.12 (s, 1H), 7.10 (m, 1H), 6.85 (m, 1H), 6.76 (s, 1H), 6.71 (m, 1H), 6.20 (m, 1H), 6.12 (m, 1H), 3.29 (s, 3H).

AP2312M-2

In a second example, Step 6 is altered to produce AP2312M-2, where $R^7$ is 1-bromo-3-methyl-2-butene.

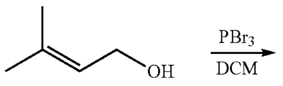

3-methylbut-2-en-1-ol
AP2312M-21

-continued

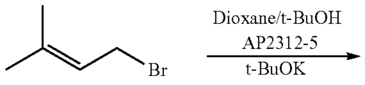

AP2312M-22

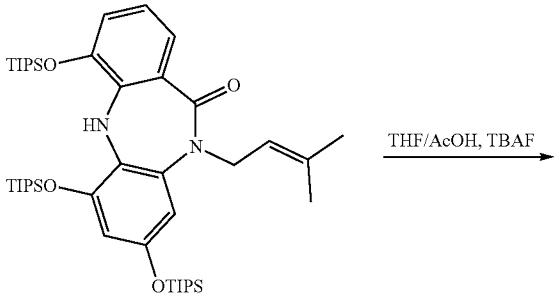

AP2312M-23

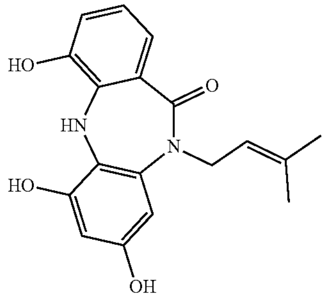

AP2312M-2

To a solution of AP2312M-21 (86.0 g, 1.0 moL) in DCM (430 mL) was added $PBr_3$ (108.4 g, 0.4 moL) dropwise at 0~10° C. over 1 h. The reaction mixture was stirred for overnight at RT and purified by distillation (~50° C./−0.1 MPa) to give 35.6 g of AP2312M-22, 24% yield, which was used in the next step directly.

To a solution of AP2312-5 (21.8 g, 30 mmoL) in 1, 4-dioxane (262 mL) and $^t$BuOH (110 mL) was added $^t$BuOK (5.0 g, 45 mmoL). The reaction mixture was stirred for 2 h at 30° C. AP2312M-22 (11.2 g, 75 mmoL) was then added, and the reaction mixture was stirred for 2 h at 30° C. After evaporation of solvents, the residue was added water (220 mL) and extracted with EtOAc (110 mL×2). The combined organic layers were washed with water (220 mL) and concentrated to give the crude AP2312M-23, which was used in the next step directly.

The crude AP2312M-23 was dissolved in THF (220 mL), followed by addition of TBAF (120 mL, 1 M in THF), AcOH (14.4 g, 240 mmoL). The reaction mixture was stirred at 30° C. for 6 h. The reaction mixture was poured into water (440 mL), extracted with EtOAc (440 mL×1). The organic layer was washed with water (110 mL×6), concentrated and purified by flash chromatography (DCM:MeOH=30:1) to give 4.2 g of AP2312M-2 as grey solid, 43% yield for the last two steps, 99.4% purity by HPLC, which was confirmed by $^1$H NMR and LCMS. LCMS [M+H] 327; $^1$H NMR ($d_6$-DMSO, 500 MHz) δ 10.03 (s, 1H), 9.96 (s, 1H), 9.07 (s, 1H), 7.07 (d, 1H), 6.83 (d, 1H), 6.72 (m, 2H), 6.17 (s, 2H), 5.26 (m, 1H), 4.39 (m, 2H), 1.68 (s, 3H), 1.65 (s, 3H).

AP2312M-3

In a third example, Step 6 is altered to produce AP2312M-3, where $R^7$ is again altered.

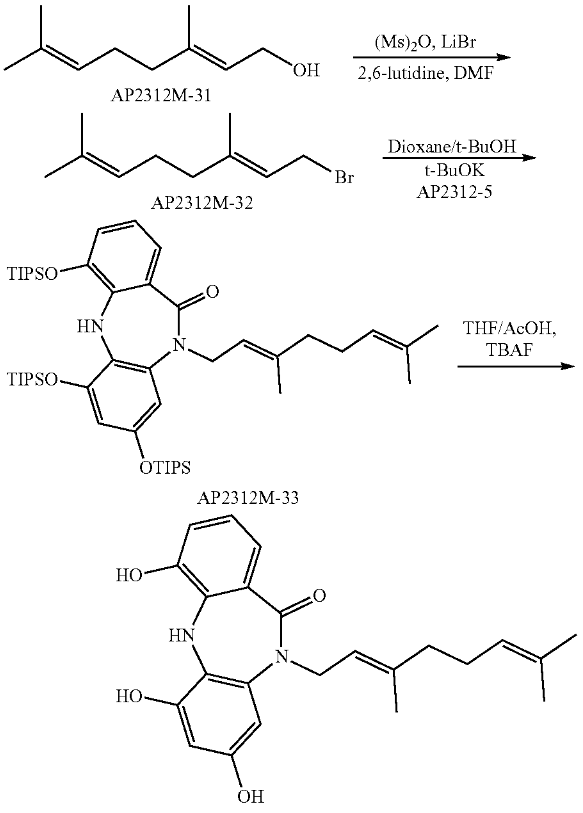

AP2312M-31

AP2312M-32

AP2312M-33

AP2312M-3

To a solution of AP2312M-31 (9.2 g, 60 mmoL), 2,6-lutidine (10.3 g, 96 mmoL) and LiBr (8.4 g, 96 mmoL) in DMF (92 mL) was added (Ms)$_2$O (15.7 g) in portions at 0~10° C. The reaction mixture was stirred for 2 h at 0~10° C., poured into water (276 mL) and extracted with petroleum ether (92 mL×2). The combined organic layers were washed with water (92 mL) and concentrated to give 11.0 g of AP2312M-32, 85% yield, which was used in the next step directly.

To a solution of AP2312-5 (14.5 g, 20 mmoL) in 1,4-dioxane (174 mL) and $^t$BuOH (73 mL) was added $^t$BuOK (3.4 g, 30 mmoL). The reaction mixture was stirred for 2 h at 30° C. AP2312M-32 (6.5 g, 30 mmoL) was then added, and the reaction mixture was stirred for 2 h at 30° C. After evaporation of solvents, the residue was added water (145 mL) and extracted with EtOAc (145 mL×2). The combined organic layers were washed with water (145 mL) and concentrated to give the crude AP2312M-33, which was used in the next step directly.

The crude AP2312M-33 was dissolved in THF (145 mL), followed by addition of TBAF (80 mL, 1 M in THF), AcOH (9.6 g, 160 mmoL). The reaction mixture was stirred at 30° C. for 6 h, poured into water (440 mL) and extracted with EtOAc (290 mL). The organic layer was washed with water (145 mL×6), concentrated and purified by flash chromatography (DCM:MeOH=40:1) to give 5.5 g of AP2312M-3 as grey solid, 70% yield for the last two steps, 98.2% purity by HPLC, which was confirmed by $^1$H NMR and LCMS. LCMS [M+H] 395, $^1$HNMR (d$_6$-DMSO, 500 MHz) δ 10.04 (s, 1H), 9.95 (s, 1H), 9.05 (s, 1H), 7.07 (m, 1H), 6.83 (m, 1H), 6.72 (m, 2H), 6.17 (m, 2H), 5.24 (m, 1H), 5.03 (m, 1H), 4.40 (m, 2H), 2.24 (m, 4H), 1.65 (s, 3H), 1.61 (s, 3H), 1.55 (s, 3H).

AP2312M-4

In a fourth example, Step 6 is altered to produce AP2312M-4, where R$^7$ is again altered.

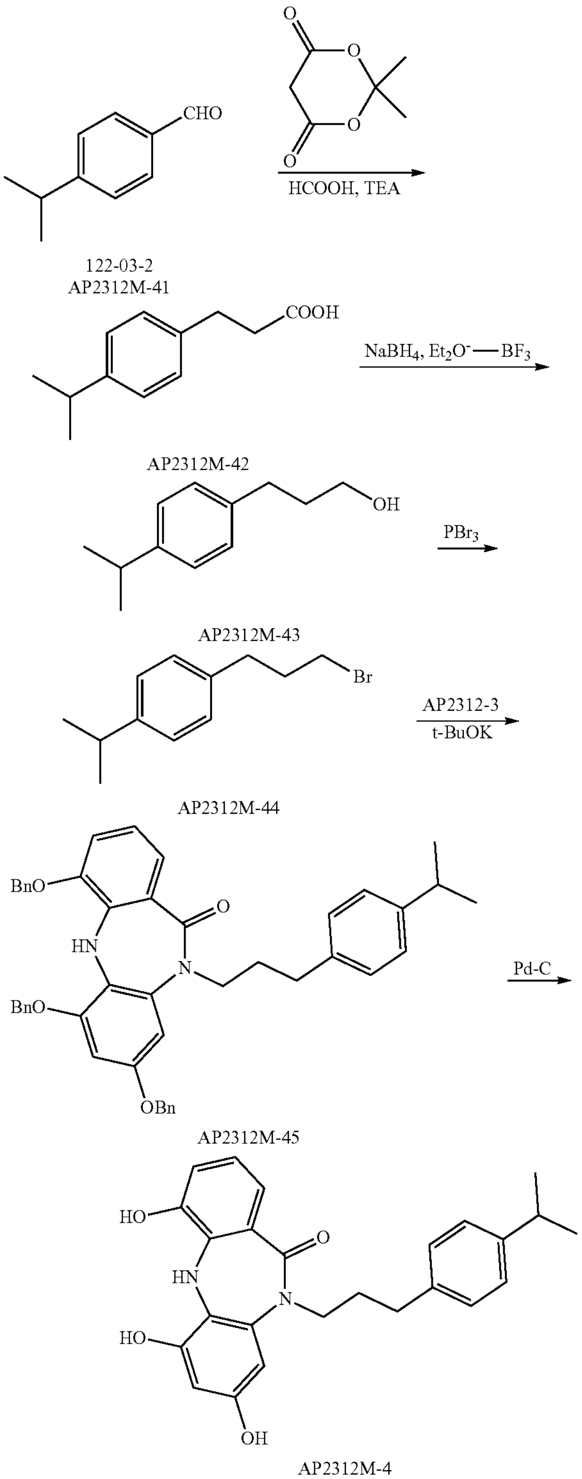

122-03-2

AP2312M-41

AP2312M-42

AP2312M-43

AP2312M-44

AP2312M-45

AP2312M-4

DMF (100 mL) was added sequentially HCOOH (41.4 g, 0.9 moL), TEA (39.5 g, 0.39 moL) and Meldrum's acid (43.2 g, 0.3 moL) at 0~10° C. The reaction mixture was stirred at 0~10° C. for 0.5 h, and then added AP2312M-41 (44.5 g, 0.3 moL). The reaction mixture was stirred at 80° C.

for overnight. After cooling to RT, the reaction mixture was poured into ice water (1.2 L) and the pH of the mixture was adjusted to 1~2 with concentrated aqueous HCl at 0~10° C. The mixture was filtered and the filter cake was washed with water (100 mL). The filter cake was dissolved in DCM (300 mL) and dried over $Na_2SO_4$ (90 g). After filtering off the inorganic salts, the filtrate was concentrated to dryness to give the crude AP2312M-42, which was used in the next step directly.

To a solution of crude AP2312M-42 in THF (845 mL) was added $NaBH_4$ (22.8 g, 0.6 moL) in portions at 0~10° C. over 0.5 h. The reaction mixture was added $BF_3{\cdot}Et_2O$ (110.7 g, 0.78 moL) dropwise at 0~10° C. over 1.5 h. After stirred at RT for 3 h, the reaction mixture was poured into ice water (300 mL) and the pH of the mixture was adjusted to 2~3 with 2 M HCl at 0~10° C. The mixture was extracted with DCM (600 mL×2). The combined organic layers were washed with saturated $NaHCO_3$ (500 mL) and brine (500 mL), concentrated and purified by flash chromatography (PE: EA=5:1) to give 46.0 g of AP2312M-43 as colorless oil, 86% yield for two steps.

To a solution of AP2312M-43 (29.4 g, 165 mmoL) in DCM (294 mL) was added $PBr_3$ (17.9 g, 66 mmoL) dropwise at 0~10° C. The reaction mixture was stirred at RT for 15 h, washed with water (210 mL), concentrated and purified by flash chromatography (PE:EA=20:1) to give 19.5 g of AP2312M-53 as off-white solid, 49% yield.

To a solution of AP2312-3 (21.2 g, 40 mmoL) in 1, 4-dioxane (254 mL) and $^t$BuOH (106 mL) was added $^t$BuOK (5.8 g, 52 mmoL). The reaction mixture was stirred for 2 h at 30° C. AP2312M-44 (19.3 g, 80 mmoL) was then added, and the reaction mixture was stirred for 24 h at 30° C. After evaporation of solvents, the residue was added water (212 mL) and extracted with EtOAc (106 mL×2). The combined organic layers were washed with water (106 mL) and concentrated to give the crude AP2312M-45 as yellow solid, which was used in the next step directly.

The crude AP2312M-45 was dissolved in THF (212 mL) and MeOH (106 mL), followed by addition of 10% Pd/C, 50% water wet (3.2 g). The reaction mixture was degassed by vacuum/hydrogen purge three times and stirred at 40° C. under hydrogen pressure of 0.1 MPa for 24 h. After cooling the reaction mixture to room temperature, the catalyst was filtered off. The filtrate was concentrated and purified by flash chromatography (DCM:MeOH=40:1) to give 6.7 g of AP2312M-4 as grey solid, 40% yield for the last two steps, 98.0% purity by HPLC, which was confirmed by $^1$H NMR and LCMS. LCMS [M+H] 419; $^1$HNMR ($d_6$-DMSO, 500 MHz) δ 10.06 (s, 1H), 10.01 (s, 1H), 9.09 (s, 1H), 7.06 (m, 3H), 6.99 (m, 2H), 6.83 (m, 1H), 6.78 (s, 1H), 6.73 (m, 1H), 6.19 (m, 2H), 3.91 (m, 2H), 2.81 (m, 1H), 2.53 (m, 2H), 1.76 (m, 2H), 1.15 (d, 6H).

AP2312M-5

In a fifth example, Step 6 is altered to produce AP2312M-5, where $R^7$ is again altered.

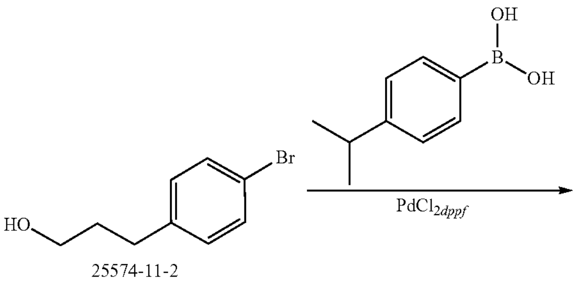

25574-11-2
AP2312M-51

-continued

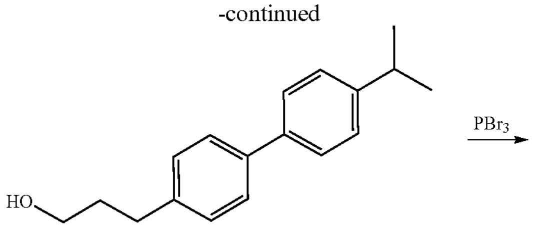

AP2312M-52

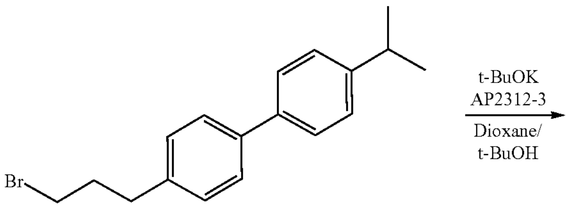

AP2312M-53

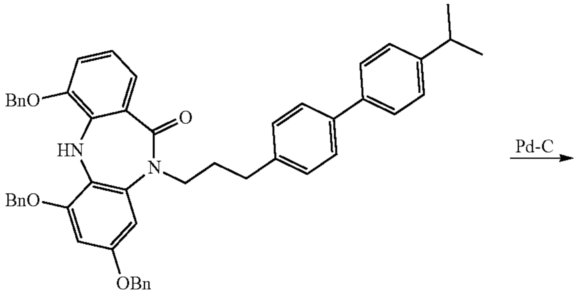

AP2312M-54A

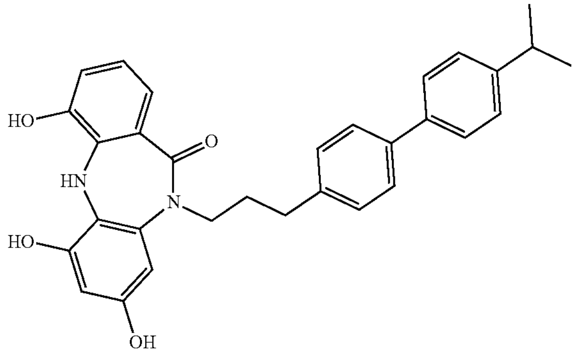

AP2312M-5

A mixture of AP2312M-51 (25.0 g, 116 mmoL), 4-Isopropylphenylboronic acid (22.8 g, 139 mmoL), $PdCl_2$(dppf) (878 mg, 1.2 mmoL) and $K_2CO_3$ (32.0 g, 232 mmoL) in MeOH (300 mL) and $H_2O$ (100 mL) was degassed by vacuum/nitrogen purge three times. After stirring at 70° C. for 15 h, the reaction mixture was concentrated to remove MeOH and extracted with EtOAc (100 mL×2). The combined organic layers were concentrated and purified by flash chromatography (PE:EA=10:1) to give 22.0 g of AP2312M-52 as off-white solid, 74% yield.

To a solution of AP2312M-52 (22.0 g, 86.6 mmoL) in DCM (220 mL) was added $PBr_3$ (11.7 g, 43.3 mmoL) dropwise at 0~10° C. The reaction mixture was stirred at RT for 15 h, washed with water (220 mL), concentrated and purified by flash chromatography (PE:EA=30:1) to give 11.3 g of AP2312M-53 as off-white solid, 41% yield.

To a solution of AP2312-3 (12.2 g, 23 mmoL) in 1, 4-dioxane (146 mL) and $^t$BuOH (61 mL) was added $^t$BuOK (3.4 g, 30 mmoL). The reaction mixture was stirred for 2 h at 30° C. AP2312M-53 (11.1 g, 35 mmoL) was then added, and the reaction mixture was stirred for 24 h at 30° C. After evaporation of solvents, the residue was added water (122 mL) and extracted with EtOAc (61 mL×2). The combined organic layers were washed with water (61 mL) and concentrated to give the residue AP2312M-54A as yellow solid, which was used in the next step directly.

The crude AP2312M-54A was dissolved in THF (122 mL) and MeOH (61 mL), followed by addition of 10% Pd/C, 50% water wet (1.8 g). The reaction mixture was degassed by vacuum/hydrogen purge three times and stirred at 40° C. under hydrogen pressure of 0.1 MPa for 24 h. After cooling the reaction mixture to room temperature, the catalyst was filtered off. The filtrate was concentrated and purified by flash chromatography (DCM:MeOH=40:1) to give 8.0 g of AP2312M-5 as off-white solid, 70% yield for the last two steps, 99.0% purity by HPLC, which was confirmed by $^1$H NMR and LCMS. LCMS [M+H] 495; $^1$HNMR ($d_6$-DMSO, 500 MHz) δ 10.07 (s, 1H), 10.02 (s, 1H), 9.10 (s, 1H), 7.50 (m, 4H), 7.30 (m, 2H), 7.16 (m, 2H), 7.07 (m, 1H), 6.83 (m, 1H), 6.80 (s, 1H), 6.73 (m, 1H), 6.20 (m, 2H), 3.94 (m, 2H), 2.90 (m, 1H), 2.62 (m, 2H), 1.82 (m, 2H), 1.22 (d, 6H).

Compounds of Formula II

As suggested above, the specific steps provided for the production of AMO-01 may also be used in the production of the compounds of II, with a few alterations. The compounds of Formula II result from the use of Buchwald coupling in place of Ullmann coupling in Step 3.

Initial experiments used in the production of AMO-01 provided the surprising finding that by using Buchwald coupling, compounds of Formula II were realized, while use of Ullmann coupling resulted in the compounds of Formula I.

An experiment was conducted to confirm that Buchwald chemistry gave the isomer AP2312-3I, and not AP2312-3.

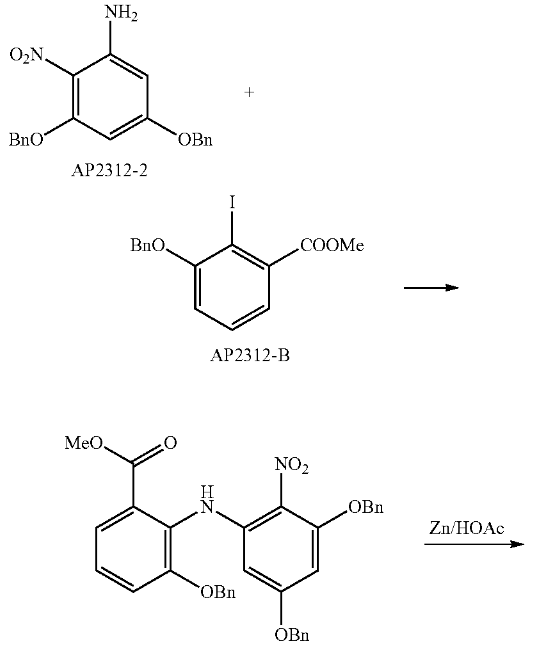

AP2312-2
AP2312-B
AP2312-14

-continued

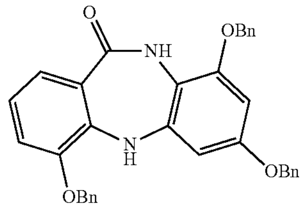
AP2312-3I

A mixture of AP2312-2 (21.0 g, 60 mmoL), AP2312-B (28.8 g, 78 mmoL), $Pd_2(Dba)_3$ (1.1 g, 1.2 mmoL), X-Phos (2.8 g, 3.6 mmoL) and $Cs_2CO_3$ (49.2 g, 150 mmoL) in Tol (210 mL) was degassed by vacuum/nitrogen purge three times. The reaction mixture was stirred at 110° C. for 48 h. The reaction mixture was poured into water (210 mL), extracted with EA (210 mL×2). The combined organic layers were washed with water (210 mL), concentrated and purified by flash chromatography (PE:EA=10:1) to give 26.0 g of AP2312-14, 73% yield, 98.0% purity by HPLC.

AP2312-14 (25.0 g, 42.4 mmoL) was suspend in EtOH (100 mL), $H_2O$ (50 mL) and AcOH (45 mL). The reaction mixture was added zinc powder (9.4 g, 144.2 mmoL) in portions at RT. The reaction was highly exothermic and temperature rose to 80° C. in 1 h. The reaction mixture was stirred at 80° C. for 2 h. After cooling the reaction mixture to room temperature, the inorganic salts were filtered off and the filter cake was washed with DCM (200 mL). The filtrate was concentrated to remove organic solvents and extracted with DCM (250 mL×1). The organic layer was washed with water (100 mL×3), concentrated and purified by reslurrying in EtOH (100 mL) to give 21.0 g of AP2312-3I as yellow solid, 100% pure by LCMS, 94% yield.

Buchwald coupling was then used to produced AP2312-3I, as follows.

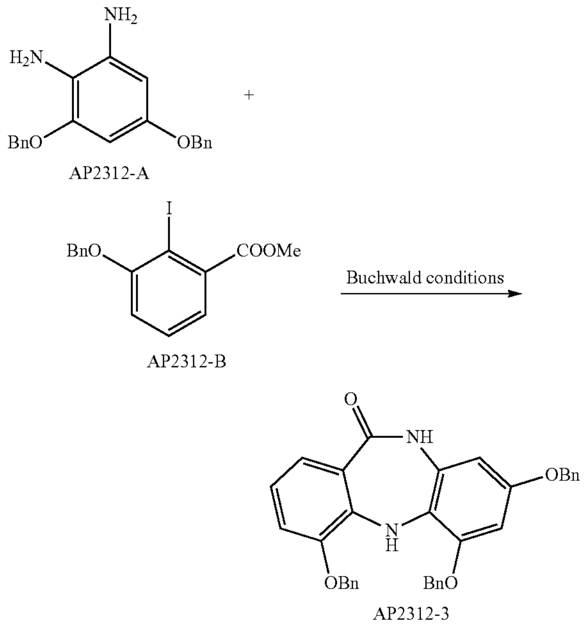

AP2312-A
AP2312-B
AP2312-3

-continued

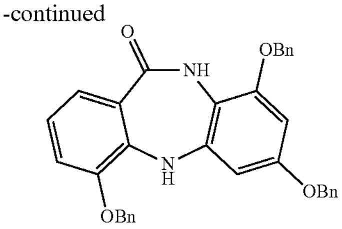

AP2312-3I

A mixture of AP2312-A (1.3 g, 4 mmoL), AP2312-B (1.5 g, 4 mmoL), $PdCl_2$(dppf) (146 mg, 0.2 mmoL) and $Cs_2CO_3$ (1.8 g, 5.6 mmoL) in DMF (26 mL) was degassed by vacuum/nitrogen purge three times. The reaction mixture was stirred at 100° C. for 15 h. A sample was pulled for IPC, and HPLC indicated 47.0% of AP2312-3I (20.7 min) and no AP2312-3 (19.0 min) in the system. LCMS [M+H] 529; $^1$HNMR ($d_6$-DMSO, 500 MHz) δ 8.76 (s, 1H), 7.53 (m, 4H), 7.35 (m, 11H), 7.22 (m, 1H), 7.13 (m, 1H), 7.08 (s, 1H), 6.85 (m, 1H), 6.49 (m, 1H), 6.40 (m, 1H), 5.26 (s, 2H), 5.11 (s, 2H), 5.03 (s, 2H).

While the invention has been described with reference to certain particular embodiments thereof, those skilled in the art will appreciate that various modifications may be made without departing from the spirit and scope of the invention. The scope of the appended claims is not to be limited to the specific embodiments described.

What is claimed is:

1. A method of synthesizing a farnesyl dibenzodiazepinone of Formula I and salts thereof:

Formula I

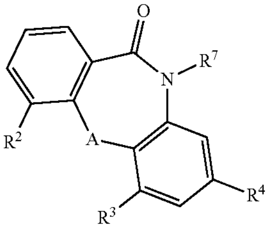

wherein,

A is —NH—;

$R^7$ is —$CH_3$, —$(CH_2)_xCH_3$, —$CH_2CH_2W^1CH_3$, —$CH_2CH_2W^1CH_2CH_2W^2CH_3$ or —$CH_2W^1CH_2CH_2W^2CH_2CH_2W^3CH_3$, where x is an integer of from 1 to 11, and where each of $W^1$, $W^2$ and $W^3$ is independently

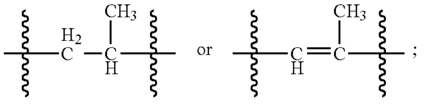

$R^2$ is —H, —OH, —$OCH_3$ or —OP═O($OR^8$), where $R^8$ is —Na, —$CH_3$ or —$CH_2CH_3$; and $R^3$ and $R^4$ are the same and selected from —H, —OH, —$OCH_3$ or —OP═O($OR^8$), where $R^8$ is —Na, —$CH_3$ or —$CH_2CH_3$, said method comprising:

(a) preparing AP2312-A;

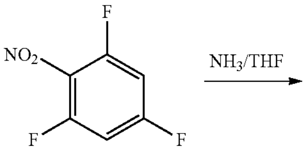

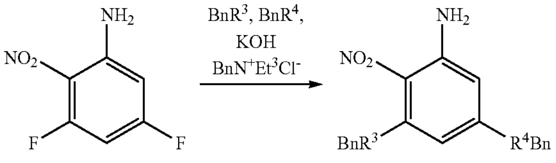

AP2312-1 AP2213-2

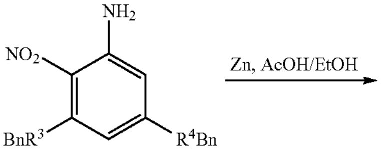

AP2213-2

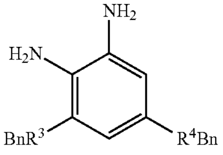

AP2312-A (b) preparing AP2312-B;

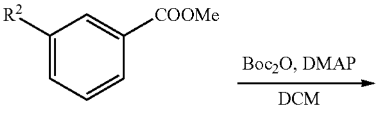

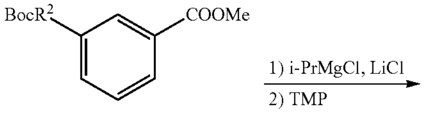

AP2312-B1

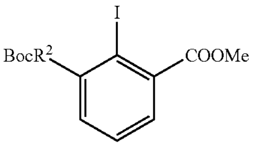

AP2312-B2

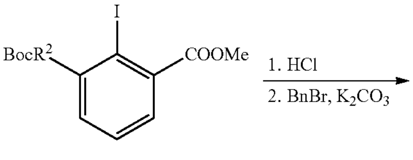

AP2312-B2

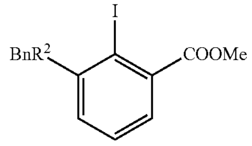

AP2312-B (c) performing Ullmann coupling;
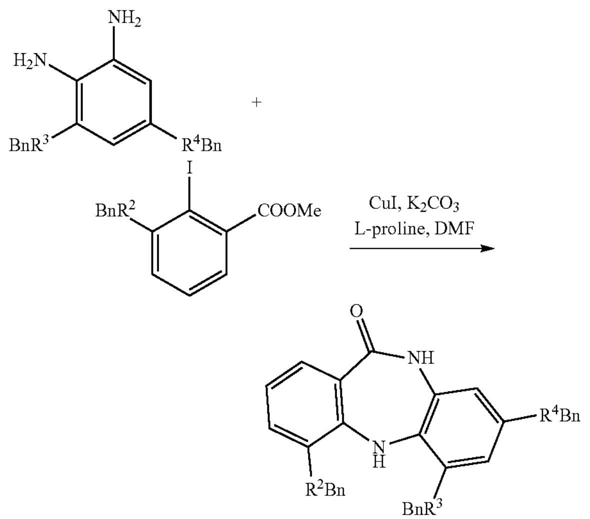
(d) performing de-benzylation;
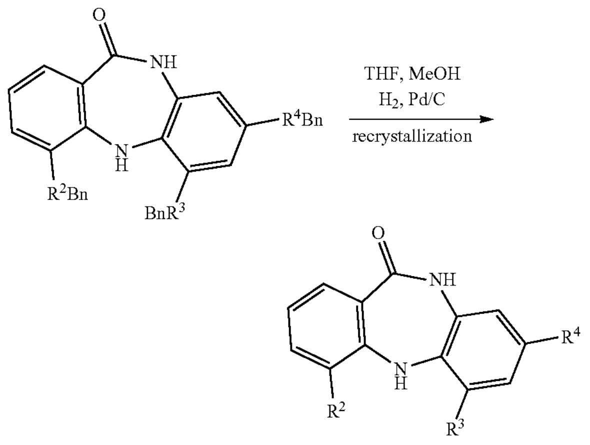
(e) performing silylation;
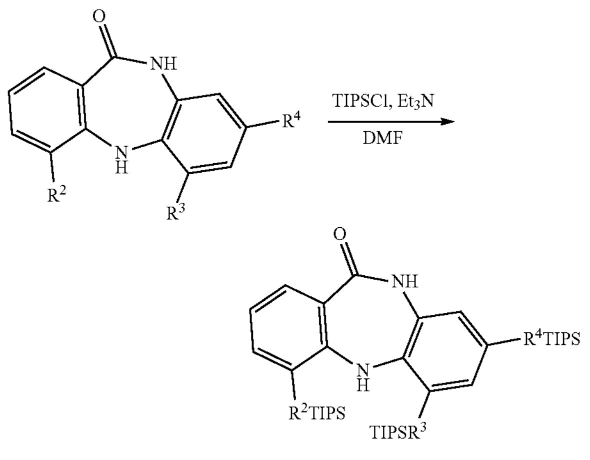
(f) preparing $R^7$;
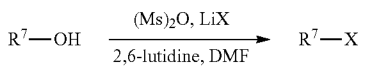
wherein X is Br, I, or Cl
(g) performing farnesylation; and
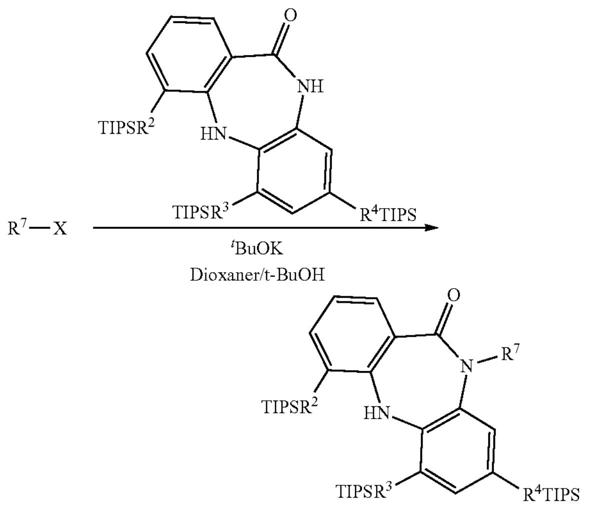
(h) performing de-silylation
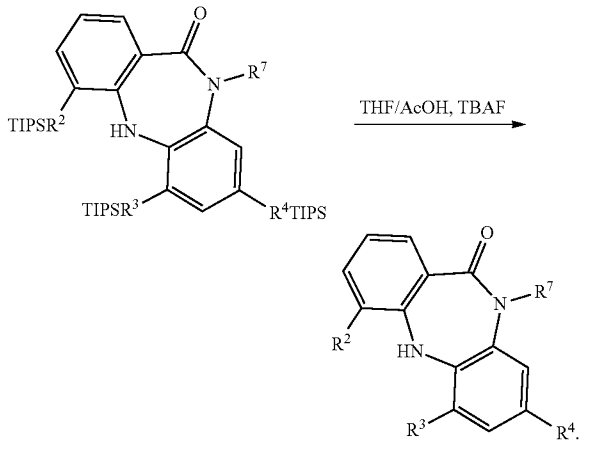
2. A method of synthesizing a farnesyl dibenzodiazepinone of Formula II and salts thereof:
Formula II
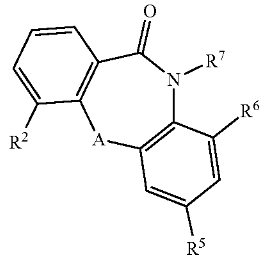

wherein,

A is —NH—;

$R^7$ is —$CH_3$, —$(CH_2)_xCH_3$, —$CH_2CH_2W^1CH_3$, —$CH_2CH_2W^1CH_2CH_2W^2CH_3$ or —$CH_2W^1CH_2CH_2W^2CH_2CH_2W^3CH_3$, where x is an integer of from 1 to 11, and where each of $W^1$, $W^2$ and $W^3$ is independently

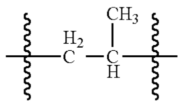

or

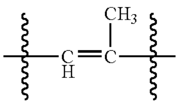

;

$R^2$ is —H, —OH, —$OCH_3$ or —OP═O($OR^8$), where $R^8$ is —Na, —$CH_3$ or —$CH_2CH_3$; and $R^5$ and $R^6$ are the same and selected from —H, —OH, —$OCH_3$ or —OP═O($OR^8$), where $R^8$ is —Na, —$CH_3$ or —$CH_2CH_3$, said method comprising:

(a) preparing AP2312-A;

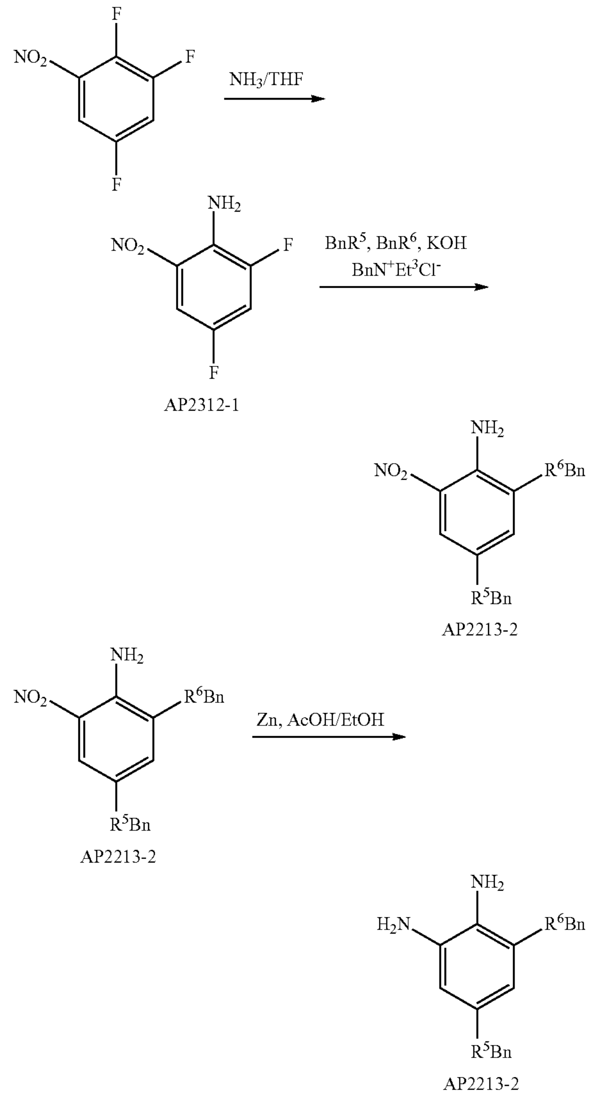

(b) preparing AP2312-B;

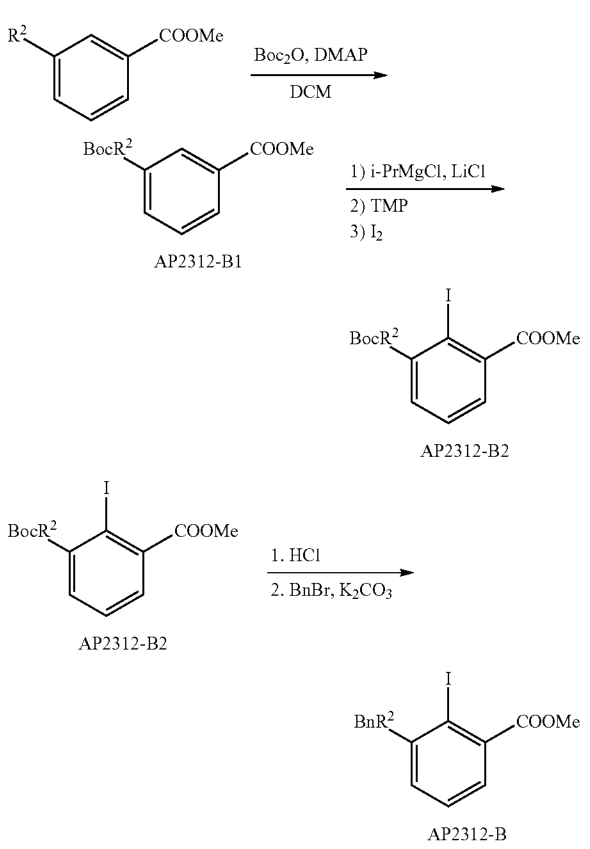

(c) performing Buchwald coupling;

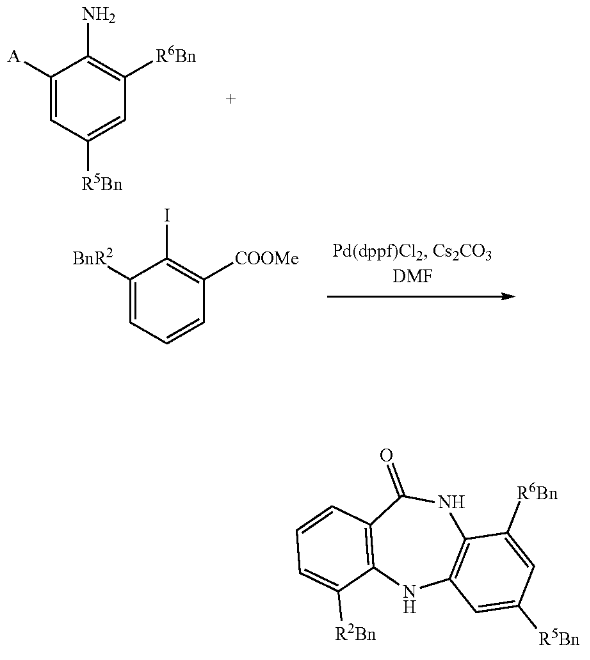

(d) performing de-benzylation;
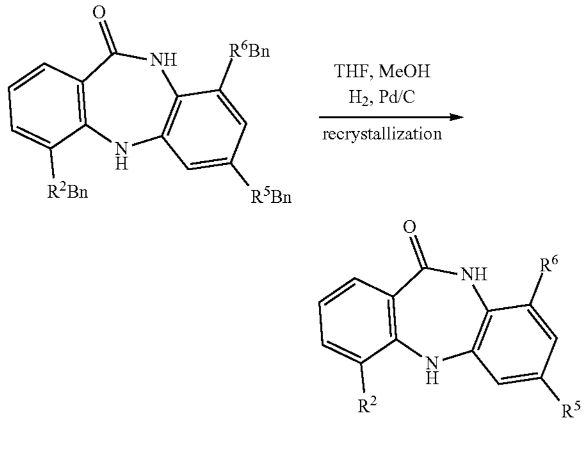
(e) performing silylation;
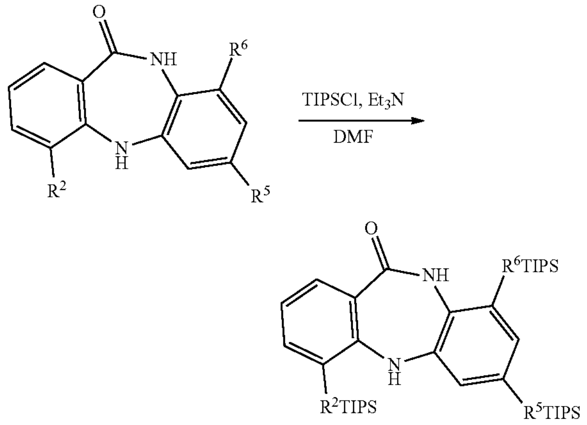
(f) preparing $R^7$;
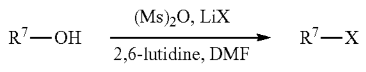
wherein X is Br, I, or Cl
(g) performing farnesylation; and
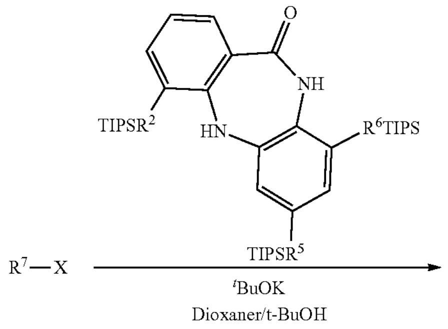
-continued
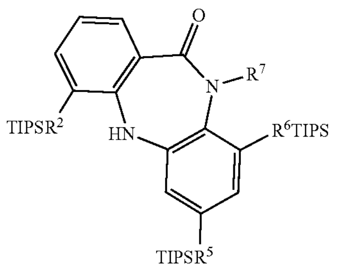
(h) performing de-silylation
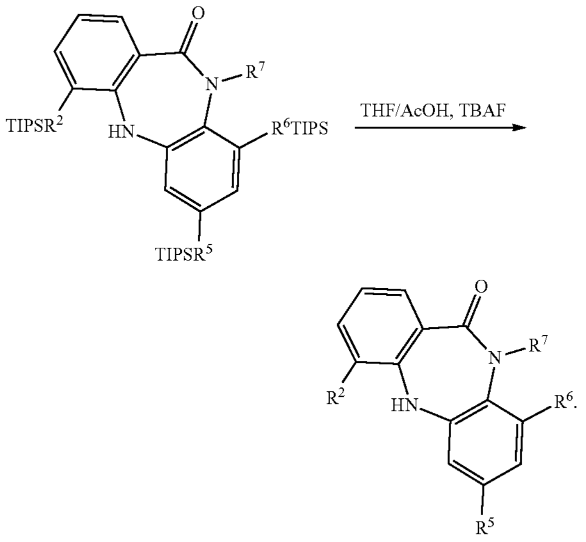
3. A method of synthesizing the farnesyl dibenzodiazepinone AMO-01 (10-farnesyl-4,6,8-trihydroxy-dibenzodiazepin-11-one),
AMO-01
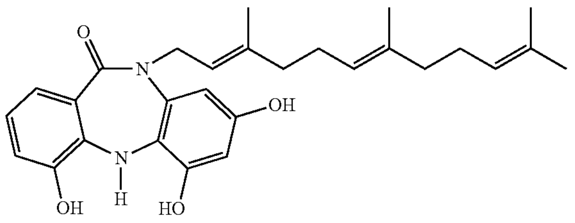
said method comprising:
(a) preparing AP2312-A;
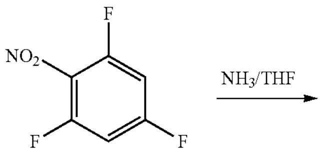

-continued
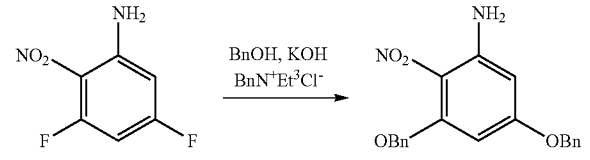
AP2312-1 AP2213-2
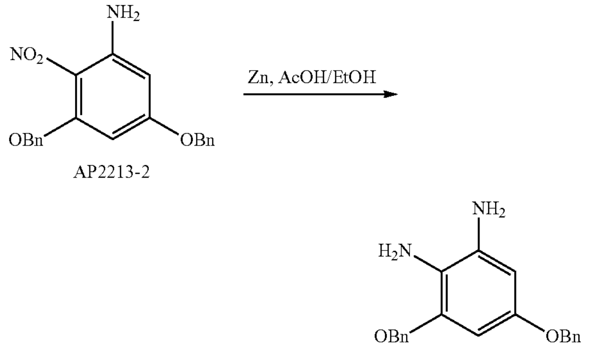
AP2213-2
AP2312-A
(b) preparing AP2312-B;
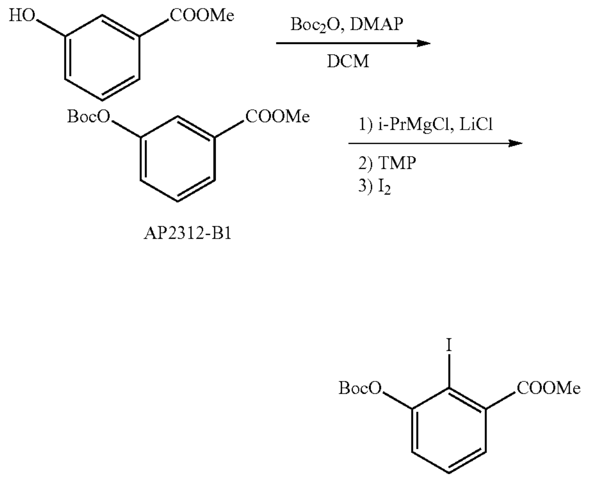
AP2312-B1
AP2312-B2
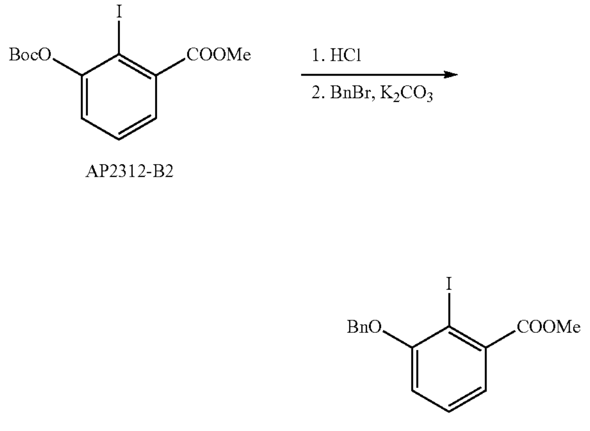
AP2312-B2
AP2312-B
(c) performing Ullmann coupling;
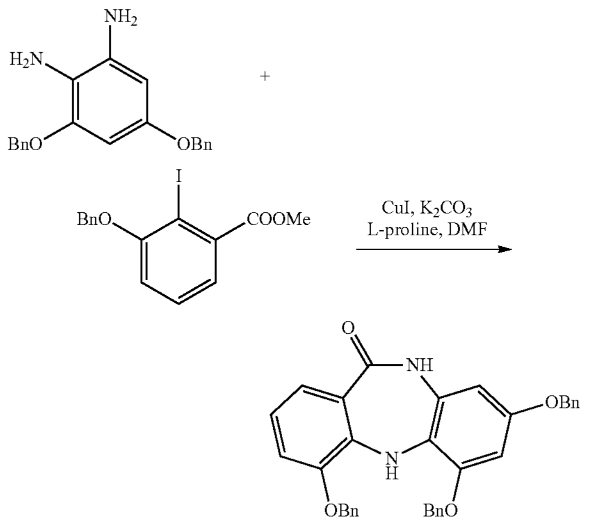
(d) performing de-benzylation;
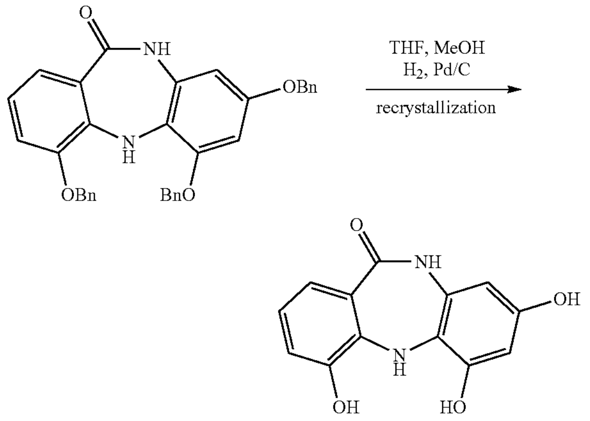
(e) performing silylation;
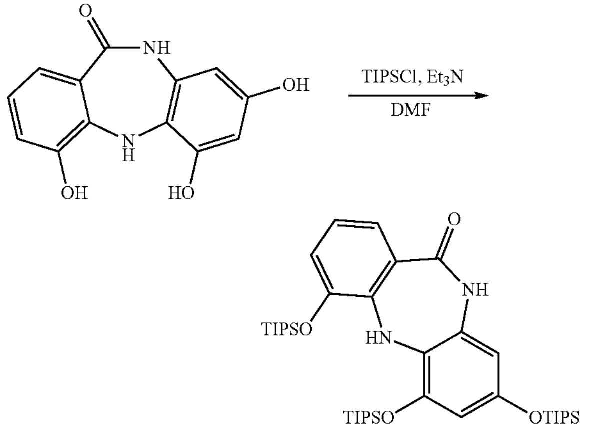

(f) preparing farnesyl bromide;
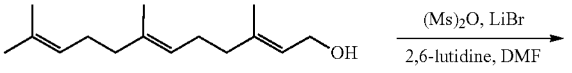
-continued
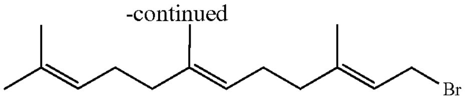
(g) performing farnesylation; and
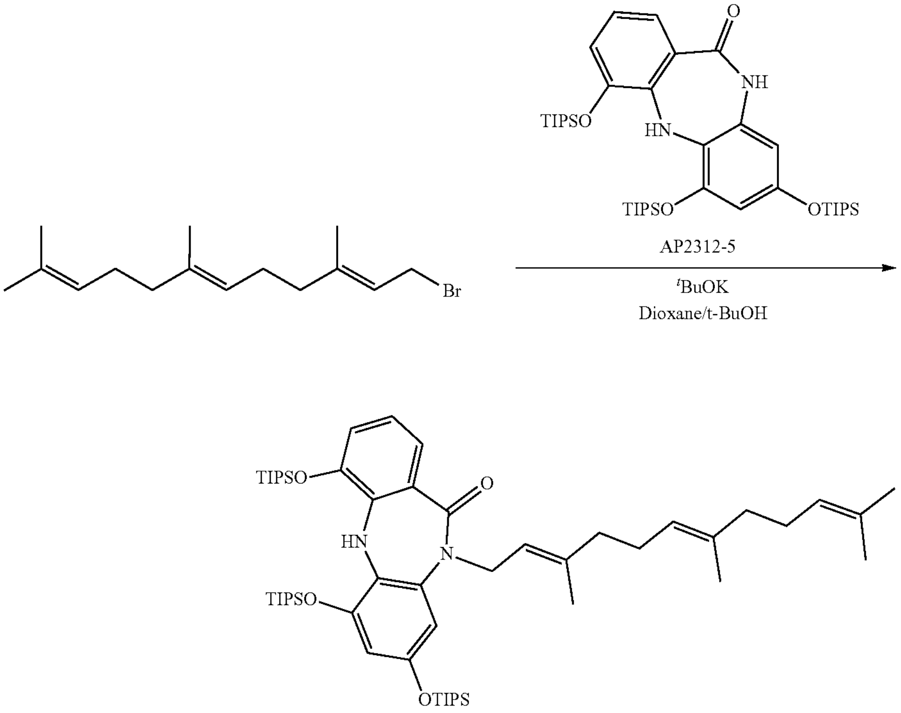
(h) performing de-silylation
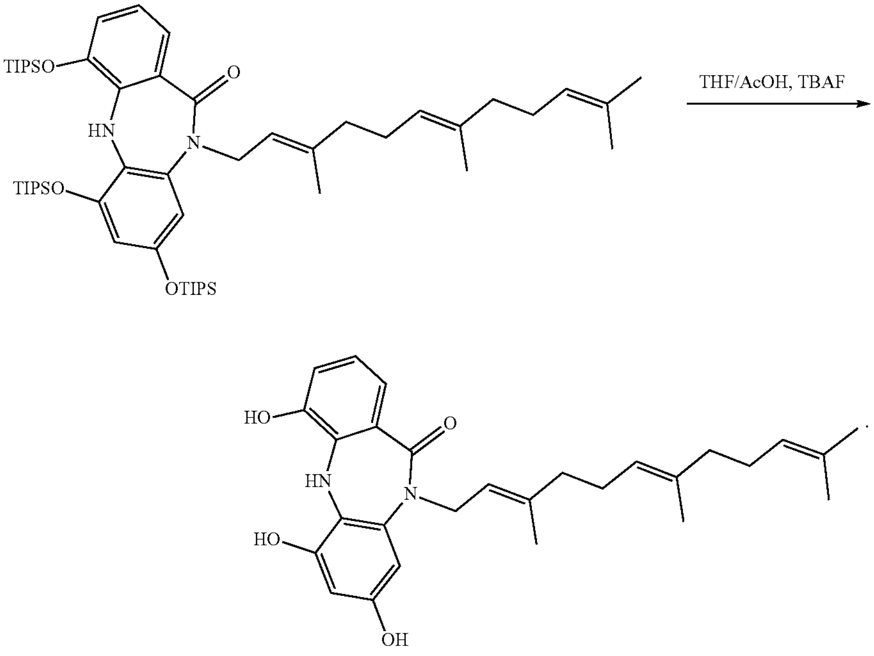

4. A method of synthesizing the farnesyl dibenzodiazepinone AMO-01, said method comprising:

(a) preparing AP2312-A;

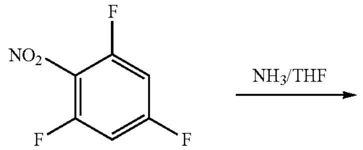

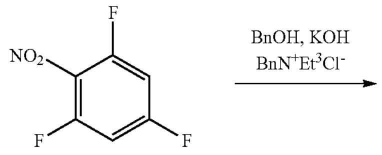

AP2312-1

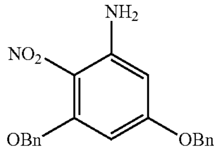

AP2213-2

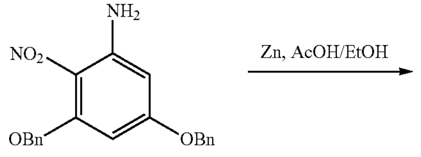

AP2213-2

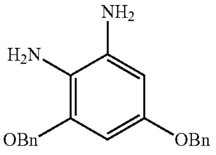

AP2312-A (b) preparing AP2312-B;

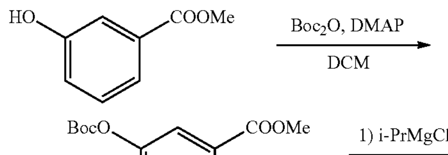

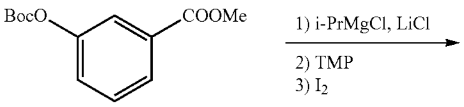

AP2312-B1

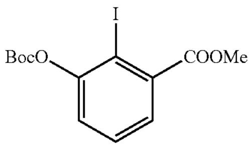

AP2312-B2

-continued

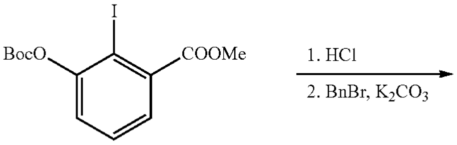

AP2312-B2

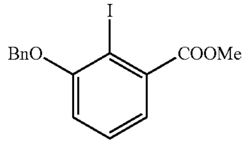

AP2312-B (c) performing Ullmann coupling by reacting molecular equivalent amounts of AP2312-A and AP2312-B in the presence of CuI (0.0525 eq), $K_2CO_3$ (2.0 eq), L-proline (0.1 eq) and DMF to yield AP2312-3;

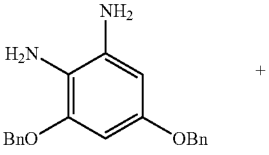

AP2312-A

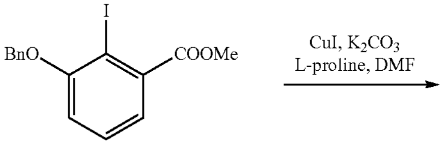

AP2312-B

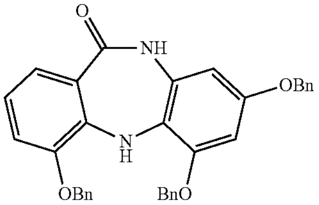

AP2312-3

(d) performing de-benzylation of AP2312-3 in the presence of THF, MeOH and Pd/C under $H_2$ to yield AP2312-4;

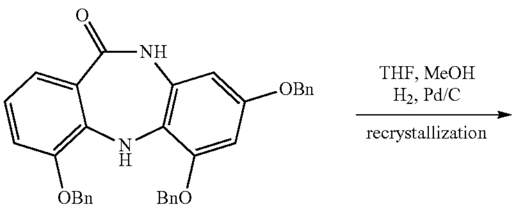

AP2312-3

-continued
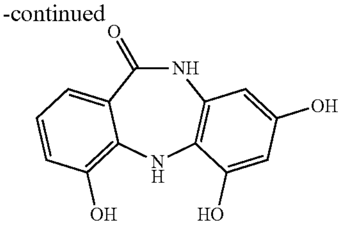
AP2312-4
(e) performing silylation of AP2312-4 in the presence of TIPSCl (4.0 eq) $Et_3N$ (5.0 eq) and DMF to yield AP2312-5;
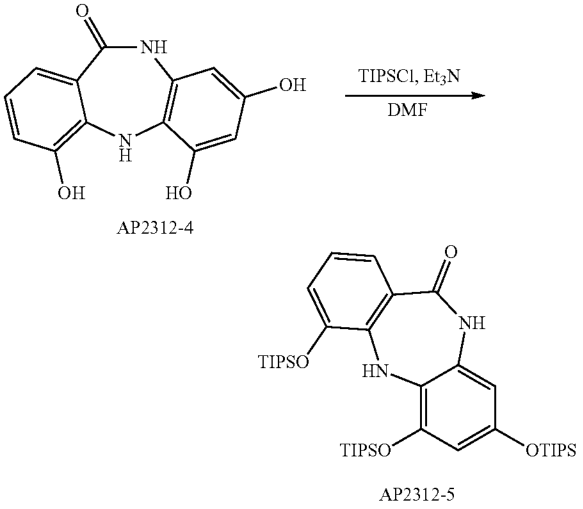
(f) reacting AP23132-C in the presence of $Ms_2O$, LiBr (1.6 eq), 2,6-lutidine (1.6 eq) and DMF to yield AP2312-6;
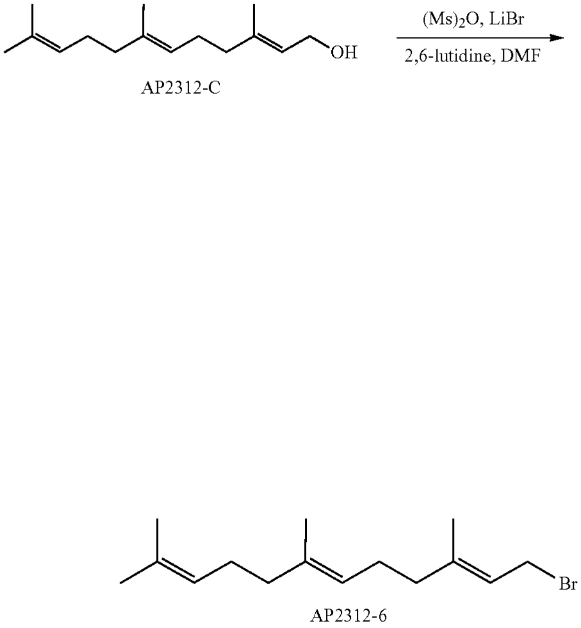
(g) performing farnesylation of AP2312-5 with AP2312-6 in the presence of dioxane, $^t$BuOH and $^t$BuOK (1.15 eq) to yield AP2312-8; and
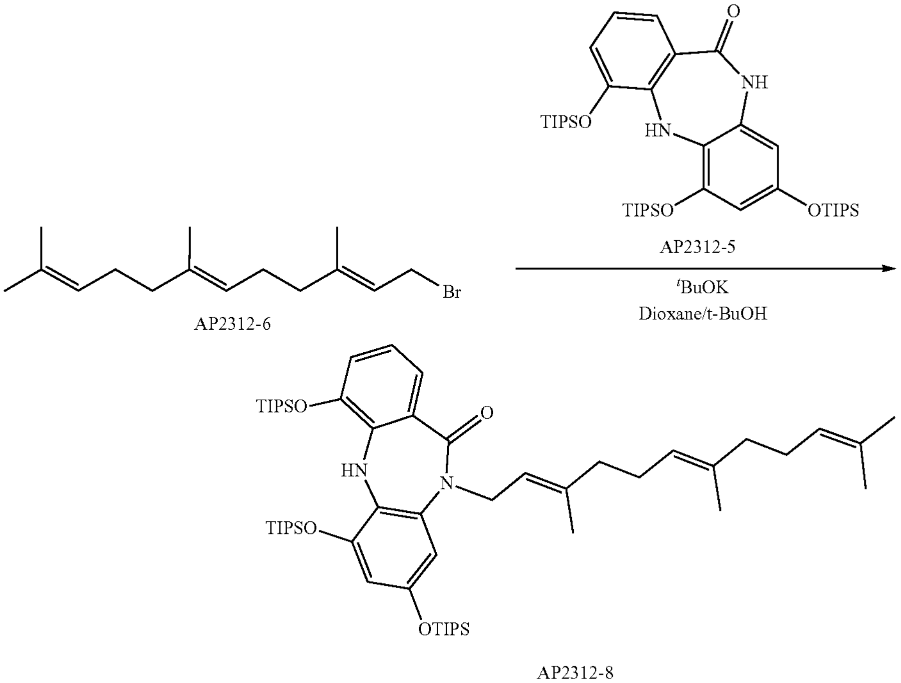

(h) performing de-silylation of AP2312-8 in the presence of THF (1.0 eq), AcOH (8.0 eq) and TBAF (4.0 eq) to yield AMO-01
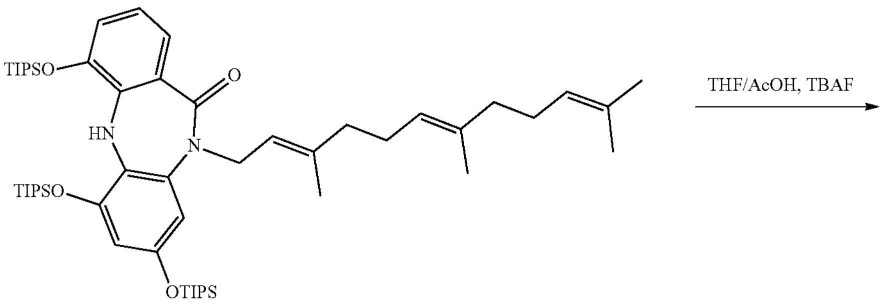
AP2312-8
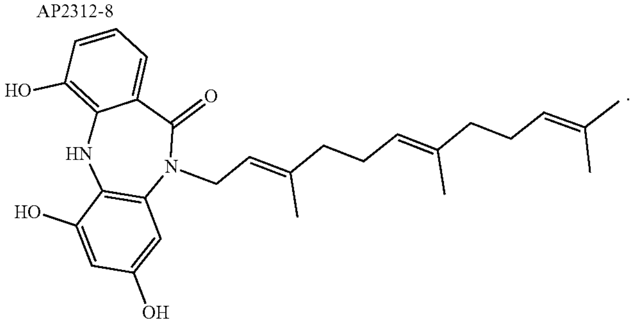
AMO-01
* * * * *